US009416120B2

(12) United States Patent
Yuan et al.

(10) Patent No.: US 9,416,120 B2
(45) Date of Patent: Aug. 16, 2016

(54) BENZOFURAN-2-SULFONAMIDES PYRIDINE DERIVATIVES AS CHEMOKINE RECEPTOR MODULATORS

(71) Applicant: Allergan, Inc., Irvine, CA (US)

(72) Inventors: Haiqing Yuan, Irvine, CA (US); Richard L. Beard, Newport Beach, CA (US); Michael E. Garst, Newport Beach, CA (US); Xiaoxia Liu, Lake Forest, CA (US); John E. Donello, Dana Point, CA (US); Veena Viswanath, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 36 days.

(21) Appl. No.: 14/334,145

(22) Filed: Jul. 17, 2014

(65) Prior Publication Data
US 2014/0329813 A1 Nov. 6, 2014

Related U.S. Application Data

(62) Division of application No. 13/782,174, filed on Mar. 1, 2013, now Pat. No. 8,815,915.

(60) Provisional application No. 61/605,300, filed on Mar. 1, 2012.

(51) Int. Cl.
*A61K 31/44* (2006.01)
*A01N 43/40* (2006.01)
*C07D 307/78* (2006.01)
*C07D 405/12* (2006.01)
*C07D 307/82* (2006.01)
*C07D 405/14* (2006.01)

(52) U.S. Cl.
CPC ............ *C07D 307/78* (2013.01); *C07D 307/82* (2013.01); *C07D 405/12* (2013.01); *C07D 405/14* (2013.01)

(58) Field of Classification Search
CPC ............................ C07D 405/12; C07D 405/14
USPC ................................... 514/332, 333, 336, 337
See application file for complete search history.

(56) References Cited

U.S. PATENT DOCUMENTS

| 7,393,873 | B2 | 7/2008 | Anthony et al. | |
| 7,622,583 | B2 | 11/2009 | Ungashe et al. | |
| 7,884,110 | B2 | 2/2011 | Krasinski et al. | |
| 7,931,909 | B2 | 4/2011 | Hughes et al. | |
| 8,450,367 | B2 * | 5/2013 | Yuan | C07F 9/304 514/470 |
| 8,524,745 | B2 * | 9/2013 | Yuan | C07D 417/12 514/338 |
| 8,580,779 | B2 * | 11/2013 | Yuan | C07C 311/21 424/400 |
| 8,815,915 | B2 * | 8/2014 | Yuan | C07D 405/14 514/333 |
| 8,877,804 | B2 * | 11/2014 | Yuan | C07F 9/304 514/470 |
| 8,927,544 | B2 * | 1/2015 | Yuan | C07D 405/14 514/233.5 |
| 2007/0021466 | A1 * | 1/2007 | Ungashe | C07D 213/50 514/332 |
| 2007/0037794 | A1 | 2/2007 | Ungashe et al. | |
| 2008/0293720 | A1 | 11/2008 | Cleary et al. | |
| 2011/0118248 | A1 | 5/2011 | Ungashe et al. | |
| 2012/0014997 | A1 | 1/2012 | Ungashe et al. | |
| 2014/0275132 | A1 * | 9/2014 | Beard | C07D 409/12 514/269 |
| 2015/0218119 | A1 * | 8/2015 | Yuan | C07D 405/14 514/233.5 |

FOREIGN PATENT DOCUMENTS

| WO | 03-099773 | 4/2003 |
| WO | 2008-008374 | 1/2008 |
| WO | 2009-057811 | 5/2009 |
| WO | 2012-082633 | 6/2012 |

OTHER PUBLICATIONS

Ambati, Jayakrishna et al, An Animal Model of Age-Related Macular Degeneration in Senescent Ccl-2- or Ccr-2Deficient Mice, Nature Medicine, 2003, 1390-1397, 9.
Beech, John et al, Neuroprotection in Ischemia—Reperfusion Injury: An Antiinflammatory Approach Using a Novel Broad-Spectrum Chemokine Inhibitor, Journal of Cerebral Blood Flow and Metabolism, 2001, 683-689, 21.
Fang, I-Mo et al, Expression of chemokine and receptors in Lewis rats with experimental autoimmune anterior uveitis, Experimental Eye Research, 2004, 1043-1055, 78, US.
Feria, Manuel et al, The CCR2 Receptor as a Therapeutic Target, Expert Opin. Ther Patents, 2006, 49-57, 16.
Gerard, Craig et al, Chemokines and Disease, nature immunology, Chemokine Reviews, 2001, 108-115, 2, Nature Publishing Group.
Keino, Kiroshi et al, Chemokine and Chemokine Receptor Expression During Experimental Autoimmune Uveoretinitis in Mice, Graefe's Arch Clin Exp Ophthalmol, 2003, 111-115, 241.
Klitgaard, Torben et al, Chemokine Receptors and Early Activation Markers in Acute Anterior Uveitis, Acta Ophthalmol. Scand., 2004, 179-183, 82.
Meleth, Annal et al, Serum Inflammatory Makers in Diabetic Retinopathy, Investigative Ophthalmology & Visual Science, Nov. 2005, 4295-4301, 46.
Park, Chul Min et al, Synthesis and Structure-Activity Relationship of 1 H-Indole-3-Carboxylic Acid Pyridine-3-Ylamides: A Novel Series of 5-HT2C Receptor Antagonists, Bioorganic & Medicinal Chemistry Letters, 2008, 3844-3847, 18.

(Continued)

*Primary Examiner* — My-Chau T Tran
(74) *Attorney, Agent, or Firm* — Jonathan York Bass

(57) ABSTRACT

The present invention relates to novel benzofuran-2-sulfonamide pyridine derivatives, processes for preparing them, pharmaceutical compositions containing them and their use as pharmaceuticals as modulators of chemokine receptors.

8 Claims, No Drawings

(56) References Cited

OTHER PUBLICATIONS

Reckless, Jill et al, Identification of Oligopeptide Sequences Which Inhibit Migration Induced by a Wide Range of Chemokines, Biochem. J., 1999, 803-811, 340, GB.

Stahl, Heinrich et al, Handbook of Pharmaceutical Salts, Verlag Helvetica Chimica Acta—Zurich, 2002, 329-345.

Takeuchi, Aya et al, CCR5-Deficient Mice Develop Experimental Autoimmune Uveoretinitis in the Context of a Deviant Effector Response, Investigative Ophthalmology & Visual Science, Oct. 2005, 3753-3760, 46, US.

Tokuyama, Hirotake et al, The Simultaneous Blockage of Chemokine Receptors CCR2, CCR5 and CXCR3 by a Non-peptide Chemokine Receptor Antagonist Protects Mice From Dextran Sodium Sulfate-Mediated Colitis, International Immunology, 2005, 1023-1034, 17, US.

Tuaillon, Nadine et al, MCP-1 Expression in Endotoxin-Induced Uveitis, Investigative Ophthalmology & Visual Science, May 2002, 1493-1498, 43.

Wallace, Graham et al, The Role of Chemokines and Their Receptors in Ocular Disease, Progress in Retinal and Eye Research, 2004, 435-448, 23, Elsevier Ltd.

Weisberg, Stuart et al, CCR2 Modulates Inflammatory and Metabolic Effects of High-Fat Feeding, The Journal of Clinical Investigation, Jan. 2006, 115-124, 116.

Wells, Timothy et al, Chemokine blockers—therapeutics in the making?, Trends in Pharmacological Sciences, Jan. 2006, 41-47, 27.

Yamagami, Satoru et al, CCR5 Chemokine Receptor Mediates Recruitment of MHC Class II-Positive Langerhans Cells in the Mouse Corneal Epithelium, Investigative Ophthalmology & Visual Science, Apr. 2005, 1201-1207, 46.

Yang, Chang-Hao et al, Effects of the NF-kB Inhibitor Pyrrolidine Dithiocarbamate on Experimentally Induced Autoimmune Anterior Uveitis, Investigative Ophthalmology & Visual Science, 2005, 1339-1347, 46.

* cited by examiner

BENZOFURAN-2-SULFONAMIDES PYRIDINE DERIVATIVES AS CHEMOKINE RECEPTOR MODULATORS

RELATED APPLICATION

This application claims the benefit of U.S. Non Provisional application Ser. No. 13/782,174, filed Mar. 1, 2013, which claims the benefit of U.S. Provisional Application Ser. No. 61/605,300, filed Mar. 1, 2012, which are incorporated herein by reference in their entirety.

FIELD OF THE INVENTION

The present invention relates to novel benzofuran-2-sulfonamide pyridine derivatives, processes for preparing them, pharmaceutical compositions containing them and their use as pharmaceuticals as modulators of chemokine receptors. The invention relates specifically to the use of these compounds and their pharmaceutical compositions to treat disorders associated with chemokine receptor modulation.

BACKGROUND OF THE INVENTION

Chemokines are a group of 7- to 14-kd peptides that play an important role in orchestrating leukocyte recruitment and migration during inflammation, and therefore represent an important target for anti-inflammatory therapies (Wells et al., 2006). They act by binding to seven-transmembrane, G protein-coupled receptors, the chemokine receptors. The chemokine system is complex, with about 50 chemokines and 20 chemokine receptors identified in humans, often acting with redundancy, making selection of specific antagonists difficult (Gerard and Rollins, 2001). Genetic knockout strategies have confirmed the importance of chemokines as regulators of immune function, but the deletion of specific chemokines has led to only specific and relatively mild defects in the inflammatory response further emphasizing the complex redundancy of the system. Selectivity is crucial for use of chemokine receptor antagonists in systemic diseases where a single chemokine-receptor system is implicated such as atheroscelorsis where the macrophagemonocyte system is the major player in order to allow a subtle and specific control over immune function (Weisberg et al., 2006; Feria and Diaz Gonzalez et al., 2006).

Many ocular conditions are characterized by inappropriate migration and infiltration of cells such as leukocytes and endothelial cells into the eye with deleterious effects to ocular structures (Wallace et al., 2004). Chemokines have been identified in such diseases and misregulation of the chemokine system is apparent in corneal graft rejection, diabetic retinopathy, age-related macular degeneration (ARMD), chronic inflammatory diseases such as uveitis, dry eye etc. Mice lacking CCR2 or MCP-1 develop features of ARMD with age, including drusen deposits, choroidal neovascularization and photoreceptor atrophy indicating a crucial role for this chemokine and its receptor signaling (Amabati et al., 2003). Thus CCR2 receptor-specific inhibitor might have potential therapeutic benefit in ocular diseases like ARMD. In contrast, various human and animal studies have identified several chemokines in different forms of uveitis, produced both by resident and infiltrating cells, that strongly suggests a prominent role for these molecules in its pathogenesis. Studies in rat and mice models of uveitis have demonstrated up-regulation of monocyte chemoattractant protein-1 (MCP-1), macrophage inflammatory protein-1 (MIP-1), RANTES, stromal derived factor-1 (SDF-1) which are powerful chemoattractants for monocytes and T-cells (Fang et al., 2004; Keino et al., 2003). Similar findings have been reported in peripheral blood mononuclear cells in patients with acute anterior uveitis (AAU), the most common form of human uveitis (Klitgaard et al., 2004). MCP-1 knockout mice and CCR5 knockout mice show reduced endotoxin-induced uveitis, which is the animal model for AAU (Takeuchi et al., 2005; Tuallion et al., 2002). It has also been demonstrated that blocking the chemokine system upstream with the use of NF-κB blockers significantly attenuates experimental AAU in rats (Yang et al., 2005). Blockage of NF-κB results in transcriptional inhibition of multiple chemokines. Given the complexity of pathogenesis in uveitis it is unlikely that a selective inhibition of a chemokine receptor in monotherapy will offer therapeutic benefit. A similar role of multiple chemokines have been shown to be correlated with clinical stage of disease in diabetic retinopathy and dry eye (Meleth et al., 2005; Yamagami et al., 2005). In these ocular diseases the use of broad spectrum chemokine receptor inhibitor which inhibits the function of a wide range of chemokines may be beneficial.

The first broad spectrum chemokine inhibitor (BSCI) to be reported was termed Peptide 3, which was derived from the sequence of human chemokine MCP-1 and was shown to block the migration of monocytes in response to MCP-1, MIP-1, RANTES and SDF-1 (Reckless and Grainger. 1999). A cyclic retro inverse analogue of Peptide 3, constructed of D-amino acids in the reverse sequence, called NR58-3.14.3 was observed to be a more potent chemokine inhibitor (Beech et al., 2001). NR58-3.14.3 has been used to test for anti-inflammatory activities in animal models of atherosclerosis, lung inflammation, irritable bowel syndrome etc (Beech et al., 2001; Grainger and Reckless. 2003; Tokuyama et al., 2005). However there are several disadvantages to using these BSCI as a long-term therapeutic strategy. The known BSCIs which are peptides which have relatively low potency, poor pharmacokinetics, and are unstable in vivo. In addition, systemic use of broad spectrum chemokine receptor inhibitors could potentially lead to deleterious side effects due to their systemic anti-inflammatory activity. However in ocular diseases, a local or topical application would prevent the broad spectrum inhibitor to be taken up systemically. Identification of a small molecule inhibitor of several chemokine receptors could be very useful for treatment of inflammatory ocular diseases. Given the evidence for the role of multiple chemokines in several ocular diseases and these results, we propose that the use of small and large molecule broad spectrum chemokine receptor inhibitors will have utility in the local treatment of ocular inflammatory diseases including, but not limited to, uveitis, dry eye, diabetic retinopathy, allergic eye disease and proliferative retinopathies. Manipulation of multiple chemokines therefore represents a novel therapeutic approach in treating ocular diseases.

WO2008008374 discloses CCR2 inhibitors and methods of use thereof.

WO03099773 discloses CCR9 inhibitors and methods of use thereof.

US2012014997 discloses CCR9 inhibitors and methods of use thereof.

U.S. Pat. No. 7,622,583 discloses heteroaryl sulfonamides as antagonists of the CCR2 receptor.

US20110118248 discloses heteroaryl sulfonamides as antagonists of the CCR2 receptor.

U.S. Pat. No. 7,884,110 discloses CCR2 inhibitors and methods of use thereof.

US 20080293720 discloses pyridinyl sulfonamide modulators of chemokine receptors.

Ser. No. 7,393,873 discloses arylsulfonamide derivatives.

SUMMARY OF THE INVENTION

A group of novel benzofuran-2-sulfonamide pyridine derivatives which are potent and selective chemokine receptor modulators, has been now discovered. As such, the compounds described herein are useful in treating a wide variety of disorders associated with modulation of chemokine receptors. The term "modulator" as used herein, includes but is not limited to: receptor agonist, antagonist, inverse agonist, inverse antagonist, partial agonist, partial antagonist.

This invention describes compounds of Formula I, which have chemokine receptor biological activity. The compounds in accordance with the present invention are thus of use in medicine, for example in the treatment of humans with diseases and conditions that are alleviated by chemokine receptor modulation.

In one aspect, the invention provides a compound having Formula I or a pharmaceutically acceptable salt thereof or stereoisomeric forms thereof, or the individual geometrical isomers, enantiomers, diastereoisomers, tautomers, zwitterions and pharmaceutically acceptable salts thereof:

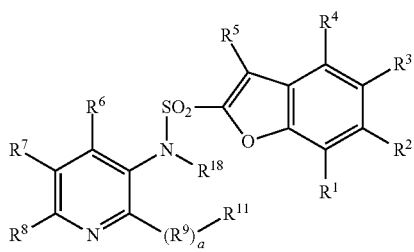

Formula I wherein:
R$^1$ is hydrogen, halogen, CN, substituted or unsubstituted C$_{1-6}$ alkyl, OR$^{12}$, NR$^{13}$R$^{14}$, or COR$^{15}$;
R$^2$ is hydrogen, halogen, CN, substituted or unsubstituted C$_{1-6}$ alkyl, OR$^{12}$, NR$^{13}$R$^{14}$, or COR$^{15}$;
R$^3$ is hydrogen, halogen, CN, substituted or unsubstituted C$_{1-6}$ alkyl, OR$^{12}$, NR$^{13}$R$^{14}$, or COR$^{15}$;
R$^4$ is hydrogen, halogen, CN, substituted or unsubstituted C$_{1-6}$ alkyl, OR$^{12}$, NR$^{13}$R$^{14}$, or COR$^{15}$;
R$^5$ is hydrogen, halogen, CN, substituted or unsubstituted C$_{1-6}$ alkyl, OR$^{12}$, NR$^{13}$R$^{14}$, or COR$^{15}$;
R$^6$ is hydrogen, halogen, CN, substituted or unsubstituted C$_{1-6}$ alkyl, OR$^{12}$, NR$^{13}$R$^{14}$, or COR$^{15}$;
R$^7$ is hydrogen, halogen, CN, substituted or unsubstituted C$_{1-6}$ alkyl, OR$^{12}$, NR$^{13}$R$^{14}$, or COR$^{15}$;
R$^8$ is hydrogen, halogen, CN, substituted or unsubstituted C$_{1-6}$ alkyl, OR$^{12}$, NR$^{13}$R$^{14}$, or COR$^{15}$;
R$^9$ is O, C(O), S, S(O), S(O)$_2$, —C(=NOR$^{16}$)—;
a is 0 or 1;
R$^{11}$ is hydrogen, CN, substituted or unsubstituted C$_{1-6}$ alkyl, CF$_3$, OR$^{12}$, NR$^{13}$R$^{14}$, substituted or unsubstituted C$_{6-10}$ aryl, substituted or unsubstituted heterocycle, substituted or unsubstituted C$_{3-8}$ cycloalkyl, substituted or unsubstituted C$_{2-6}$ alkyne, substituted or unsubstituted C$_{2-6}$ alkene or COR$^{15}$;
R$^{12}$ is hydrogen or substituted or unsubstituted C$_{1-6}$ alkyl;
R$^{13}$ is hydrogen or substituted or unsubstituted C$_{1-6}$ alkyl or can from an optionally substituted heterocycle with R$^{14}$;
R$^{14}$ is hydrogen, substituted or unsubstituted C$_{1-6}$ alkyl, substituted or unsubstituted heterocycle or substituted or unsubstituted C$_{6-10}$ aryl or can from an optionally substituted heterocycle with R$^{13}$;
R$^{15}$ is hydrogen, hydroxyl, substituted or unsubstituted heterocycle, substituted or unsubstituted C$_{6-10}$ aryl or substituted or unsubstituted C$_{1-6}$ alkyl;
R$^{16}$ is hydrogen or substituted or unsubstituted C$_{1-6}$ alkyl; and
R$^{18}$ is hydrogen or substituted or unsubstituted C$_{1-6}$ alkyl.

In another aspect the invention provides a compound having Formula I wherein:
R$^1$ is hydrogen, halogen or substituted or unsubstituted C$_{1-6}$ alkyl;
R$^2$ is hydrogen, halogen or substituted or unsubstituted C$_{1-6}$ alkyl;
R$^3$ is hydrogen, halogen or substituted or unsubstituted C$_{1-6}$ alkyl;
R$^4$ is hydrogen, halogen or substituted or unsubstituted C$_{1-6}$ alkyl;
R$^5$ is hydrogen, halogen or substituted or unsubstituted C$_{1-6}$ alkyl;
R$^6$ is hydrogen, halogen, CN, substituted or unsubstituted C$_{1-6}$ alkyl, OR$^{12}$, NR$^{13}$R$^{14}$, or COR$^{15}$;
R$^7$ is hydrogen, halogen, CN, substituted or unsubstituted C$_{1-6}$ alkyl, OR$^{12}$, NR$^{13}$R$^{14}$, or COR$^{15}$;
R$^8$ is hydrogen, halogen, CN, substituted or unsubstituted C$_{1-6}$ alkyl, OR$^{12}$, NR$^{13}$R$^{14}$, or COR$^{15}$;
R$^9$ is S, S(O) or S(O)$_2$;
a is 0 or 1;
R$^{11}$ is hydrogen, CN, substituted or unsubstituted C$_{1-6}$ alkyl, CF$_3$, OR$^{12}$, NR$^{13}$R$^{14}$, substituted or unsubstituted C$_{6-10}$ aryl, substituted or unsubstituted heterocycle, substituted or unsubstituted C$_{3-8}$ cycloalkyl, substituted or unsubstituted C$_{2-6}$ alkyne, substituted or unsubstituted C$_{2-6}$ alkene or COR$^{15}$;
R$^{12}$ is hydrogen or substituted or unsubstituted C$_{1-6}$ alkyl;
R$^{13}$ is hydrogen or substituted or unsubstituted C$_{1-6}$ alkyl or can from an optionally substituted heterocycle with R$^{14}$;
R$^{14}$ is hydrogen, substituted or unsubstituted C$_{1-6}$ alkyl, substituted or unsubstituted heterocycle or substituted or unsubstituted C$_{6-10}$ aryl or can from an optionally substituted heterocycle with R$^{13}$;
R$^{15}$ is hydrogen, hydroxyl, substituted or unsubstituted heterocycle, substituted or unsubstituted C$_{6-10}$ aryl or substituted or unsubstituted C$_{1-6}$ alkyl; and
R$^{18}$ is hydrogen or substituted or unsubstituted C$_{1-6}$ alkyl.

In another aspect the invention provides a compound having Formula I wherein:
R$^1$ is hydrogen, halogen or substituted or unsubstituted C$_{1-6}$ alkyl;
R$^2$ is hydrogen, halogen or substituted or unsubstituted C$_{1-6}$ alkyl;
R$^3$ is hydrogen, halogen or substituted or unsubstituted C$_{1-6}$ alkyl;
R$^4$ is hydrogen, halogen or substituted or unsubstituted C$_{1-6}$ alkyl;
R$^5$ is hydrogen, halogen or substituted or unsubstituted C$_{1-6}$ alkyl;
R$^6$ is hydrogen, halogen, CN, substituted or unsubstituted C$_{1-6}$ alkyl, OR$^{12}$, NR$^{13}$R$^{14}$, or COR$^{15}$;
R$^7$ is hydrogen, halogen, CN, substituted or unsubstituted C$_{1-6}$ alkyl, OR$^{12}$, NR$^{13}$R$^{14}$, or COR$^{15}$;
R$^8$ is hydrogen, halogen, CN, substituted or unsubstituted C$_{1-6}$ alkyl, OR$^{12}$, NR$^{13}$R$^{14}$, or COR$^{15}$;
R$^9$ is O;
a is 0 or 1;

$R^{11}$ is hydrogen, CN, substituted or unsubstituted $C_{1-6}$ alkyl, $CF_3$, $OR^{12}$, $NR^{13}R^{14}$, substituted or unsubstituted $C_{6-10}$ aryl, substituted or unsubstituted heterocycle, substituted or unsubstituted $C_{3-8}$ cycloalkyl, substituted or unsubstituted $C_{2-6}$ alkyne, substituted or unsubstituted $C_{2-6}$ alkene or $COR^{15}$;

$R^{12}$ is hydrogen or substituted or unsubstituted $C_{1-6}$ alkyl;

$R^{13}$ is hydrogen or substituted or unsubstituted $C_{1-6}$ alkyl or can from an optionally substituted heterocycle with $R^{14}$;

$R^{14}$ is hydrogen, substituted or unsubstituted $C_{1-6}$ alkyl, substituted or unsubstituted heterocycle or substituted or unsubstituted $C_{6-10}$ aryl or can from an optionally substituted heterocycle with $R^{13}$;

$R^{15}$ is hydrogen, hydroxyl, substituted or unsubstituted heterocycle, substituted or unsubstituted $C_{6-10}$ aryl or substituted or unsubstituted $C_{1-6}$ alkyl; and $R^{18}$ is hydrogen or substituted or unsubstituted $C_{1-6}$ alkyl.

In another aspect the invention provides a compound having Formula I wherein:

$R^1$ is hydrogen, halogen or substituted or unsubstituted $C_{1-6}$ alkyl;

$R^2$ is hydrogen, halogen or substituted or unsubstituted $C_{1-6}$ alkyl;

$R^3$ is hydrogen, halogen or substituted or unsubstituted $C_{1-6}$ alkyl;

$R^4$ is hydrogen, halogen or substituted or unsubstituted $C_{1-6}$ alkyl;

$R^5$ is hydrogen, halogen or substituted or unsubstituted $C_{1-6}$ alkyl;

$R^6$ is hydrogen, halogen, CN, substituted or unsubstituted $C_{1-6}$ alkyl, $OR^{12}$, $NR^{13}R^{14}$, or $COR^{15}$;

$R^7$ is hydrogen, halogen, CN, substituted or unsubstituted $C_{1-6}$ alkyl, $OR^{12}$, $NR^{13}R^{14}$, or $COR^{15}$;

$R^8$ is hydrogen, halogen, CN, substituted or unsubstituted $C_{1-6}$ alkyl, $OR^{12}$, $NR^{13}R^{14}$, or $COR^{15}$;

$R^9$ is C(O);

a is 0 or 1;

$R^{11}$ is hydrogen, CN, substituted or unsubstituted $C_{1-6}$ alkyl, $CF_3$, $OR^{12}$, $NR^{13}R^{14}$, substituted or unsubstituted $C_{6-10}$ aryl, substituted or unsubstituted heterocycle, substituted or unsubstituted $C_{3-8}$ cycloalkyl, substituted or unsubstituted $C_{2-6}$ alkyne, substituted or unsubstituted $C_{2-6}$ alkene or $COR^{15}$;

$R^{12}$ is hydrogen or substituted or unsubstituted $C_{1-6}$ alkyl;

$R^{13}$ is hydrogen or substituted or unsubstituted $C_{1-6}$ alkyl or can from an optionally substituted heterocycle with $R^{14}$;

$R^{14}$ is hydrogen, substituted or unsubstituted $C_{1-6}$ alkyl, substituted or unsubstituted heterocycle or substituted or unsubstituted $C_{6-10}$ aryl or can from an optionally substituted heterocycle with $R^{13}$;

$R^{15}$ is hydrogen, hydroxyl, substituted or unsubstituted heterocycle, substituted or unsubstituted $C_{6-10}$ aryl or substituted or unsubstituted $C_{1-6}$ alkyl; and $R^{18}$ is hydrogen or substituted or unsubstituted $C_{1-6}$ alkyl.

In another aspect the invention provides a compound having Formula I wherein:

$R^1$ is hydrogen, halogen or substituted or unsubstituted $C_{1-6}$ alkyl;

$R^2$ is hydrogen, halogen or substituted or unsubstituted $C_{1-6}$ alkyl;

$R^3$ is hydrogen, halogen or substituted or unsubstituted $C_{1-6}$ alkyl;

$R^4$ is hydrogen, halogen or substituted or unsubstituted $C_{1-6}$ alkyl;

$R^5$ is hydrogen, halogen or substituted or unsubstituted $C_{1-6}$ alkyl;

$R^6$ is hydrogen, halogen, CN, substituted or unsubstituted $C_{1-6}$ alkyl, $OR^{12}$, $NR^{13}R^{14}$, or $COR^{15}$;

$R^7$ is hydrogen, halogen, CN, substituted or unsubstituted $C_{1-6}$ alkyl, $OR^{12}$, $NR^{13}R^{14}$, or $COR^{15}$;

$R^8$ is hydrogen, halogen, CN, substituted or unsubstituted $C_{1-6}$ alkyl, $OR^{12}$, $NR^{13}R^{14}$, or $COR^{15}$;

$R^9$ is —C(=NOR$^{16}$)—;

a is 0 or 1;

$R^{11}$ is hydrogen, CN, substituted or unsubstituted $C_{1-6}$ alkyl, $CF_3$, $OR^{12}$, $NR^{13}R^{14}$, substituted or unsubstituted $C_{6-10}$ aryl, substituted or unsubstituted heterocycle, substituted or unsubstituted $C_{3-8}$ cycloalkyl, substituted or unsubstituted $C_{2-6}$ alkyne, substituted or unsubstituted $C_{2-6}$ alkene or $COR^{15}$;

$R^{12}$ is hydrogen or substituted or unsubstituted $C_{1-6}$ alkyl;

$R^{13}$ is hydrogen or substituted or unsubstituted $C_{1-6}$ alkyl or can from an optionally substituted heterocycle with $R^{14}$;

$R^{14}$ is hydrogen, substituted or unsubstituted $C_{1-6}$ alkyl, substituted or unsubstituted heterocycle or substituted or unsubstituted $C_{6-10}$ aryl or can from an optionally substituted heterocycle with $R^{13}$;

$R^{15}$ is hydrogen, hydroxyl, substituted or unsubstituted heterocycle, substituted or unsubstituted $C_{8-10}$ aryl or substituted or unsubstituted $C_{1-6}$ alkyl;

$R^{16}$ is hydrogen or substituted or unsubstituted $C_{1-6}$ alkyl; and $R^{18}$ is hydrogen or substituted or unsubstituted $C_{1-6}$ alkyl.

In another aspect the invention provides a compound having Formula I wherein:

$R^1$ is hydrogen, halogen, CN, substituted or unsubstituted $C_{1-6}$ alkyl, $OR^{12}$, $NR^{13}R^{14}$, or $COR^{15}$;

$R^2$ is hydrogen, halogen, CN, substituted or unsubstituted $C_{1-6}$ alkyl, $OR^{12}$, $NR^{13}R^{14}$, or $COR^{15}$;

$R^3$ is hydrogen, halogen, CN, substituted or unsubstituted $C_{1-6}$ alkyl, $OR^{12}$, $NR^{13}R^{14}$, or $COR^{15}$;

$R^4$ is hydrogen, halogen, CN, substituted or unsubstituted $C_{1-6}$ alkyl, $OR^{12}$, $NR^{13}R^{14}$, or $COR^{15}$;

$R^5$ is hydrogen, halogen, CN, substituted or unsubstituted $C_{1-6}$ alkyl, $OR^{12}$, $NR^{13}R^{14}$, or $COR^{15}$;

$R^6$ is hydrogen, halogen, CN, substituted or unsubstituted $C_{1-6}$ alkyl, $OR^{12}$, $NR^{13}R^{14}$, or $COR^{15}$;

$R^7$ is hydrogen, halogen, CN, substituted or unsubstituted $C_{1-6}$ alkyl, $OR^{12}$, $NR^{13}R^{14}$, or $COR^{15}$;

$R^8$ is hydrogen, halogen, CN, substituted or unsubstituted $C_{1-6}$ alkyl, $OR^{12}$, $NR^{13}R^{14}$, or $COR^{15}$;

$R^9$ is O, C(O), S, S(O), S(O)$_2$, —C(=NOR$^{16}$)—;

a is 1;

$R^{11}$ is hydrogen, CN, substituted or unsubstituted $C_{1-6}$ alkyl, $CF_3$, $OR^{12}$, $NR^{13}R^{14}$, substituted or unsubstituted $C_{6-10}$ aryl, substituted or unsubstituted heterocycle, substituted or unsubstituted $C_{3-8}$ cycloalkyl, substituted or unsubstituted $C_{2-6}$ alkyne, substituted or unsubstituted $C_{2-6}$ alkene or $COR^{15}$;

$R^{12}$ is hydrogen or substituted or unsubstituted $C_{1-6}$ alkyl;

$R^{13}$ is hydrogen or substituted or unsubstituted $C_{1-6}$ alkyl or can from an optionally substituted heterocycle with $R^{14}$;

$R^{14}$ is hydrogen, substituted or unsubstituted $C_{1-6}$ alkyl, substituted or unsubstituted heterocycle or substituted or unsubstituted $C_{6-10}$ aryl or can from an optionally substituted heterocycle with $R^{13}$;

$R^{15}$ is hydrogen, hydroxyl, substituted or unsubstituted heterocycle, substituted or unsubstituted $C_{6-10}$ aryl or substituted or unsubstituted $C_{1-6}$ alkyl;

$R^{16}$ is hydrogen or substituted or unsubstituted $C_{1-6}$ alkyl; and $R^{18}$ is hydrogen or substituted or unsubstituted $C_{1-6}$ alkyl.

In another aspect the invention provides a compound having Formula I wherein $R^1$ is hydrogen;
$R^2$ is hydrogen;
$R^3$ is hydrogen;
$R^4$ is hydrogen;
$R^5$ is hydrogen;
$R^6$ is hydrogen;
$R^7$ is hydrogen, halogen, substituted or unsubstituted $C_{1-6}$ alkyl;
$R^8$ is hydrogen;
$R^9$ is O, C(O), S, S(O) or S(O)$_2$;
a is 1;
$R^{11}$ is substituted or unsubstituted $C_{1-6}$ alkyl, $NR^{13}R^{14}$, substituted or unsubstituted $C_{6-10}$ aryl, substituted or unsubstituted heterocycle, substituted or unsubstituted $C_{3-8}$ cycloalkyl;
$R^{13}$ forms an optionally substituted heterocycle with $R^{14}$;
$R^{14}$ forms an optionally substituted heterocycle with $R^{13}$; and
$R^{18}$ is hydrogen.

In another aspect the invention provides a compound having Formula I wherein $R^1$ is hydrogen;
$R^2$ is hydrogen;
$R^3$ is hydrogen;
$R^4$ is hydrogen;
$R^5$ is hydrogen;
$R^6$ is hydrogen;
$R^7$ is hydrogen, halogen, substituted or unsubstituted $C_{1-6}$ alkyl;
$R^8$ is hydrogen;
$R^9$ is O, C(O), S, S(O) or S(O)$_2$;
a is 1;
$R^{11}$ is substituted or unsubstituted $C_{1-6}$ alkyl, $NR^{13}R^{14}$, substituted or unsubstituted $C_{6-10}$ aryl, substituted or unsubstituted heterocycle, substituted or unsubstituted $C_{3-8}$ cycloalkyl;
$R^{13}$ forms an optionally substituted heterocycle with $R^{14}$;
$R^{14}$ forms an optionally substituted heterocycle with $R^{13}$; and
$R^{18}$ is hydrogen.

In another aspect the invention provides a compound having Formula I wherein $R^1$ is hydrogen;
$R^2$ is hydrogen;
$R^3$ is hydrogen;
$R^4$ is hydrogen;
$R^5$ is hydrogen;
$R^6$ is hydrogen;
$R^7$ is hydrogen, halogen, substituted or unsubstituted $C_{1-6}$ alkyl;
$R^8$ is hydrogen;
$R^9$ is C(O);
a is 1;
$R^{11}$ is substituted or unsubstituted $C_{1-6}$ alkyl, $NR^{13}R^{14}$, substituted or unsubstituted $C_{6-10}$ aryl, substituted or unsubstituted heterocycle, substituted or unsubstituted $C_{3-8}$ cycloalkyl;
$R^{13}$ forms an optionally substituted heterocycle with $R^{14}$;
$R^{14}$ forms an optionally substituted heterocycle with $R^{13}$; and
$R^{18}$ is hydrogen.

In another aspect the invention provides a compound having Formula I wherein $R^1$ is hydrogen;
$R^2$ is hydrogen;
$R^3$ is hydrogen;
$R^4$ is hydrogen;
$R^5$ is hydrogen;
$R^6$ is hydrogen;
$R^7$ is hydrogen, halogen, substituted or unsubstituted $C_{1-6}$ alkyl;
$R^8$ is hydrogen;
$R^9$ is S, S(O) or S(O)$_2$;
a is 1;
$R^{11}$ is substituted or unsubstituted $C_{6-10}$ aryl or substituted or unsubstituted heterocycle; and
$R^{18}$ is hydrogen.

In another aspect the invention provides a compound having Formula I wherein $R^1$ is hydrogen;
$R^2$ is hydrogen;
$R^3$ is hydrogen;
$R^4$ is hydrogen;
$R^5$ is hydrogen;
$R^6$ is hydrogen;
$R^7$ is hydrogen, halogen, substituted or unsubstituted $C_{1-6}$ alkyl;
$R^8$ is hydrogen;
$R^9$ is O, C(O);
a is 1;
$R^{11}$ is substituted or unsubstituted $C_{6-10}$ aryl or substituted or unsubstituted heterocycle; and
$R^{18}$ is hydrogen.

In another aspect the invention provides a compound having Formula I wherein $R^1$ is hydrogen;
$R^2$ is hydrogen;
$R^3$ is hydrogen;
$R^4$ is hydrogen;
$R^5$ is hydrogen;
$R^6$ is hydrogen;
$R^7$ is hydrogen, halogen, substituted or unsubstituted $C_{1-6}$ alkyl;
$R^8$ is hydrogen;
$R^9$ is O, C(O);
a is 1;
$R^{11}$ is substituted or unsubstituted $C_{6-10}$ aryl or substituted or unsubstituted heterocycle; and
$R^{18}$ is hydrogen.

The term "alkyl", as used herein, refers to saturated, monovalent or divalent hydrocarbon moieties having linear or branched moieties or combinations thereof and containing 1 to 6 carbon atoms. One methylene (—CH$_2$—) group, of the alkyl can be replaced by oxygen, sulfur, sulfoxide, nitrogen, carbonyl, carboxyl, sulfonyl, or by a divalent $C_{3-6}$ cycloalkyl. Hydrogen atoms on alkyl groups can be substituted by groups including, but not limited to: halogens, —OH, $C_{3-8}$ cycloalkyl, non-aromatic heterocycles, aromatic heterocycles, —OC$_{1-6}$ alkyl, —NH$_2$, —NO$_2$, amides, carboxylic acids, ketones, ethers, esters, aldehydes, or sulfonamides.

The term "cycloalkyl", as used herein, refers to a monovalent or divalent group of 3 to 8 carbon atoms, derived from a saturated cyclic hydrocarbon. Cycloalkyl groups can be monocyclic or polycyclic. Cycloalkyl can be substituted by groups including, but not limited to: halogens, —OH, $C_{3-8}$ cycloalkyl, non-aromatic heterocycles, aromatic heterocycles, —OC$_{1-6}$ alkyl, —NH$_2$, —NO$_2$, amides, ethers, esters, carboxylic acids, aldehydes, ketones, sulfonamides groups.

The term "cycloalkenyl", as used herein, refers to a monovalent or divalent group of 3 to 8 carbon atoms, derived from a saturated cycloalkyl having one or more double bonds. Cycloalkenyl groups can be monocyclic or polycyclic. Cycloalkenyl groups can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, aldehydes, ketones, carboxylic acids, sulfonamides groups.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. $C_{2-6}$ alkenyl can be in the E or Z configuration. Alkenyl groups can be substituted by $C_{1-6}$ alkyl.

The term "alkynyl", as used herein, refers to a monovalent or divalent hydrocarbon radical having 2 to 6 carbon atoms, derived from a saturated alkyl, having at least one triple bond.

The term "heterocycle" as used herein, refers to a 3 to 10 membered ring, which can be aromatic or non-aromatic, saturated or unsaturated, containing at least one heteroatom selected from O or N or S or combinations of at least two thereof, interrupting the carbocyclic ring structure. The heterocyclic ring can be interrupted by a C=O; the S heteroatom can be oxidized. Heterocycles can be monocyclic or polycyclic. Heterocyclic ring moieties can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, aldehydes, carboxylic acids, ketones, sulfonamides groups.

The term "aryl" as used herein, refers to an organic moiety derived from an aromatic hydrocarbon consisting of a ring containing 6 to 10 carbon atoms by removal of one hydrogen. Aryl can be monocyclic or polycyclic Aryl can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, carboxylic acids, ketones, aldehydes, sulfonamides groups.

The term "amide" as used herein, represents a group of formula "—C(O)NR$^x$R$^y$" or wherein R$^x$ and R$^y$ are the same or independently H or $C_{1-6}$ alkyl.

The term "ketone" as used herein, represents a group of formula "—C(O)R$^x$" wherein R$^x$ is $C_{1-6}$ alkyl.

The term "ester" as used herein, represents a group of formula "—C(O)OR$^x$" wherein R$^x$ is $C_{1-6}$ alkyl.

The term "ether" as used herein, represents a group of formula "—OR$^x$" wherein R$^x$ is $C_{1-6}$ alkyl.

The term "aldehyde" as used herein, represents a group of formula "—C(O)H".

The term "sulfonamide" as used herein, represents a group of formula "—S(O)$_2$NR$^x$R$^y$" wherein R$^x$ and R$^y$ are the same or independently H or $C_{1-6}$ alkyl.

The term "hydroxyl" as used herein, represents a group of formula "—OH".

The term "amino" as used herein, represents a group of formula "—$NH_2$".

The term "carbonyl" as used herein, represents a group of formula "—C(O)—".

The term "carboxyl" as used herein, represents a group of formula "—C(O)O—".

The term "sulfonyl" (sulfone) as used herein, represents a group of formula "—$SO_2$—".

The term "sulfate" as used herein, represents a group of formula "—O—S(O)$_2$—O—".

The term "carboxylic acid" as used herein, represents a group of formula "—C(O)OH".

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—O—P(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom

Compounds of the invention are:

N-[2-(benzylsulfanyl)-5-chloropyridin-3-yl]-1-benzofuran-2-sulfonamide;

N-[2-(benzylsulfinyl)-5-chloropyridin-3-yl]-1-benzofuran-2-sulfonamide;

N-[2-(benzylsulfonyl)-5-chloropyridin-3-yl]-1-benzofuran-2-sulfonamide;

N-{5-chloro-2-[(pyridin-3-ylmethyl)sulfanyl]pyridin-3-yl}-1-benzofuran-2-sulfonamide;

N-{5-chloro-2-[(pyridin-3-ylmethyl)sulfinyl]pyridin-3-yl}-1-benzofuran-2-sulfonamide;

N-{5-chloro-2-[(pyridin-3-ylmethyl)sulfonyl]pyridin-3-yl}-1-benzofuran-2-sulfonamide;

N-(5-chloro-2-{[(1-oxidopyridin-3-yl)methyl]sulfonyl}pyridin-3-yl)-1-benzofuran-2-sulfonamide;

N-[2-(benzylsulfanyl)pyridin-3-yl]-1-benzofuran-2-sulfonamide;

N-[2-(benzylsulfinyl)pyridin-3-yl]-1-benzofuran-2-sulfonamide;

N-[2-(benzylsulfonyl)pyridin-3-yl]-1-benzofuran-2-sulfonamide;

N-{2-[(3-aminobenzyl)sulfanyl]pyridin-3-yl}-1-benzofuran-2-sulfonamide;

N-{2-[(3-aminobenzyl)sulfinyl]pyridin-3-yl}-1-benzofuran-2-sulfonamide;

tert-butyl {3-[({3-[(1-benzofuran-2-ylsulfonyl)amino]pyridin-2-yl}sulfonyl)methyl]phenyl}carbamate;

N-{2-[(3-aminobenzyl)sulfonyl]pyridin-3-yl}-1-benzofuran-2-sulfonamide;

N-[2-(benzylsulfanyl)-5-fluoropyridin-3-yl]-1-benzofuran-2-sulfonamide;

N-[2-(benzylsulfinyl)-5-fluoropyridin-3-yl]-1-benzofuran-2-sulfonamide;

N-[2-(benzylsulfonyl)-5-fluoropyridin-3-yl]-1-benzofuran-2-sulfonamide;

N-{2-[(3-aminobenzyl)sulfanyl]-5-chloropyridin-3-yl}-1-benzofuran-2-sulfonamide;

N-{2-[(3-aminobenzyl)sulfinyl]-5-chloropyridin-3-yl}-1-benzofuran-2-sulfonamide;

N-{2-[(3-aminobenzyl)sulfonyl]-5-chloropyridin-3-yl}-1-benzofuran-2-sulfonamide;

N-[2-(benzylsulfanyl)-5-methylpyridin-3-yl]-1-benzofuran-2-sulfonamide;

N-[2-(benzylsulfinyl)-5-methylpyridin-3-yl]-1-benzofuran-2-sulfonamide;

N-[2-(benzylsulfonyl)-5-methylpyridin-3-yl]-1-benzofuran-2-sulfonamide;

N-{5-chloro-2-[(2-methylpyridin-3-yl)oxy]pyridin-3-yl}-1-benzofuran-2-sulfonamide;

2-({3-[(1-benzofuran-2-ylsulfonyl)amino]-5-chloropyridin-2-yl}oxy)benzoic acid;

methyl 2-({3-[(1-benzofuran-2-ylsulfonyl)amino]-5-chloro-pyridin-2-yl}oxy)benzoate;
N-[5-chloro-2-(morpholin-4-ylcarbonyl)pyridin-3-yl]-1-benzofuran-2-sulfonamide;
N-{5-chloro-2-[(4-oxopiperidin-1-yl)carbonyl]pyridin-3-yl}-1-benzofuran-2-sulfonamide;
N-[5-chloro-2-(phenylcarbonyl)pyridin-3-yl]-1-benzofuran-2-sulfonamide;
N-[5-chloro-2-(phenylsulfanyl)pyridin-3-yl]-1-benzofuran-2-sulfonamide;
N-[5-chloro-2-(phenylsulfonyl)pyridin-3-yl]-1-benzofuran-2-sulfonamide;
N-[5-chloro-2-(phenylsulfinyl)pyridin-3-yl]-1-benzofuran-2-sulfonamide;
N-{5-chloro-2-[(2-methylpyridin-3-yl)methoxy]pyridin-3-yl}-1-benzofuran-2-sulfonamide;
N-[5-chloro-2-(phenylacetyl)pyridin-3-yl]-1-benzofuran-2-sulfonamide;
methyl 2-[({3-[(1-benzofuran-2-ylsulfonyl)amino]-5-chloropyridin-2-yl}sulfanyl)methyl]benzoate;
2-[({3-[(1-benzofuran-2-ylsulfonyl)amino]-5-chloropyridin-2-yl}sulfanyl)methyl]benzoic acid;
methyl 2-[({3-[(1-benzofuran-2-ylsulfonyl)amino]-5-chloropyridin-2-yl}sulfinyl)methyl]benzoate;
methyl 2-[({3-[(1-benzofuran-2-ylsulfonyl)amino]-5-chloropyridin-2-yl}sulfonyl)methyl]benzoate;
2-[({3-[(1-benzofuran-2-ylsulfonyl)amino]-5-chloropyridin-2-yl}sulfonyl)methyl]benzoic acid;
N-[5-fluoro-2-(phenylsulfanyl)pyridin-3-yl]-1-benzofuran-2-sulfonamide;
N-[5-fluoro-2-(phenylsulfinyl)pyridin-3-yl]-1-benzofuran-2-sulfonamide;
N-[5-fluoro-2-(phenylsulfonyl)pyridin-3-yl]-1-benzofuran-2-sulfonamide;
2-[({3-[(1-benzofuran-2-ylsulfonyl)amino]-5-chloropyridin-2-yl}sulfinyl)methyl]benzoic acid;
N-[5-methyl-2-(phenylsulfanyl)pyridin-3-yl]-1-benzofuran-2-sulfonamide;
N-[5-methyl-2-(phenylsulfinyl)pyridin-3-yl]-1-benzofuran-2-sulfonamide;
N-[5-methyl-2-(phenylsulfonyl)pyridin-3-yl]-1-benzofuran-2-sulfonamide;
2-({3-[(1-benzofuran-2-ylsulfonyl)amino]-5-chloropyridin-2-yl}sulfanyl)benzoic acid;
3-({3-[(1-benzofuran-2-ylsulfonyl)amino]-5-chloropyridin-2-yl}sulfanyl)benzoic acid;
2-({3-[(1-benzofuran-2-ylsulfonyl)amino]-5-chloropyridin-2-yl}sulfinyl)benzoic acid;
2-({3-[(1-benzofuran-2-ylsulfonyl)amino]-5-chloropyridin-2-yl}sulfonyl)benzoic acid;
2-[({3-[(1-benzofuran-2-ylsulfonyl)amino]-5-methylpyridin-2-yl}sulfanyl)methyl]benzoic acid;
2-[({3-[(1-benzofuran-2-ylsulfonyl)amino]-5-methylpyridin-2-yl}sulfinyl)methyl]benzoic acid;
methyl 2-[({3-[(1-benzofuran-2-ylsulfonyl)amino]pyridin-2-yl}sulfanyl)methyl]benzoate;
2-[({3-[(1-benzofuran-2-ylsulfonyl)amino]pyridin-2-yl}sulfanyl)methyl]benzoic acid;
methyl 2-[({3-[(1-benzofuran-2-ylsulfonyl)amino]pyridin-2-yl}sulfinyl)methyl]benzoate;
2-[({3-[(1-benzofuran-2-ylsulfonyl)amino]pyridin-2-yl}sulfinyl)methyl]benzoic acid;
methyl 2-[({3-[(1-benzofuran-2-ylsulfonyl)amino]pyridin-2-yl}sulfonyl)methyl]benzoate;
2-[({3-[(1-benzofuran-2-ylsulfonyl)amino]pyridin-2-yl}sulfonyl)methyl]benzoic acid.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic acid and the like (Handbook of Pharmaceutical Salts, P. Heinrich Stahal & Camille G. Wermuth (Eds), Verlag Helvetica Chemica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahal & Camille G. Wermuth (Eds), Verlag Helvetica Chemica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the chemokine receptors.

In another embodiment, there are provided pharmaceutical compositions including at least one compound of the invention in a pharmaceutically acceptable carrier.

In a further embodiment of the invention, there are provided methods for treating disorders associated with modulation of chemokine receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by chemokine receptor modulation. Therapeutic utilities of chemokine receptor modulators are skin inflammatory diseases and conditions, including, but are not limited to: rosacea (dilation of the blood vessels just under the skin), sunburn, chronic sun damage, discreet erythemas, psoriasis, atopic dermatitis, menopause-associated hot flashes, hot flashes resulting from orchiectomyatopic dermatitis, photoaging, seborrheic dermatitis, acne, allergic dermatitis, irritant dermatitis, telangiectasia (dilations of previously existing small blood vessels) of the face, rhinophyma (hypertrophy of the nose with follicular dilation), red bulbous nose, acne-like skin eruptions (may ooze or crust), burning or stinging sensation of the face, irritated and bloodshot and watery eyes, cutaneous hyperactivity with dilation of blood vessels of the skin, Lyell's syndrome, Stevens-Johnson syndrome, erythema multiforme minor, erythema multiforme major and other inflammatory skin diseases, actinic keratoses, arsenic keratoses, inflammatory and non-inflammatory acne, ichthyoses and other keratinization and hyperproliferative disorders of the skin, eczema, wound healing.

Therapeutic utilities of chemokine receptor modulators are ocular inflammatory diseases including, but not limited to, uveitis, dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy, acute macular neuroretinopathy, central serous chorioretinopathy, cystoid macular edema, and diabetic macular edema; uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, and Eales disease; traumatic surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epithelitis.

In still another embodiment of the invention, there are provided methods for treating disorders associated with modulation of chemokine receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular inflammatory diseases including, but not limited to, uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy, acute macular neuroretinopathy, central serous chorioretinopathy, cystoid macular edema, and diabetic macular edema; uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, and Eales disease; traumatic surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epithelitis.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds and their pharmaceutically-acceptable salts may be administered through different routes, including but not limited to topical eye drops, direct injection, application at the back of the eye or formulations that may further enhance the long duration of actions such as a slow releasing pellet, suspension, gel, or sustained delivery devices such as any suitable drug delivery system (DDS) known in the art. While topical administration is preferred, this compound may also be used in an intraocular implant as described in U.S. Pat. No. 7,931,909.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of chemokine receptors. Thus, in further embodiments of the invention, there are provided methods for treating a disorder associated with modulation of chemokine receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. The described benzofuran-2-sulfonamide derivatives were prepared by methods as shown in Scheme 1. Those skilled in the art will be able to routinely modify and/or adapt Scheme 1 to synthesize any compounds of the invention covered by Formula I.

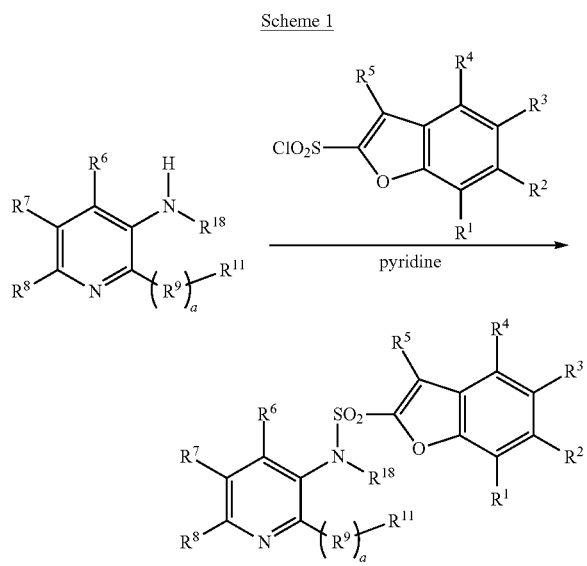

Scheme 1

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

As will be evident to those skilled in the art, individual isomeric forms can be obtained by separation of mixtures thereof in conventional manner. For example, in the case of diasteroisomeric isomers, chromatographic separation may be employed.

Compound names were generated with ACD version 12.0 and some intermediates' and reagents' names used in the examples were generated with software such as Chem Bio Draw Ultra version 12.0 or Auto Nom 2000 from MDL ISIS Draw 2.5 SP1. In general, characterization of the compounds is performed according to the following methods:

NMR spectra are recorded on Varian 600 or Varian 300, in the indicated solvent at ambient temperature; chemical shifts in [ppm], coupling constants in [Hz].

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates were prepared according to published procedures. Solvents were purchased from commercial sources in appropriate quality and used as received. Air and/or moisture-sensitive reactions were run under an Ar- or $N_2$-atmosphere.

Usually the compounds of the invention were purified by chromatography: CombiFlash Companion and RediSep Rf silica gel 60 (0.04-0.063 mm); Preparative thin layer chromatography (PTLC): Analtech (silica gel 60 $F_{254}$, 500 or 1000 µm).

The following abbreviations are used in the examples:
$CH_2Cl_2$ dichloromethane
AcOH acetic acid
NaOH sodium hydroxide
MeOH methanol
$CD_3OD$ deuterated methanol
HCl hydrochloric acid
DMF dimethylformamide
EtOAc ethyl acetate
$CDCl_3$ deuterated chloroform
$CHCl_3$ chloroform
DMSO-$d_6$ deuterated dimethyl sulfoxide
THF tetrahydrofuran
$K_2CO_3$ potassium carbonate
$Et_3N$ triethylamine
$Na_2SO_4$ sodium sulfate
$iPr_2NEt$ N,N'-diisopropylethylamine
MPLC medium pressure liquid chromatography
$NH_4Cl$ Ammonium chloride mCPBA 3-Chloroperoxybenzoic acid
KOH potassium hydroxide
Et$_2$O diethylether
EDCl 1-ethyl-3-(3-dimethylaminoprobyl)carbodiimide)
POCl$_3$ Phosphoryl chloride
TFA 2,2,2-Trifluoroethanoic add
K$_2$CO$_3$ potassium carbonate
Na$_2$S.9H$_2$O Sodium Sulfide Nonahydride

EXAMPLE 1

Intermediate 1

5-chloro-3-nitropyridine-2-thiol

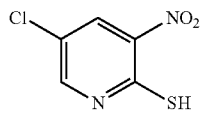 [SMILES: O=[N+]([O-])c1cc(Cl)cnc1S]

To a solution of 2,5-dichloro-3-nitropyridine (524 mg, 2.70 mmol) in dioxane (5 ml) and water (1 ml) was added Na$_2$S.9H$_2$O and the reaction was stirred at rt for 2 hours. The reaction was quenched with 1N HCl and then extracted with EtOAc (2×30 ml). The organic layer was washed with water, brine and dried over Na$_2$SO$_4$ anhydride and concentrated in vacuo. The crude residue was purified by silica gel column chromatography (30% EtOAc in Hexane) to give Intermediate 1 (378 mg, 74%).

$^1$H NMR (600 MHz, CDCl$_3$) δ 8.54 (d, J=2.05 Hz, 1H), 8.51 (d, J=2.05 Hz, 1H).

EXAMPLE 2

Intermediate 2

2-(benzylthio)-5-chloro-3-nitropyridine

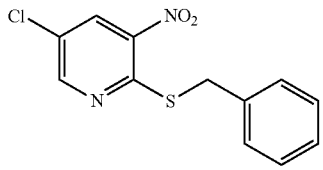 [SMILES: O=[N+]([O-])c1cc(Cl)cnc1SCc1ccccc1]

A mixture of Intermediate 1 (332 mg, 1.74 mmol), (bromomethyl)benzene (299 mg, 1.74 mmol) and K$_2$CO$_3$ (1.2 g, 8.74 mmol) in DMF (10 ml) was stirred at room temperature over night. The reaction mixture was poured into water (50 ml) and extracted with ethyl acetate (2×50 ml). The organic layer was washed with brine and then dried over Na$_2$SO$_4$ anhydride, concentrated in vacuo and purified by column chromatography (0~30% ethyl acetate in hexane) to give Intermediate 2 (417 mg, 85%).

$^1$H NMR (600 MHz, acetone) δ 8.88 (d, J=2.35 Hz, 1H), 8.65 (d, J=2.05 Hz, 1H), 7.41-7.52 (m, 2H), 7.29-7.34 (m, 2H), 7.23-7.28 (m, 1H), 4.50 (s, 2H).

EXAMPLE 3

Intermediate 3

2-(benzylthio)-5-chloropyridin-3-amine

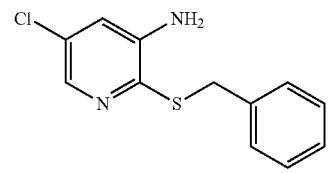 [SMILES: Nc1cc(Cl)cnc1SCc1ccccc1]

Intermediate 2 (417 mg, 1.49 mmol) was dissolved in MeOH (30 ml). Zn (2.4 g, 37.23 mmol) and NH$_4$Cl (1 ml) was added to the solution. After the mixture was stirred for 10 min at room temperature, the solid was filtered and the filtrate was concentrated in vacuo and then the crude residue was purified by column chromatography (0~30% EtOAc in hexane) to afford Intermediate 3 (326 mg, 88%).

$^1$H NMR (600 MHz, acetone) δ 7.82 (d, J=2.05 Hz, 1H), 7.40 (d, J=7.63 Hz, 2H), 7.28 (t, J=7.48 Hz, 2H), 7.18-7.24 (m, 1H), 7.03 (s, 1H), 4.44 (s, 2H).

EXAMPLE 4

Compound 1

N-[2-(benzylthio)-5-chloropyridin-3-yl]-1-benzofuran-2-sulfonamide

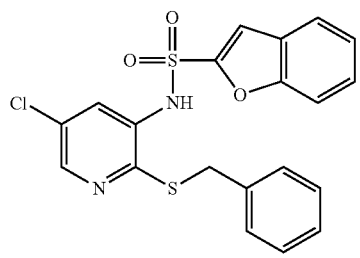 [SMILES: O=S(=O)(Nc1cc(Cl)cnc1SCc1ccccc1)c1cc2ccccc2o1]

A mixture of Intermediate 3 (326 mg, 1.30 mmol) and benzofuran-2-sulfonyl chloride (281 mg, 1.30 mmol) in pyridine (3 ml) was heated at 100° C. overnight. Pyridine was removed by reduced pressure and the residue was loaded on silica gel column directly and isolated Compound 1 with 30% EtOAc in Hexane (277 mg, 50%).

$^1$H NMR (600 MHz, acetone) δ 9.25 (br. s., 1H), 8.40 (d, J=2.35 Hz, 1H), 7.71-7.79 (m, 2H), 7.50-7.61 (m, 2H), 7.44

(d, J=0.88 Hz, 1H), 7.38-7.42 (m, 1H), 7.12-7.19 (m, 3H), 6.98-7.07 (m, 2H), 4.18 (s, 2H).

EXAMPLE 5

Compound 2

N-[2-(benzylsulfinyl)-5-chloropyridin-3-yl]-1-benzofuran-2-sulfonamide

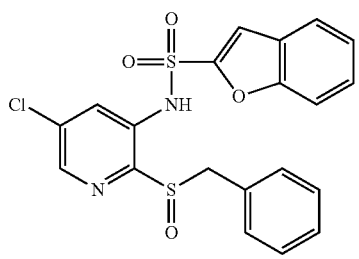 [SMILES: O=S(Cc1ccccc1)c1ncc(Cl)cc1NS(=O)(=O)c1cc2ccccc2o1]

To a solution of Compound 1 (219 mg, 0.509 mmol) in CH$_2$Cl$_2$ (10 ml) at 0° C. was added mCPBA (102 mg, 0.509 mmol). After it was stirred for 30 min at 0° C., the mixture was separated into two portions. One portion (5 ml) was concentrated in vacuo and purified by silica gel column chromatography (0~100% EtOAc in hexane followed by 0~10% MeOH in CH$_2$Cl$_2$) to give Compound 2 as a solid (92 mg).

$^1$H NMR (300 MHz, CD$_3$OD) δ 7.88 (s, 1H), 7.81 (br. s., 1H), 7.62-7.71 (m, 1H), 7.03-7.45 (m, 9H), 4.52 (d, J=12.89 Hz, 1H), 4.25 (d, J=12.89 Hz, 1H).

EXAMPLE 6

Compound 3

N-[2-(benzylsulfonyl)-5-chloropyridin-3-yl]-1-benzofuran-2-sulfonamide

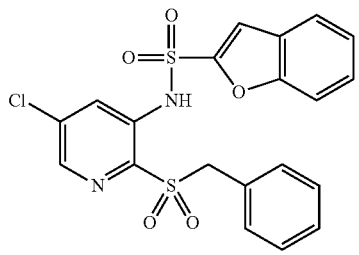 [SMILES: O=S(=O)(Cc1ccccc1)c1ncc(Cl)cc1NS(=O)(=O)c1cc2ccccc2o1]

To the other portion (5 ml) of the reaction from EXAMPLE 5 was added mCPBA (110 mg, 0.548 mmol) and the reaction was stirred at rt for 2 hours. The mixture was concentrated in vacuo and the residue was purified by column chromatography on silica gel (0~100% EtOAc in hexane) to give Compound 3 as a solid (63 mg).

$^1$H NMR (600 MHz, CD$_3$OD) δ 8.18 (d, J=2.05 Hz, 1H), 7.63-7.72 (m, 2H), 7.32-7.45 (m, 3H), 7.23-7.30 (m, 1H), 7.08-7.15 (m, 3H), 6.95-7.04 (m, 2H), 4.83 (s, 2H).

EXAMPLE 7

Intermediate 4

5-chloro-3-nitro-2-((pyridin-3-ylmethyl)thio)pyridine

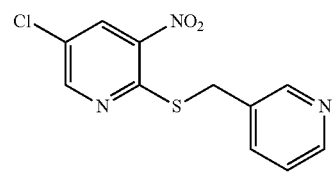 [SMILES: O=[N+]([O-])c1cc(Cl)cnc1SCc1cccnc1]

To a solution of Intermediate 1 (416 mg, 2.19 mmol) in DMF (10 ml) was added 3-(bromomethyl)pyridine hydrobromide (554 mg, 2.19 mmol) and K$_2$CO$_3$ (1.5 g, 10.95 mmol) and stirred at room temperature for 1 hour. The reaction mixture was poured into water (50 ml) and extracted with ethyl acetate (2×50 ml). The organic layer was washed with brine and then dried over Na$_2$SO$_4$, concentrated in vacuo and purified by flash column chromatography on silica gel (0~30% ethyl acetate in hexane) to give Intermediate 4 (462 mg, 75%).

$^1$H NMR (600 MHz, CD$_3$OD) δ 8.80 (d, J=2.35 Hz, 1H), 8.65 (d, J=2.35 Hz, 1H), 8.64 (d, J=2.05 Hz, 1H), 8.39 (dd, J=1.32, 4.84 Hz, 1H), 7.94 (ddd, J=1.61, 1.91, 8.22 Hz, 1H), 7.37 (dd, J=5.14, 7.48 Hz, 1H), 4.52 (s, 2H).

EXAMPLE 8

Intermediate 5

5-chloro-2-((pyridin-3-ylmethyl)thio)pyridin-3-amine

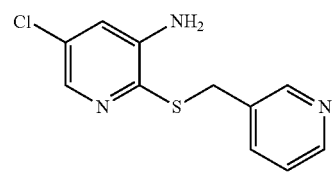 [SMILES: Nc1cc(Cl)cnc1SCc1cccnc1]

To a solution Intermediate 4 (460 mg, 1.64 mmol) in MeOH (20 ml) was added saturated aqueous NH$_4$Cl (2 ml) and zinc dust (2.7 g, 41.07 mmol). The suspension was stirred at room temperature for 1 hour and was filtered, the filtrate was extracted with EtOAc (×2). The organic layer was washed with brine, dried over Na$_2$SO$_4$, and concentrated in vacuo. The crude Intermediate 5 (314 mg, 76%) was used in the next reaction without further purification.

¹H NMR (600 MHz, CD₃OD) δ 8.47 (d, J=1.76 Hz, 1H), 8.35 (dd, J=1.47, 4.99 Hz, 1H), 7.81 (dt, J=1.91, 7.92 Hz, 1H), 7.77 (d, J=2.05 Hz, 1H), 7.23-7.41 (m, 1H), 6.98 (d, J=2.35 Hz, 1H), 4.38 (s, 2H).

EXAMPLE 9

Compound 4

N-{5-chloro-2-[(pyridin-3-ylmethyl)thio]pyridin-3-yl}-1-benzofuran-2-sulfonamide

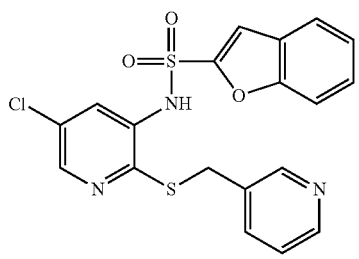 [SMILES: O=S(=O)(Nc1cc(Cl)cnc1SCc1cccnc1)c1cc2ccccc2o1]

To Intermediate 5 (310 mg, 1.24 mmol) in pyridine (5 ml) was added benzofuran-2-sulfonyl chloride (268 mg, 1.24 mmol) and the reaction was stirred at 100° C. for 16 hours, then additional benzofuran-2-sulfonyl chloride (268 mg, 1.24 mmol) was added and the mixture was heated for another 24 hours and concentrated in vacuo. The crude product was purified by flash column chromatography on silica gel (0-30% EtOAc in hexanes) to yield Compound 4 (201 mg, 38%).

¹H NMR (600 MHz, CD₃OD) δ 8.47 (s, 1H), 8.29 (d, J=4.70 Hz, 1H), 7.87 (d, J=1.47 Hz, 1H), 7.66 (d, J=7.63 Hz, 1H), 7.59 (d, J=7.63 Hz, 1H), 7.50 (d, J=2.35 Hz, 1H), 7.46 (d, J=8.22 Hz, 1H), 7.36 (td, J=1.03, 7.85 Hz, 1H), 7.17-7.29 (m, 2H), 7.08 (s, 1H), 4.23 (s, 2H).

EXAMPLE 10

Compound 5

N-{5-chloro-2-[(pyridin-3-ylmethyl)sulfinyl]pyridin-3-yl}-1-benzofuran-2-sulfonamide

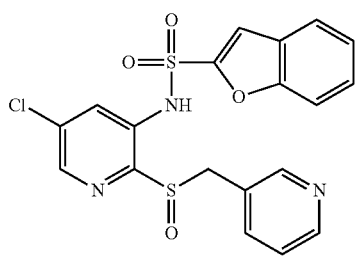 [SMILES: O=S(Cc1cccnc1)c1ncc(Cl)cc1NS(=O)(=O)c1cc2ccccc2o1]

To a solution of Compound 4 (77 mg, 0.18 mmol) in CH₂Cl₂ (10 ml) at 0° C. was added mCPBA (36 mg, 0.18 mmol). After it was stirred for 30 min at 0° C., the mixture was concentrated in vacuo and purified by silica gel column chromatography (0~100% EtOAc in hexane followed by 0~10% MeOH in CH₂Cl₂) to give Compound 5 (50 mg, 62%).

¹H NMR (600 MHz, CD₃OD) δ 8.32 (dd, J=1.17, 4.99 Hz, 1H), 8.05 (d, J=1.47 Hz, 1H), 7.87 (d, J=1.47 Hz, 1H), 7.76 (d, J=1.76 Hz, 1H), 7.68 (d, J=7.63 Hz, 1H), 7.39-7.45 (m, 2H), 7.30-7.37 (m, 2H), 7.24-7.29 (m, J=7.63 Hz, 1H), 7.18 (dd, J=4.99, 7.63 Hz, 1H), 4.59 (d, J=13.21 Hz, 2H), 4.45 (d, J=13.50 Hz, 1H).

EXAMPLE 11

Compound 6

N-{5-chloro-2-[(pyridin-3-ylmethyl)sulfonyl]pyridin-3-yl}-1-benzofuran-2-sulfonamide

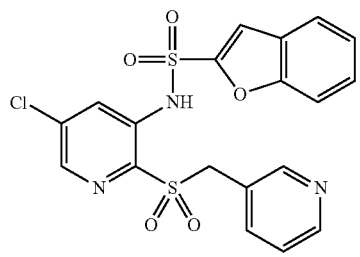 [SMILES: O=S(=O)(Cc1cccnc1)c1ncc(Cl)cc1NS(=O)(=O)c1cc2ccccc2o1]

and

Compound 7

N-(5-chloro-2-{[(1-oxidopyridin-3-yl)methyl]sulfonyl}pyridin-3-yl)-1-benzofuran-2-sulfonamide

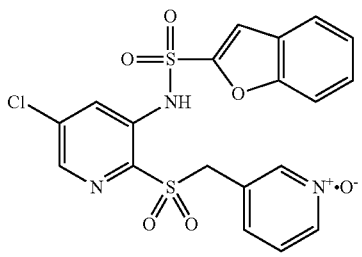

To a solution of Compound 4 (79 mg, 0.18 mmol) in CH₂Cl₂ (10 ml) was added mCPBA (92 mg, 0.46 mmol), and the solution was stirred at room temperature for 2 hours. It was concentrated in vacuo and purified by silica gel column chromatography (0~100% EtOAC in hexane followed by 0~10% MeOH in CH₂Cl₂) to isolate Compound 6 (11 mg) and Compound 7 (15 mg).

Compound 6: ¹H NMR (600 MHz, CD₃OD) δ 8.44 (d, J=1.47 Hz, 1H), 8.35 (dd, J=1.17, 4.99 Hz, 1H), 8.14 (d, J=2.05 Hz, 1H), 7.72 (d, J=2.05 Hz, 1H), 7.68 (d, J=7.92 Hz, 2H), 7.45 (d, J=8.22 Hz, 1H), 7.33-7.40 (m, 2H), 7.23-7.32 (m, 1H), 7.17 (dd, J=4.99, 7.92 Hz, 1H), 5.15 (s, 2H).

Compound 7: ¹H NMR (600 MHz, CD₃OD) δ 8.40 (s, 1H), 8.19 (d, J=6.46 Hz, 1H), 8.13 (d, J=2.05 Hz, 1H), 7.86 (s, 1H), 7.68 (d, J=7.34 Hz, 1H), 7.50 (d, J=8.51 Hz, 1H), 7.46 (d, J=7.92 Hz, 1H), 7.34-7.42 (m, 2H), 7.26-7.33 (m, 2H), 5.15 (s, 2H).

EXAMPLE 12

Intermediate 6

2-(benzylthio)-3-nitropyridine

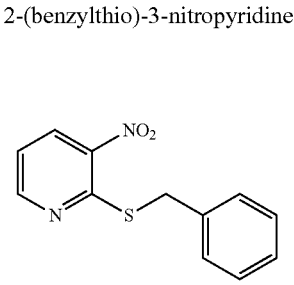

To a solution of 3-nitropyridine-2-thiol (1.0 g, 6.41 mmol) in DMF (30 ml) was added (bromomethyl)benzene (1.10 g, 6.41 mmol) and K₂CO₃ (4.4 g, 32.05 mmol), and the reaction was stirred at room temperature for 1 hour. The reaction mixture was poured into water (50 ml) and extracted with ethyl acetate (2×50 ml). The organic layer was washed with brine and then dried over Na₂SO₄, concentrated in vacuo and purified by flash column chromatography on silica gel (0~30% ethyl acetate in hexane) to give Intermediate 6 (1.49 g, 94%).

¹H NMR (600 MHz, CD₃OD) δ 8.70-8.79 (m, 1H), 8.55 (dd, J=1.17, 8.22 Hz, 1H), 7.39-7.44 (m, 2H), 7.33 (dd, J=4.55, 8.36 Hz, 1H), 7.29 (t, J=7.63 Hz, 2H), 7.19-7.25 (m, 1H), 4.48 (s, 3H).

EXAMPLE 13

Intermediate 7

2-(benzylthio)pyridin-3-amine

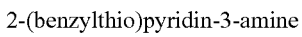

To a solution Intermediate 6 (1.49 g, 6.06 mmol) in MeOH (100 ml) was added saturated aqueous NH₄Cl (4 ml) and zinc dust (7.8 g, 121.1 mmol). The suspension was stirred at room temperature for 1 hour and was filtered, and the filtrate was extracted with EtOAc (×2). The organic layer was washed with brine, dried over Na₂SO₄, and concentrated in vacuo. The crude Intermediate 7 (1 g, 76%) was used in the next reaction without further purification.

¹H NMR (600 MHz, CD₃OD) δ 7.80-7.84 (m, 1H), 7.25-7.30 (m, 2H), 7.20-7.24 (m, 2H), 7.15-7.19 (m, 1H), 6.95-7.02 (m, 2H), 4.30 (s, 2H).

EXAMPLE 14

Compound 8

N-[2-(benzylthio)pyridin-3-yl]-1-benzofuran-2-sulfonamide

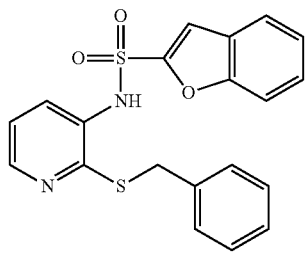 [SMILES: O=S(=O)(Nc1cccnc1SCc1ccccc1)c1cc2ccccc2o1]

To Intermediate 7 (553 mg, 2.56 mmol) in pyridine (5 ml) was added benzofuran-2-sulfonyl chloride (553 mg, 2.56 mmol), and the reaction was stirred at 100° C. for 16 hours, then additional benzofuran-2-sulfonyl chloride (553 mg, 2.56 mmol) was added, and the reaction was heated for another 24 hours, and the mixture was concentrated in vacuo. The crude product was purified by flash column chromatography on silica gel (0-30% EtOAc in hexanes) to yield Compound 8 (800 mg, 79%).

¹H NMR (600 MHz, CD₃OD) δ 8.29 (dd, J=1.61, 4.84 Hz, 1H), 7.65 (d, J=7.92 Hz, 1H), 7.60 (dd, J=1.61, 7.78 Hz, 1H), 7.41-7.51 (m, 2H), 7.33 (ddd, J=2.20, 5.94, 8.00 Hz, 1H), 7.24 (s, 1H), 7.01-7.14 (m, 4H), 6.92 (dd, J=1.47, 7.63 Hz, 2H), 4.11 (s, 2H).

EXAMPLE 15

Compound 9

N-[2-(benzylsulfinyl)pyridin-3-yl]-1-benzofuran-2-sulfonamide

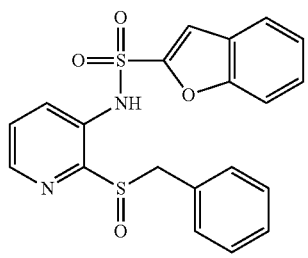 [SMILES: O=S(Cc1ccccc1)c1ncccc1NS(=O)(=O)c1cc2ccccc2o1]

To a solution of Compound 8 (228 mg, 0.58 mmol) in CH₂Cl₂ (10 ml) at 0° C. was added mCPBA (116 mg, 0.58 mmol). After it was stirred for 30 min at 0° C., the mixture was separated into two portions. One portion (5 ml) was concentrated in vacuo and purified by silica gel column chromatography (0~100% EtOAC in hexane followed by 0~10% MeOH in CH₂Cl₂) to give Compound 9 (205 mg, 86%).

¹H NMR (600 MHz, CD₃OD) δ 8.42 (dd, J=1.03, 4.55 Hz, 1H), 7.86 (dd, J=1.03, 8.36 Hz, 1H), 7.73 (d, J=9.10 Hz, 1H), 7.56 (d, J=8.51 Hz, 1H), 7.47-7.52 (m, 2H), 7.44-7.47 (m, 1H), 7.32-7.38 (m, 1H), 7.11-7.22 (m, 3H), 7.05 (d, J=7.04 Hz, 2H), 4.34 (d, J=12.91, 1H), 4.25 (d, J=13.21, 1H).

EXAMPLE 16

Compound 10

N-[2-(benzylsulfonyl)pyridin-3-yl]-1-benzofuran-2-sulfonamide

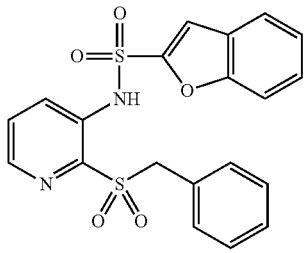 [SMILES: O=S(=O)(Cc1ccccc1)c1ncccc1NS(=O)(=O)c1cc2ccccc2o1]

To a solution of Compound 8 (360 mg, 0.91 mmol) in CH₂Cl₂ (10 ml) at room temperature was added mCPBA (365 mg, 1.82 mmol). After it was stirred for 2 hours at room temperature, the mixture was concentrated in vacuo and purified by silica gel column chromatography (0~100% EtOAc in hexane) to give Compound 10 (124 mg, 32%).

¹H NMR (600 MHz, CD₃OD) δ 8.13 (dd, J=1.03, 8.95 Hz, 1H), 7.74 (dd, J=0.73, 4.26 Hz, 1H), 7.66 (d, J=7.34 Hz, 1H), 7.38-7.43 (m, 1H), 7.32-7.37 (m, 2H), 7.23-7.31 (m, 2H), 7.08-7.17 (m, 3H), 6.95-7.05 (m, 2H), 5.06 (s, 2H).

EXAMPLE 17

Intermediate 8 tert-butyl (3-(((3-nitropyridin-2-yl)thio)methyl)phenyl)carbamate

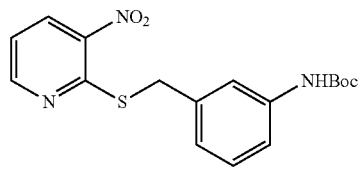 [SMILES: CC(C)(C)OC(=O)Nc1cccc(CSc2ncccc2[N+](=O)[O-])c1]

To 3-nitropyridine-2-thiol (532 mg, 3.41 mmol) in DMF (10 ml) was added tert-butyl (3-(bromomethyl)phenyl)carbamate (976 mg, 3.41 mmol) and K₂CO₃ (2.35 g, 17.05 mmol) and the reaction was stirred at room temperature for 2 hours. The reaction mixture was poured into water (50 ml) and extracted with ethyl acetate (2×50 ml). The organic layer was washed with brine and then dried over Na₂SO₄, concentrated in vacuo and purified by flash column chromatography on silica gel (0~30% ethyl acetate in hexane) to give Intermediate 8 (1.22 g, 100%).

¹H NMR (600 MHz, CD₃OD) δ 8.76 (d, J=4.70 Hz, 1H), 8.55 (d, J=8.22 Hz, 1H), 7.50 (s, 1H), 7.33 (ddd, J=1.17, 4.70, 8.22 Hz, 1H), 7.27 (d, J=7.92 Hz, 1H), 7.14-7.22 (m, 1H), 7.06 (d, J=7.63 Hz, 1H), 4.45 (s, 2H), 1.51 (s, 9H).

EXAMPLE 18

Intermediate 9 tert-butyl (3-(((3-aminopyridin-2-yl)thio)methyl)phenyl)carbamate

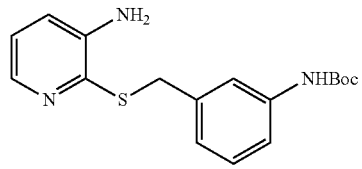 [SMILES: CC(C)(C)OC(=O)Nc1cccc(CSc2ncccc2N)c1]

To Intermediate 8 (1.18 g, 3.27 mmol) in MeOH (50 ml) and CH₂Cl₂ (5 ml) was added saturated aqueous NH₄Cl (3 ml) and zinc dust (5.3 g, 81.72 mmol). The suspension was stirred at room temperature for 1 hour and was filtered, the filtrate was extracted with EtOAc (×2). The organic layer was washed with brine, dried over Na₂SO₄, and concentrated in vacuo. The crude Intermediate 9 (908 mg, 84%) was used in the next reaction without further purification.

¹H NMR (600 MHz, acetone) δ 7.86 (d, J=4.40 Hz, 1H), 7.59-7.67 (m, 1H), 7.41 (d, J=7.92 Hz, 1H), 7.17 (t, J=7.78 Hz, 1H), 7.03 (d, J=7.34 Hz, 1H), 6.97 (d, J=7.63 Hz, 1H), 6.89 (dd, J=4.70, 7.92 Hz, 1H), 4.59 (br. s., 2H), 4.44 (s, 2H), 1.46 (s, 9H).

EXAMPLE 19

Intermediate 10

{3-[3-(benzofuran-2-sulfonylamino)-pyridin-2-ylsulfanylmethyl]-phenyl}-carbamic acid tert-butyl Ester

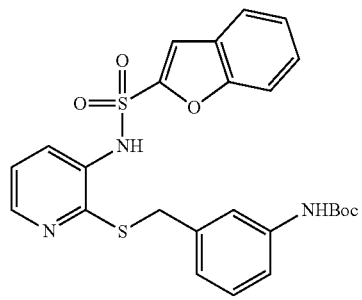 [SMILES: CC(C)(C)OC(=O)Nc1cccc(CSc2ncccc2NS(=O)(=O)c2cc3ccccc3o2)c1]

and

Compound 11

N-{2-[(3-aminobenzyl)sulfanyl]pyridin-3-yl}-1-benzofuran-2-sulfonamide

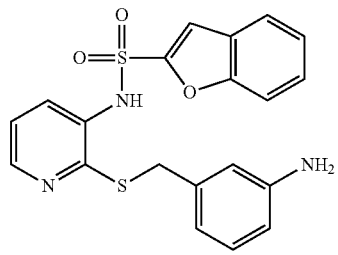 [SMILES: Nc1cccc(CSc2ncccc2NS(=O)(=O)c2cc3ccccc3o2)c1]

To Intermediate 9 (908 mg, 2.74 mmol) in pyridine (5 ml) was added benzofuran-2-sulfonyl chloride (592 mg, 2.74 mmol) and the reaction was stirred at 100° C. for 16 hours, then additional benzofuran-2-sulfonyl chloride (592 mg, 2.74 mmol) was added and the mixture was further heated for 24 hours and concentrated in vacuo. The crude product was purified by flash column chromatography on silica gel (0-40% EtOAc in hexanes) to yield Intermediate 10 (760 mg, 54%) and Compound 11 (129 mg, 11%).

Intermediate 10 $^1$H NMR (600 MHz, CD$_3$OD) δ 8.33 (dd, J=1.17, 4.70 Hz, 1H), 7.66 (d, J=7.63 Hz, 1H), 7.60 (dd, J=1.61, 7.78 Hz, 1H), 7.46-7.51 (m, 2H), 7.30-7.38 (m, 1H), 7.25 (s, 1H), 7.16-7.22 (m, 2H), 7.09 (dd, J=4.70, 7.92 Hz, 1H), 7.00 (t, J=8.22 Hz, 1H), 6.57 (d, J=7.63 Hz, 1H), 4.10 (s, 2H), 1.52 (s, 9H).

Compound 11 $^1$H NMR (600 MHz, acetone) δ 8.37 (dd, J=1.47, 4.70 Hz, 1H), 7.75 (d, J=7.92 Hz, 1H), 7.48-7.68 (m, 3H), 7.30-7.44 (m, 2H), 7.12 (dd, J=4.70, 7.92 Hz, 1H), 6.87 (t, J=7.63 Hz, 1H), 6.41-6.57 (m, 2H), 6.31 (d, J=7.63 Hz, 1H), 4.09 (s, 2H).

EXAMPLE 20

Intermediate 11

{3-[3-(benzofuran-2-sulfonylamino)-pyridine-2-sulfinylmethyl]-phenyl}-carbamic acid tert-butyl ester

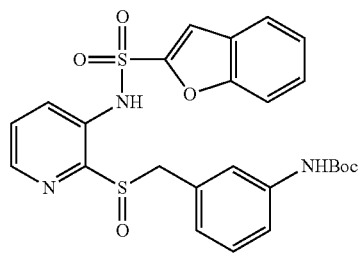 [SMILES: CC(C)(C)OC(=O)Nc1cccc(CS(=O)c2ncccc2NS(=O)(=O)c2cc3ccccc3o2)c1]

To a solution of Intermediate 10 (294 mg, 0.58 mmol) in CH$_2$Cl$_2$ (5 ml) was added mCPBA (115 mg, 0.58 mmol) and the reaction was stirred at 0° C. for 30 mins and was concentrated. The residue was purified by flash column chromatography on silica gel (100% EtOAc) to yield Intermediate 11 (242 mg, 80%).

$^1$H NMR (600 MHz, CD$_3$OD) δ 8.84 (br. s., 1H), 8.43 (dd, J=1.17, 4.40 Hz, 1H), 7.85 (dd, J=1.03, 8.07 Hz, 1H), 7.73 (d, J=7.92 Hz, 1H), 7.57 (d, J=8.51 Hz, 1H), 7.47-7.52 (m, 2H), 7.45 (dd, J=4.55, 8.36 Hz, 1H), 7.35 (t, J=7.63 Hz, 1H), 7.26 (d, J=7.92 Hz, 1H), 7.22 (s, 1H), 7.10 (t, J=7.78 Hz, 1H), 6.70 (d, J=7.63 Hz, 1H), 4.27-4.33 (d, J=12.91 Hz, 1H), 4.18-4.23 (d, J=12.91 Hz, 1H), 1.51 (s, 9H).

EXAMPLE 21

Compound 12

N-{2-[(3-aminobenzyl)sulfinyl]pyridin-3-yl}-1-benzofuran-2-sulfonamide

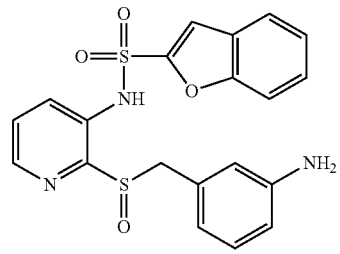 [SMILES: Nc1cccc(CS(=O)c2ncccc2NS(=O)(=O)c2cc3ccccc3o2)c1]

Intermediate 11 (240 mg, 0.455 mmol), TFA (1 ml) in CH$_2$Cl$_2$ (5 ml) was stirred overnight. The solvent was removed and the crude was purified by column chromatography (50% ethyl acetate in hexanes) to afford Compound 12 (186 mg, 96%).

$^1$H NMR (600 MHz, CD$_3$OD) δ 8.41 (dd, J=1.32, 4.55 Hz, 1H), 7.82 (dd, J=1.17, 8.51 Hz, 1H), 7.71 (d, J=7.92 Hz, 1H), 7.41-7.57 (m, 4H), 7.33 (t, J=7.48 Hz, 1H), 7.14 (t, J=7.78 Hz, 1H), 6.93 (dd, J=1.47, 7.92 Hz, 1H), 6.90 (s, 1H), 6.72 (d, J=7.63 Hz, 1H), 4.33 (d, J=13.21 Hz, 1H), 4.23 (d, J=13.21 Hz, 1H).

EXAMPLE 22

Compound 13 tert-butyl {3-[({3-[(1-benzofuran-2-ylsulfonyl)amino]pyridin-2-yl}sulfonyl)methyl]phenyl}carbamate

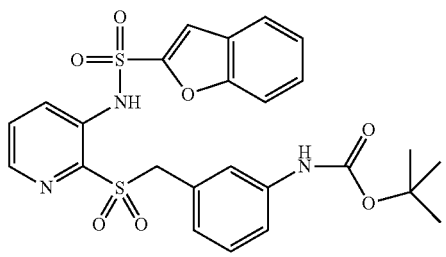 [SMILES: CC(C)(C)OC(=O)Nc1cccc(CS(=O)(=O)c2ncccc2NS(=O)(=O)c2cc3ccccc3o2)c1]

To a solution of Intermediate 10 (418 mg, 0.82 mmol) in CH$_2$Cl$_2$ (10 ml) was added mCPBA (426 mg, 2.13 mmol) and the reaction was stirred at room temperature for 3 hours and was concentrated. The residue was purified by flash column chromatography on silica gel (100% EtOAc) to yield Compound 13 (340 mg, 76%).

$^1$H NMR (600 MHz, CD$_3$OD) δ 8.80 (br. s., 1H), 8.46 (br. s., 1H), 8.15 (dd, J=1.32, 8.66 Hz, 1H), 7.73 (d, J=7.92 Hz, 1H), 7.61 (dd, J=4.40, 8.22 Hz, 1H), 7.44-7.57 (m, 3H), 7.35

(t, J=7.63 Hz, 1H), 7.25 (s, 1H), 7.14 (d, J=7.04 Hz, 1H), 7.00 (t, J=7.92 Hz, 1H), 6.70 (d, J=7.63 Hz, 1H), 4.65 (br. s., 2H), 1.50 (s, 9H).

EXAMPLE 23

Compound 14

N-{2-[(3-aminobenzyl)sulfonyl]pyridin-3-yl}-1-benzofuran-2-sulfonamide

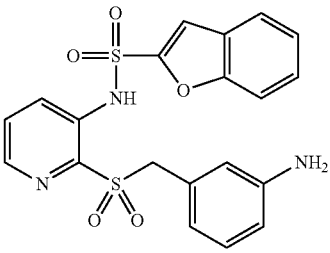 [SMILES: Nc1cccc(CS(=O)(=O)c2ncccc2NS(=O)(=O)c2cc3ccccc3o2)c1]

Compound 13 (287 mg, 0.53 mmol), TFA (1 ml) in CH$_2$Cl$_2$ (5 ml) was stirred overnight. The solvent was removed and the crude was purified by column chromatography (50% ethyl acetate) to afford Compound 14 (214 mg, 91%). $^1$H NMR (600 MHz, CD$_3$OD) δ 8.46 (d, J=4.40 Hz, 1H), 8.18 (d, J=8.80 Hz, 1H), 7.74 (d, J=7.92 Hz, 1H), 7.60-7.67 (m, 1H), 7.54-7.59 (m, 2H), 7.47-7.53 (m, 1H), 7.36 (t, J=7.48 Hz, 1H), 6.85-6.96 (m, 1H), 6.55-6.71 (m, 2H), 6.42-6.53 (m, 1H), 4.61 (d, J=3.81 Hz, 2H).

EXAMPLE 24

Intermediate 12

2-chloro-5-fluoro-3-nitropyridine

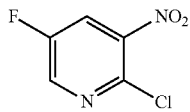

To a solution of 5-fluoro-3-nitro-pyridin-2-ol (2.0 g, 12.65 mmol), benzyltrimethylammonium chloride (1.2 g, 6.33 mmol) in CH$_3$CN (20 ml) was added POCl$_3$ (5 ml) and the mixture was heated at 80° C. overnight. Another 2 ml POCl$_3$ was added to the mixture and the reaction was heated at 80° C. for another 2 hours more. The reaction mixture was quenched with water and extracted with EtOAc. The organic layer was washed with brine, dried over Na$_2$SO$_4$ anhydrous and concentrated in vacuo. The residue was purified by silica gel column chromatography (0~30% EtOAc in hexane) to give Intermediate 12 (1.3 g, 59%).

$^1$H NMR (600 MHz, CDCl$_3$) δ 8.55 (d, J=2.64 Hz, 1H), 8.03 (dd, J=2.79, 6.60 Hz, 1H).

EXAMPLE 25

Intermediate 13

5-fluoro-3-nitropyridine-2-thiol

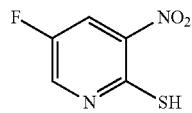

To a solution of Intermediate 12 (460 mg, 2.61 mmol) in dioxane (5 ml) and water (1 ml) was added Na$_2$S.9H$_2$O and the reaction was stirred at rt for 5 hours. The reaction was quenched with 1N HCl and then extracted with EtOAc (2×30 ml). The organic layer was washed with water, brine and dried over Na$_2$SO$_4$ and concentrated in vacuo. The crude product was used in the next reaction without further purification.

EXAMPLE 26

Intermediate 14

2-(benzylthio)-5-fluoro-3-nitropyridine

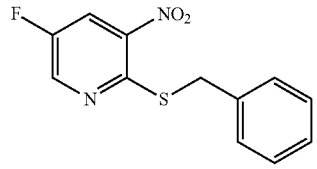 [SMILES: O=[N+]([O-])c1cc(F)cnc1SCc1ccccc1]

To the crude Intermediate 13 in DMF (10 ml) was added (bromomethyl)benzene (477 mg, 2.61 mmol) and K$_2$CO$_3$ (1.8 g, 13.07 mmol) and the reaction was stirred at room temperature for 16 hours. The reaction mixture was poured into water (50 ml) and extracted with ethyl acetate (2×50 ml). The organic layer was washed with brine and then dried over Na$_2$SO$_4$, concentrated in vacuo and purified by flash column chromatography on silica gel (0~30% ethyl acetate in hexane) to give Intermediate 14 (420 mg, 22%).

$^1$H NMR (600 MHz, CDCl$_3$) δ 8.66 (d, J=2.64 Hz, 1H), 8.27 (dd, J=2.64, 7.63 Hz, 1H), 7.41 (d, J=7.63 Hz, 2H), 7.31 (t, J=7.48 Hz, 2H), 7.22-7.28 (m, 1H), 4.45 (s, 2H).

EXAMPLE 27

Intermediate 15

2-(benzylthio)-5-fluoropyridin-3-amine

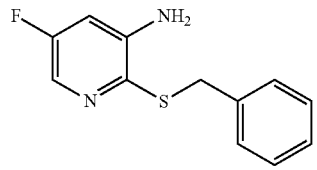 [SMILES: Nc1cc(F)cnc1SCc1ccccc1]

To a solution Intermediate 14 (420 mg, 1.60 mmol) in MeOH (20 ml) was added saturated aqueous NH$_4$Cl (2 ml) and zinc dust (2.5 g, 40 mmol). The suspension was stirred at room temperature for 1 hour and was filtered, and the filtrate was extracted with EtOAc (×2). The organic layer was washed with brine, dried over Na$_2$SO$_4$, and concentrated in vacuo. The crude Intermediate 15 (288 mg, 77%) was used in the next reaction without further purification.

$^1$H NMR (600 MHz, CD$_3$OD) δ 7.69 (d, J=2.35 Hz, 1H), 7.11-7.30 (m, 5H), 6.77 (dd, J=2.64, 10.27 Hz, 1H), 4.25 (s, 2H).

EXAMPLE 28

Compound 15

N-[2-(benzylsulfanyl)-5-fluoropyridin-3-yl]-1-benzofuran-2-sulfonamide

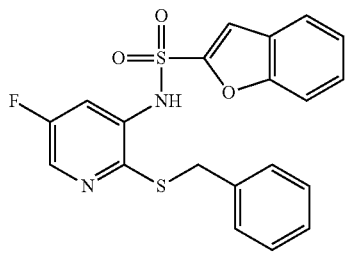 [SMILES: O=S(=O)(Nc1cc(F)cnc1SCc1ccccc1)c1cc2ccccc2o1]

To Intermediate 15 (285 mg, 1.22 mmol) in pyridine (5 ml) was added benzofuran-2-sulfonyl chloride (264 mg, 1.82 mmol) and the reaction was stirred at 100° C. for 16 hours, then additional benzofuran-2-sulfonyl chloride (264 mg, 1.82 mmol) was added and the reaction was further heated for 3 hours and concentrated in vacuo. The crude product was purified by flash column chromatography on silica gel (0-30% EtOAc in hexanes) to yield Compound 15 (379 mg, 75%).

$^1$H NMR (600 MHz, CD$_3$OD) δ 8.29 (d, J=2.64 Hz, 1H), 7.71 (d, J=7.92 Hz, 1H), 7.45-7.58 (m, 3H), 7.38 (ddd, J=2.93, 4.99, 7.92 Hz, 1H), 7.32 (s, 1H), 7.04-7.15 (m, 3H), 6.93 (dd, J=1.32, 7.48 Hz, 2H), 4.10 (s, 2H).

EXAMPLE 29

Compound 16

N-[2-(benzylsulfinyl)-5-fluoropyridin-3-yl]-1-benzofuran-2-sulfonamide

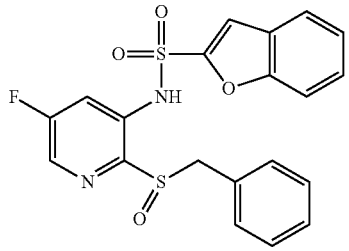 [SMILES: O=S(Cc1ccccc1)c1ncc(F)cc1NS(=O)(=O)c1cc2ccccc2o1]

To a solution of Compound 15 (110 mg, 0.27 mmol) in CH$_2$Cl$_2$ (5 ml) was added mCPBA (53 mg, 0.27 mmol) and the reaction was stirred at 0° C. for 30 min and was concentrated. The residue was purified by flash column chromatography on silica gel (100% EtOAc) to yield Compound 16 (170 mg, 72%).

$^1$H NMR (600 MHz, CD$_3$OD) δ 8.05 (br. s., 1H), 7.67-7.77 (m, 2H), 7.45-7.52 (m, 2H), 7.39-7.45 (m, 1H), 7.27-7.36 (m, 1H), 7.08-7.17 (m, 3H), 6.96-7.04 (m, 2H), 4.47 (d, J=12.91 Hz, 1H), 4.26 (d, J=13.21 Hz, 1H).

EXAMPLE 30

Compound 17

N-[2-(benzylsulfonyl)-5-fluoropyridin-3-yl]-1-benzofuran-2-sulfonamide

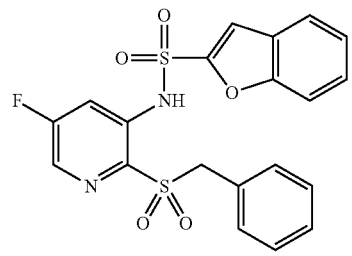 [SMILES: O=S(=O)(Cc1ccccc1)c1ncc(F)cc1NS(=O)(=O)c1cc2ccccc2o1]

To a solution of Compound 15 (167 mg, 0.40 mmol) in CH$_2$Cl$_2$ (5 ml) was added mCPBA (203 mg, 1.01 mmol) and the reaction was stirred at room temperature for 2 hours and was concentrated. The residue was purified by flash column chromatography on silica gel (100% EtOAc) to yield Compound 17 (127 mg, 71%).

$^1$H NMR (600 MHz, CD$_3$OD) δ 8.35 (d, J=2.35 Hz, 1H), 7.95 (dd, J=2.35, 10.56 Hz, 1H), 7.75 (d, J=7.92 Hz, 1H), 7.62 (d, J=0.88 Hz, 1H), 7.47-7.57 (m, 2H), 7.38 (td, J=1.17, 7.48 Hz, 1H), 7.05-7.14 (m, 4H), 6.98-7.03 (m, 1H), 4.71 (s, 2H).

EXAMPLE 31

Intermediate 16 tert-butyl (3-(((5-chloro-3-nitropyridin-2-yl)thio)methyl)phenyl)carbamate

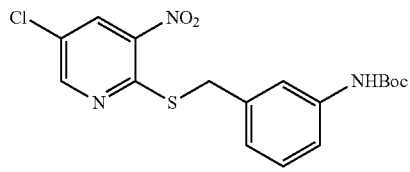

To Intermediate 1 (590 mg, 3.10 mmol) in DMF (10 ml) was added tert-butyl (3-(bromomethyl)phenyl)carbamate (889 mg, 2.61 mmol) and K$_2$CO$_3$ (2.1 g, 15.53 mmol) and the reaction was stirred at room temperature for 3 hours. The reaction mixture was poured into water (50 ml) and extracted with ethyl acetate (2×50 ml). The organic layer was washed with brine and then dried over Na$_2$SO$_4$, concentrated in vacuo and purified by flash column chromatography on silica gel (0~30% ethyl acetate in hexane) to give Intermediate 16 (1.06 g, 88%).

$^1$H NMR (600 MHz, acetone) δ 8.87 (d, J=2.05 Hz, 1H), 8.64 (d, J=2.35 Hz, 1H), 8.35 (br. s., 1H), 7.72 (s, 1H), 7.41 (d, J=8.22 Hz, 1H), 7.21 (t, J=7.92 Hz, 1H), 7.08 (d, J=7.63 Hz, 1H), 4.47 (s, 2H), 1.47 (s, 9H).

EXAMPLE 32

Intermediate 17 tert-butyl (3-(((3-amino-5-chloropyridin-2-yl)thio)methyl)phenyl)carbamate

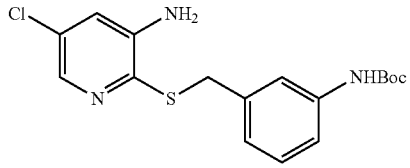 [SMILES: CC(C)(C)OC(=O)Nc1cccc(CSc2ncc(Cl)cc2[N+](=O)[O-])c1]

To a solution Intermediate 16 (1.06 g, 2.68 mmol) in MeOH (30 ml) was added saturated aqueous NH$_4$Cl (2 ml) and zinc dust (4.3 g, 67 mmol). The suspension was stirred at room temperature for 1 hour and was filtered, and the filtrate was extracted with EtOAc (×2). The organic layer was washed with brine, dried over Na$_2$SO$_4$, and concentrated in vacuo. The Intermediate 17 (581 mg, 59%) was used in the next reaction without further purification.

$^1$H NMR (600 MHz, CD$_3$OD) δ 7.74 (d, J=2.05 Hz, 1H), 7.38 (s, 1H), 7.22 (d, J=7.92 Hz, 1H), 7.08 (t, J=7.92 Hz, 1H), 6.92 (d, J=1.76 Hz, 1H), 6.89 (d, J=7.63 Hz, 1H), 4.23 (s, 2H), 1.46 (s, 9H).

EXAMPLE 33

Intermediate 18

{3-[3-(Benzofuran-2-sulfonylamino)-5-chloro-pyridin-2-ylsulfanylmethyl]-phenyl}-carbamic acid tert-butyl ester

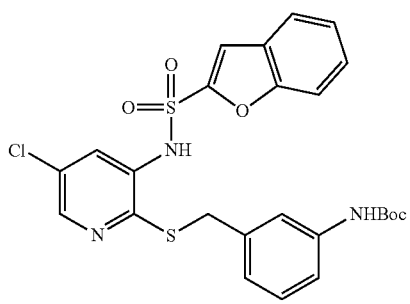 [SMILES: CC(C)(C)OC(=O)Nc1cccc(CSc2ncc(Cl)cc2NS(=O)(=O)c2cc3ccccc3o2)c1]

To Intermediate 17 (580 mg, 1.59 mmol) in pyridine (5 ml) was added benzofuran-2-sulfonyl chloride (242 mg, 1.82 mmol) and the reaction was stirred at 100° C. for 16 hours, then additional benzofuran-2-sulfonyl chloride (342 mg, 1.82 mmol) was added and the reaction was further heated for 24 hours and concentrated in vacuo. The crude Intermediate 18 was purified by flash column chromatography on silica gel (0-30% EtOAc in hexanes) to yield (359 mg, 41%).

$^1$H NMR (600 MHz, CD$_3$OD) δ 7.81-7.90 (m, 1H), 7.66 (d, J=7.63 Hz, 1H), 7.60 (dd, J=1.61, 7.78 Hz, 1H), 7.40-7.52 (m, 3H), 7.29-7.37 (m, 1H), 7.18 (s, 1H), 7.06-7.12 (m, 1H), 7.00 (t, J=8.22 Hz, 1H), 6.57 (d, J=7.63 Hz, 1H), 4.10 (s, 2H), 1.52 (s, 9H).

EXAMPLE 34

Compound 18

Benzofuran-2-sulfonic acid [2-(3-amino-benzylsulfanyl)-5-chloro-pyridin-3-yl]-amide

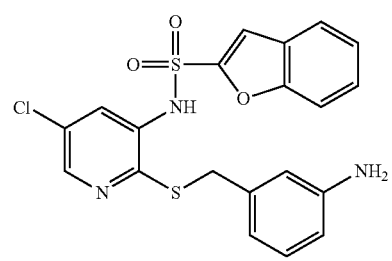 [SMILES: Nc1cccc(CSc2ncc(Cl)cc2NS(=O)(=O)c2cc3ccccc3o2)c1]

Intermediate 18 (50 mg, 0.092 mmol), TFA (0.5 ml) in CH$_2$Cl$_2$ (5 ml) was stirred for 2 hours. The solvent was removed and the crude was purified by flash column chromatography on silica gel (50% ethyl acetate) to afford Compound 18 (40 mg, 97%).

$^1$H NMR (600 MHz, CD$_3$OD) δ 8.34 (d, J=2.05 Hz, 1H), 7.69 (d, J=7.92 Hz, 1H), 7.61-7.65 (m, 1H), 7.46-7.56 (m, 2H), 7.36 (td, J=1.03, 7.26 Hz, 1H), 7.32 (s, 1H), 7.13 (t, J=7.92 Hz, 1H), 7.04 (s, 1H), 6.97 (dt, J=1.03, 7.92 Hz, 1H), 6.78 (d, J=7.63 Hz, 1H), 4.16 (s, 2H).

EXAMPLE 35

Intermediate 19

{3-[3-(benzofuran-2-sulfonylamino)-5-chloro-pyridine-2-sulfinylmethyl]-phenyl}-carbamic acid tert-butyl ester

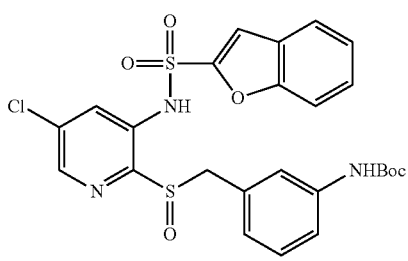 [SMILES: CC(C)(C)OC(=O)Nc1cccc(CS(=O)c2ncc(Cl)cc2NS(=O)(=O)c2cc3ccccc3o2)c1]

To a solution of Intermediate 18 (133 mg, 0.24 mmol) in CH$_2$Cl$_2$ (5 ml) was added mCPBA (49 mg, 0.24 mmol) and the reaction was stirred at 0° C. for 30 min and was concentrated. The residue was purified by flash column chromatography on silica gel (100% EtOAc) to yield Intermediate 19 (80 mg, 58%).

$^1$H NMR (600 MHz, CD$_3$OD) δ 7.91 (d, J=1.47 Hz, 2H), 7.68 (d, J=7.92 Hz, 1H), 7.42 (d, J=8.22 Hz, 1H), 7.32-7.39

(m, 2H), 7.17-7.31 (m, 3H), 7.00 (t, J=7.78 Hz, 1H), 6.66 (d, J=7.63 Hz, 1H), 4.55 (d, J=12.91 Hz, 1H), 4.23 (d, J=12.91 Hz, 1H), 1.47 (s, 9H).

EXAMPLE 36

Compound 19

N-{2-[(3-aminobenzyl)sulfinyl]-5-chloropyridin-3-yl}-1-benzofuran-2-sulfonamide

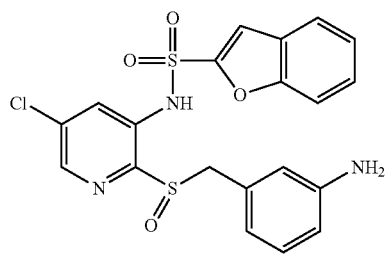 [SMILES: Nc1cccc(CS(=O)c2ncc(Cl)cc2NS(=O)(=O)c2cc3ccccc3o2)c1]

Intermediate 19 (80 mg, 0.15 mmol), TFA (0.5 ml) in CH$_2$Cl$_2$ (5 ml) was stirred for 2 hours. The solvent was removed and the crude was purified by flash column chromatography on silica gel (50% ethyl acetate) to afford Compound 19 (60 mg, 91%).

$^1$H NMR (600 MHz, CD$_3$OD) δ 8.23 (s, 1H), 7.86 (d, J=1.76 Hz, 1H), 7.72 (d, J=7.92 Hz, 1H), 7.48-7.53 (m, 2H), 7.41-7.47 (m, 1H), 7.28-7.37 (m, 1H), 7.17-7.25 (m, 1H), 7.03-7.11 (m, 2H), 6.85 (d, J=7.92 Hz, 1H), 4.43 (d, J=13.21 Hz, 1H), 4.27 (d, J=13.21 Hz, 1H).

EXAMPLE 37

Intermediate 20

{3-[3-(benzofuran-2-sulfonylamino)-5-chloro-pyridine-2-sulfonylmethyl]-phenyl}-carbamic acid tert-butyl ester

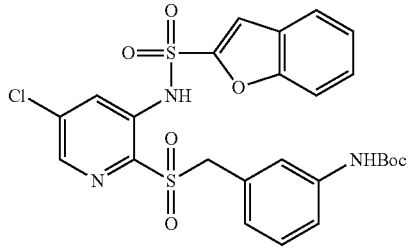 [SMILES: CC(C)(C)OC(=O)Nc1cccc(CS(=O)(=O)c2ncc(Cl)cc2NS(=O)(=O)c2cc3ccccc3o2)c1]

To a solution of Intermediate 19 (167 mg, 0.31 mmol) in CH$_2$Cl$_2$ (5 ml) was added mCPBA (153 mg, 0.77 mmol) and the reaction was stirred at room temperature for 3 hours and was concentrated. The residue was purified by flash column chromatography on silica gel (100% EtOAc) to yield Intermediate 20 (138 mg, 78%).

$^1$H NMR (600 MHz, CD$_3$OD) δ 8.45 (d, J=1.76 Hz, 1H), 8.12 (d, J=2.05 Hz, 1H), 7.72 (d, J=7.92 Hz, 1H), 7.56 (s, 1H), 7.44-7.53 (m, 2H), 7.29-7.38 (m, 1H), 7.20 (s, 1H), 6.95-7.06 (m, 2H), 6.77 (d, J=6.75 Hz, 1H), 4.63 (s, 2H), 1.48 (s, 9H).

EXAMPLE 38

Compound 20

N-(2-((3-aminobenzyl)sulfonyl)-5-chloropyridin-3-yl)benzofuran-2-sulfonamide

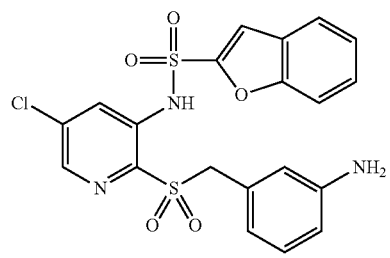 [SMILES: Nc1cccc(CS(=O)(=O)c2ncc(Cl)cc2NS(=O)(=O)c2cc3ccccc3o2)c1]

Intermediate 19 (138 mg, 0.24 mmol), TFA (0.5 ml) in CH$_2$Cl$_2$ (5 ml) was stirred for 2 hours. The solvent was removed and the crude was purified by flash column chromatography on silica gel (50% ethyl acetate) to afford Compound 20 (112 mg, 100%).

$^1$H NMR (600 MHz, CD$_3$OD) δ 8.29 (d, J=1.76 Hz, 1H), 8.15 (d, J=2.05 Hz, 1H), 7.70 (d, J=7.92 Hz, 1H), 7.57 (s, 1H), 7.47-7.51 (m, 1H), 7.42-7.46 (m, 1H), 7.28-7.35 (m, 1H), 7.07-7.18 (m, 2H), 6.97-7.04 (m, 1H), 6.89 (d, J=7.63 Hz, 1H), 4.77 (s, 2H).

EXAMPLE 39

Intermediate 21

5-methyl-3-nitropyridine-2-thiol

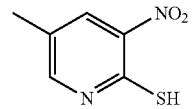

To a solution of 2-chloro-5-methyl-3-nitropyridine (1 g, 5.80 mmol) in dioxane (5 ml) and water (1 ml) was added Na$_2$S.9H$_2$O (1.39 g, 5.80 mmol) and the reaction was stirred at rt for 3 hours. The reaction was quenched with 1N HCl and

EXAMPLE 40

Intermediate 22

2-(benzylthio)-5-methyl-3-nitropyridine

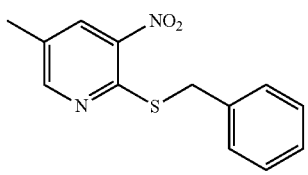 [SMILES: Cc1cnc(SCc2ccccc2)c([N+](=O)[O-])c1]

To the crude Intermediate 21 in DMF (10 ml) was added (bromomethyl)benzene (991 mg, 5.80 mmol) and K$_2$CO$_3$ (2.4 g, 17.39 mmol) and the reaction was stirred at room temperature for 16 hours. The reaction mixture was poured into water (50 ml) and extracted with ethyl acetate (2×50 ml). The organic layer was washed with brine and then dried over Na$_2$SO$_4$, concentrated in vacuo and purified by flash column chromatography on silica gel (0~30% ethyl acetate in hexane) to give Intermediate 22 (660 mg, 44%).

$^1$H NMR (600 MHz, acetone) δ 8.71 (d, J=0.88 Hz, 1H), 8.42 (d, J=0.59 Hz, 1H), 7.45 (d, J=7.34 Hz, 2H), 7.30 (t, J=7.63 Hz, 2H), 7.21-7.26 (m, J=7.34 Hz, 1H), 4.49 (s, 2H), 2.45 (s, 3H).

EXAMPLE 41

Intermediate 23

2-(benzylthio)-5-methylpyridin-3-amine

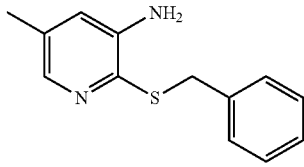 [SMILES: Cc1cnc(SCc2ccccc2)c(N)c1]

To a solution of Intermediate 22 (660 mg, 2.55 mmol) in MeOH (20 ml) was added saturated aqueous NH$_4$Cl (2 ml) and zinc dust (4.1 g, 63.71 mmol). The suspension was stirred at room temperature for 1 hour and was filtered, the filtrate was extracted with EtOAc (×2). The organic layer was washed with brine, dried over Na$_2$SO$_4$, and concentrated in vacuo. The crude Intermediate 23 (512 mg, 88%) was used in the next reaction without further purification.

$^1$H NMR (600 MHz, acetone) δ 7.72 (s, 1H), 7.38 (d, J=7.34 Hz, 2H), 7.26 (t, J=7.48 Hz, 2H), 7.18-7.22 (m, 1H), 6.81 (s, 1H), 4.53 (br. s., 2H), 4.42 (s, 2H), 2.16 (s, 3H).

EXAMPLE 42

Compound 21

N-[2-(benzylsulfanyl)-5-methylpyridin-3-yl]-1-benzofuran-2-sulfonamide

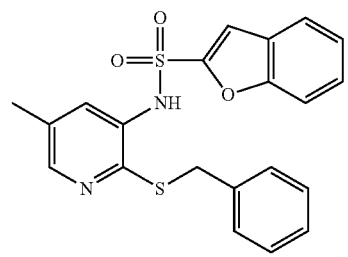 [SMILES: Cc1cnc(SCc2ccccc2)c(NS(=O)(=O)c2cc3ccccc3o2)c1]

To Intermediate 23 (510 mg, 2.23 mmol) in pyridine (5 ml) was added benzofuran-2-sulfonyl chloride (481 mg, 2.23 mmol) and the reaction was stirred at 100° C. for 16 hours and concentrated in vacuo. The crude product was purified by flash column chromatography on silica gel (0-30% EtOAc in hexanes) to yield Compound 21 (466 mg, 51%).

$^1$H NMR (600 MHz, acetone) δ 9.03 (br.s, 1H), 8.24 (d, J=0.88 Hz, 1H), 7.73-7.78 (m, 1H), 7.53-7.62 (m, 2H), 7.49-7.51 (m, 1H), 7.39-7.43 (m, 1H), 7.37 (s, 1H), 7.11-7.20 (m, 3H), 7.04 (dd, J=2.79, 6.60 Hz, 2H), 4.17 (s, 2H), 2.28 (s, 3H).

EXAMPLE 43

Compound 22

N-[2-(benzylsulfinyl)-5-methylpyridin-3-yl]-1-benzofuran-2-sulfonamide

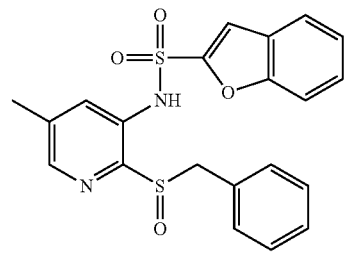 [SMILES: Cc1cnc(S(=O)Cc2ccccc2)c(NS(=O)(=O)c2cc3ccccc3o2)c1]

To a solution of Compound 21 (143 mg, 0.349 mmol) in CH$_2$Cl$_2$ (5 ml) was added mCPBA (70 mg, 0.349 mmol) and the reaction was stirred at room temperature for 3 hours and was concentrated. The residue was purified by flash column chromatography on silica gel (100% EtOAc) to yield Compound 22 (129 mg, 85%).

$^1$H NMR (600 MHz, acetone) δ 11.12 (br. s., 1H), 8.16 (d, J=1.17 Hz, 1H), 7.85 (d, J=0.88 Hz, 1H), 7.79 (s, 1H), 7.67 (s, 1H), 7.61 (s, 1H), 7.47-7.54 (m, 1H), 7.37 (t, J=7.63 Hz, 1H), 7.12-7.26 (m, 3H), 6.98-7.08 (m, 2H), 4.35 (d, J=13.21 Hz, 1H), 4.21 (d, J=13.21 Hz, 1H), 2.36 (s, 3H).

EXAMPLE 44

Compound 23

N-[2-(benzylsulfonyl)-5-methylpyridin-3-yl]-1-benzofuran-2-sulfonamide

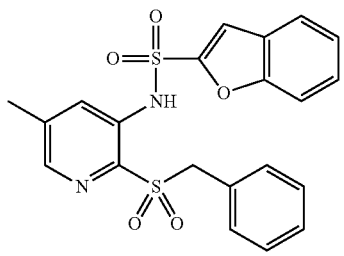 [SMILES: Cc1cnc(S(=O)(=O)Cc2ccccc2)c(NS(=O)(=O)c2cc3ccccc3o2)c1]

To a solution of Compound 21 (241 mg, 0.588 mmol) in CH$_2$Cl$_2$ (5 ml) was added mCPBA (291 mg, 1.47 mmol) and the reaction was stirred at room temperature for 3 hours, and was concentrated. The residue was purified by flash column chromatography on silica gel (100% EtOAc) to yield Compound 23 (203 mg, 78%).

$^1$H NMR (600 MHz, acetone) δ 8.34 (d, J=0.59 Hz, 1H), 7.99 (s, 1H), 7.76 (d, J=7.92 Hz, 1H), 7.70 (s, 1H), 7.59 (s, 1H), 7.51 (td, J=1.03, 7.85 Hz, 1H), 7.35 (t, J=7.63 Hz, 1H), 7.11-7.24 (m, 5H), 4.75 (s, 2H), 2.40 (s, 3H).

EXAMPLE 45

Intermediate 24

5-chloro-2-((2-methylpyridin-3-yl)oxy)-3-nitropyridine

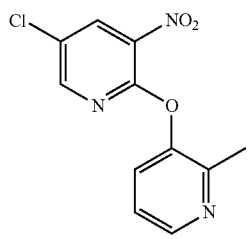

To a solution of 2,5-dichloro-3-nitropyridine (655 mg, 3.41 mmol) in DMF (10 ml) was added 2-methylpyridin-3-ol (368 mg, 3.41 mmol) and K$_2$CO$_3$ (2.35 g, 17.05 mmol) and the reaction was stirred at 90° C. for 3 hours, diluted with H$_2$O, and the resulting solution was extracted with EtOAc. The organic layer was washed with brine, dried over Na$_2$SO$_4$ and concentrated in vacuo, followed by MPLC purification to yield Intermediate 24 as yellow solid (705 mg, 78%).

$^1$H NMR (600 MHz, acetone) δ 8.61-8.68 (m, 1H), 8.34-8.46 (m, 2H), 7.61 (d, J=8.22 Hz, 1H), 7.14-7.46 (m, 1H), 2.37 (s, 3H).

EXAMPLE 46

Intermediate 25

5-chloro-2-((2-methylpyridin-3-yl)oxy)pyridin-3-amine

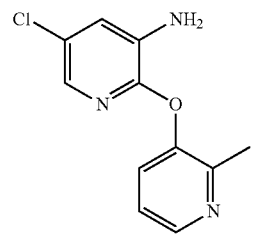 [SMILES: Cc1ncccc1Oc1ncc(Cl)cc1[N+](=O)[O-]]

To a solution of Intermediate 24 (705 mg, 2.92 mmol) in MeOH (15 ml) was added saturated aqueous NH$_4$Cl (2 ml) and zinc dust (4.7 g, 73 mmol). The suspension was stirred at room temperature for 0.5 hour and was filtered, the filtrate was extracted with EtOAc (×2). The organic layer was washed with brine, dried over Na$_2$SO$_4$, and concentrated in vacuo. The crude Intermediate 25 (476 mg, 76%) was used in the next reaction without further purification.

$^1$H NMR (600 MHz, acetone) δ 8.31 (d, J=4.40 Hz, 1H), 7.45 (d, J=7.92 Hz, 1H), 7.21-7.28 (m, 2H), 7.16 (d, J=2.05 Hz, 1H), 5.26 (br. s., 2H), 2.33 (s, 3H).

EXAMPLE 47

Compound 24

N-{5-chloro-2-[(2-methylpyridin-3-yl)oxy]pyridin-3-yl}-1-benzofuran-2-sulfonamide

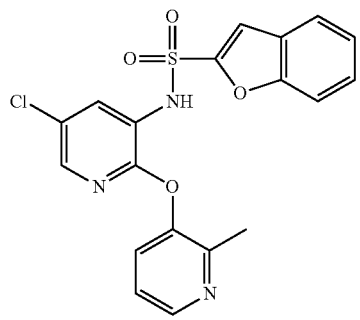 [SMILES: Cc1ncccc1Oc1ncc(Cl)cc1NS(=O)(=O)c1cc2ccccc2o1]

To Intermediate 25 (476 mg, 2.0 mmol) in pyridine (4 ml) was added benzofuran-2-sulfonyl chloride (437 mg, 2.0 mmol) and the reaction was stirred at room temperature for 16 hours. Solvent was removed in vacuo and the crude product was purified by flash column chromatography on silica gel (0-30% EtOAc in hexanes) followed by re-crystallization from 20% EtOAc/Hexane to yield Compound 24 (419 mg, 50%) as a yellow solid.

$^1$H NMR (600 MHz, CD$_3$OD) δ 8.18 (dd, J=1.32, 4.84 Hz, 1H), 8.02 (dd, J=1.03, 2.49 Hz, 1H), 7.79-7.83 (m, 1H), 7.73

(d, J=7.92 Hz, 1H), 7.45-7.53 (m, 3H), 7.33-7.40 (m, 1H), 7.10 (dd, J=4.99, 8.22 Hz, 1H), 6.94 (d, J=9.39 Hz, 1H), 1.99 (s, 3H).

EXAMPLE 48

Intermediate 26 methyl 2-((5-chloro-3-nitropyridin-2-yl)oxy)benzoate

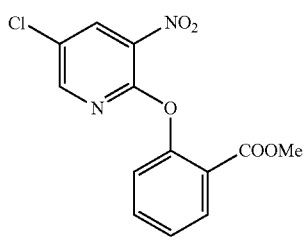 [SMILES: COC(=O)c1ccccc1Oc1ncc(Cl)cc1[N+](=O)[O-]]

To a solution of 2,5-dichloro-3-nitropyridine (1 g, 5.2 mmol) in DMF (10 ml) was added methyl 2-hydroxybenzoate (790 mg, 5.2 mmol) and $K_2CO_3$ (3.6 g, 25.9 mmol) and the reaction was stirred at 90° C. for 3 hours, diluted with $H_2O$, and the resulting solution was extracted with EtOAc. The organic layer was washed with brine, dried over $Na_2SO_4$ and concentrated in vacuo, followed by MPLC purification to yield Intermediate 26 as clear oil (1.5 g, 93%).

$^1$H NMR (600 MHz, acetone) δ 8.59-8.64 (m, 1H), 8.32 (d, J=1.76 Hz, 1H), 8.05 (dd, J=1.61, 7.78 Hz, 1H), 7.72-7.78 (m, 1H), 7.45-7.50 (m, 1H), 7.40 (d, J=8.22 Hz, 1H), 3.65 (s, 3H).

EXAMPLE 49

Intermediate 27 methyl 2-((3-amino-5-chloropyridin-2-yl)oxy)benzoate

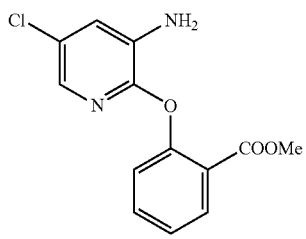 [SMILES: COC(=O)c1ccccc1Oc1ncc(Cl)cc1N]

To a solution of Intermediate 26 (1.5 mg, 4.82 mmol) in MeOH (30 ml) was added saturated aqueous $NH_4Cl$ (2 ml) and zinc dust (7.8 g, 121 mmol). The suspension was stirred at room temperature for 1 hour and was filtered, and the filtrate was extracted with EtOAc (×2). The organic layer was washed with brine, dried over $Na_2SO_4$, and concentrated in vacuo. The crude Intermediate 27 (1.12 g, 83%) was used in the next reaction without further purification.

$^1$H NMR (600 MHz, acetone) δ 7.92 (dd, J=1.47, 7.92 Hz, 1H), 7.57-7.69 (m, 1H), 7.28-7.38 (m, 2H), 7.19 (d, J=1.76 Hz, 1H), 7.12 (dd, J=0.59, 2.35 Hz, 1H), 5.18 (br. s., 2H), 3.66 (s, 3H).

EXAMPLE 50

Compound 25 methyl 2-({3-[(1-benzofuran-2-ylsulfonyl)amino]-5-chloropyridin-2-yl}oxy)benzoate

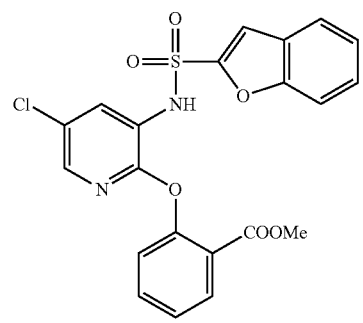 [SMILES: COC(=O)c1ccccc1Oc1ncc(Cl)cc1NS(=O)(=O)c1cc2ccccc2o1]

To Intermediate 27 (413 mg, 1.5 mmol) in pyridine (5 ml) was added benzofuran-2-sulfonyl chloride (320 mg, 1.5 mmol) and the reaction was stirred at room temperature for 16 hours. Solvent was removed in vacuo and the crude product was purified by flash column chromatography on silica gel (0-30% EtOAc in hexanes) to yield Compound 25 (627 mg, 92%) as a yellow solid.

$^1$H NMR (600 MHz, CD$_3$OD) δ 8.00 (d, J=2.35 Hz, 1H), 7.89 (dd, J=1.32, 7.78 Hz, 1H), 7.75 (d, J=7.92 Hz, 1H), 7.71 (d, J=2.35 Hz, 1H), 7.47-7.55 (m, 3H), 7.35-7.41 (m, J=7.63 Hz, 2H), 7.26 (t, J=7.63 Hz, 1H), 6.52 (d, J=8.22 Hz, 1H), 3.47 (s, 3H).

EXAMPLE 51

Compound 26

2-({3-[(1-benzofuran-2-ylsulfonyl)amino]-5-chloro-pyridin-2-yl}oxy)benzoic acid

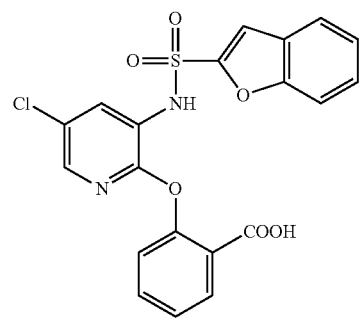 [SMILES: O=C(O)c1ccccc1Oc1ncc(Cl)cc1NS(=O)(=O)c1cc2ccccc2o1]

To Compound 25 (627 mg, 1.36 mmol) in MeOH (30 ml) was added NaOH (5N, 2 ml) and the reaction was stirred at room temperature for 3 hours. The mixture was acidified with 10% HCl, extracted with EtOAc (×2). The combined organic layer was washed with brine, dried over $Na_2SO_4$, and concentrated in vacuo. The crude product was recrystallized from minimal MeOH and CH$_2$Cl$_2$ to yield Compound 26 (485 mg, 80%).

$^1$H NMR (600 MHz, acetone) δ 11.22 (br. s., 1H), 9.66 (br. s., 1H), 7.96-8.01 (m, 2H), 7.81 (d, J=7.92 Hz, 1H), 7.77 (d, J=2.35 Hz, 1H), 7.65 (s, 1H), 7.58-7.61 (m, 1H), 7.54 (ddd, J=1.17, 7.26, 8.29 Hz, 1H), 7.49 (td, J=1.61, 7.70 Hz, 1H), 7.38-7.43 (m, 1H), 7.32 (t, J=7.63 Hz, 1H), 6.80 (d, J=7.92 Hz, 1H).

EXAMPLE 52

Intermediate 28

(3-amino-5-chloropyridin-2-yl)(morpholino)methanone

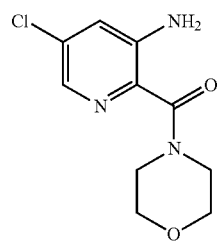 [SMILES: Nc1cc(Cl)cnc1C(=O)N1CCOCC1]

A solution of 3-amino-5-chloropicolinic acid hydrogen chloride (226 mg, 1.08 mmol), morpholine (94 µl, 1.08 mmol), EDCI (308 mg, 1.61 mmol) and DMAP (394 mg, 3.23 mmol) in CH$_2$Cl$_2$ (5 ml) was stirred at room temperature overnight, diluted with H$_2$O, and the resulting solution was extracted with CH$_2$Cl$_2$. The organic layer was washed with brine, dried over Na$_2$SO$_4$ and concentrated in vacuo, followed by MPLC purification to yield Intermediate 28 as a yellow oil (173 mg, 66%).

$^1$H NMR (600 MHz, acetone) δ 7.80 (d, J=2.35 Hz, 1H), 7.28 (d, J=2.35 Hz, 1H), 5.78 (br. s., 2H), 3.83-4.04 (m, 4H), 2.51 (d, J=4.40 Hz, 4H).

EXAMPLE 53

Compound 27

N-[5-chloro-2-(morpholin-4-ylcarbonyl)pyridin-3-yl]-1-benzofuran-2-sulfonamide

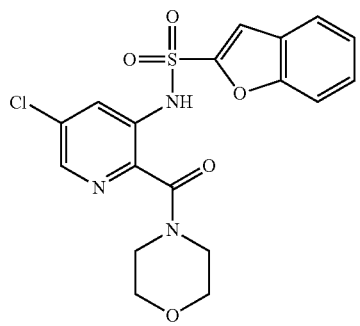 [SMILES: O=C(c1ncc(Cl)cc1NS(=O)(=O)c1cc2ccccc2o1)N1CCOCC1]

To Intermediate 28 (170 mg, 0.70 mmol) in pyridine (3 ml) was added benzofuran-2-sulfonyl chloride (152 mg, 0.70 mmol) and the reaction was stirred at room temperature for 16 hours. Solvent was removed in vacuo and the crude product was purified by flash column chromatography on silica gel (0-30% EtOAc in hexanes) to yield Compound 27 (78 mg, 26%).

$^1$H NMR (600 MHz, acetone) δ 7.85-7.94 (m, 1H), 7.71 (d, J=2.05 Hz, 1H), 7.64 (d, J=8.22 Hz, 1H), 7.46 (d, J=8.22 Hz, 1H), 7.33 (ddd, J=1.17, 7.26, 8.29 Hz, 1H), 7.20-7.27 (m, 1H), 7.14 (d, J=0.59 Hz, 1H), 3.67 (s, 4H), 3.47-3.57 (m, 2H), 3.09-3.18 (m, 2H).

EXAMPLE 54

Intermediate 29

1-(3-amino-5-chloropicolinoyl)piperidin-4-one

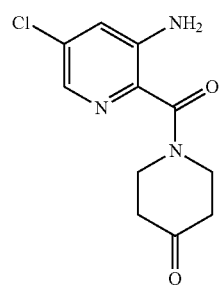 [SMILES: Nc1cc(Cl)cnc1C(=O)N1CCC(=O)CC1]

A solution of 3-amino-5-chloropicolinic acid hydrogen chloride (303 mg, 1.44 mmol), piperidin-4-one (220 mg, 1.44 mmol), EDCI (413 mg, 2.16 mmol) and DMAP (528 mg, 4.33 mmol) in CH$_2$Cl$_2$ (5 ml) was stirred at room temperature overnight, diluted with H$_2$O, and the resulting solution was extracted with CH$_2$Cl$_2$. The organic layer was washed with brine, dried over Na$_2$SO$_4$ and concentrated in vacuo, followed by MPLC purification to yield Intermediate 29 (255 mg, 79%).

$^1$H NMR (600 MHz, acetone) δ 7.80 (s, 1H), 7.28 (d, J=2.35 Hz, 1H), 5.78 (br. s., 2H), 3.72-4.13 (m, 4H), 2.51 (d, J=4.40 Hz, 4H).

EXAMPLE 55

Compound 28

N-{5-chloro-2-[(4-oxopiperidin-1-yl)carbonyl]pyridin-3-yl}-1-benzofuran-2-sulfonamide To Intermediate 29 (288 mg, 1.13 mmol) in pyridine (3 ml) was added benzofuran-2-sulfonyl chloride (245 mg, 1.13 mmol) and the reaction was stirred at room temperature for 16 hours. Solvent was removed in vacuo and the crude product was purified by flash column chromatography on silica gel (0-30% EtOAc in hexanes) to yield Compound 28 (52 mg, 10%).

¹H NMR (300 MHz, CDCl₃) δ 8.24 (d, J=2.05 Hz, 1H), 8.14 (d, J=2.05 Hz, 1H), 7.65 (d, J=7.62 Hz, 1H), 7.42-7.55 (m, 2H), 7.29-7.41 (m, 2H), 3.86 (t, J=6.15 Hz, 2H), 3.51 (t, J=6.15 Hz, 2H), 2.50 (t, J=6.30 Hz, 2H), 2.36 (t, J=5.86 Hz, 2H).

EXAMPLE 56

Intermediate 30

5-chloro-3-nitropicolinic acid

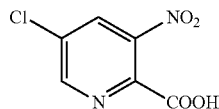

To a suspension of 4-(5-chloro-3-nitropyridin-2-yl)-2-methylbut-3-yn-2-ol (2.1 g, 8.71 mmol) in H₂O (30 ml) was added KMnO₄ (4.55 g, 28.78 mmol) portionwise over 30 min at 75° C. After addition, the reaction was stirred at 75° C. for 2 hours, then cooled down to room temperature and adjusted pH to ~9 by addition of 1N NaOH and filtered away the solid. The filtrate was diluted with H₂O, and extracted with EtOAc and discarded. The aqueous portion was acidified to pH 2-3 with 1N HCl, the resulting solution was extracted with EtOAc, washed with brine, dried over Na₂SO₄ and concentrated in vacuo to yield Intermediate 30 as yellow solid (1.23 g, 71%).

¹H NMR (300 MHz, acetone) δ 8.98 (d, J=2.05 Hz, 1H), 8.67 (d, J=2.05 Hz, 1H).

EXAMPLE 57

Intermediate 31

(5-chloro-3-nitropyridin-2-yl)(phenyl)methanone

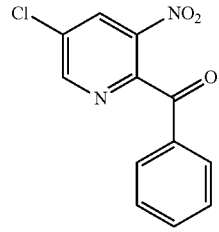

To a solution of Intermediate 30 (724 mg, 3.62 mmol) in CH₂Cl₂ (5 ml) was added oxalyl chloride (3.6 ml, 7.24 mmol) at room temperature followed by a drop of DMF. After stirring for 1.5 hours, the mixture was concentrated and dried under high vacuum. The crude acid chloride was dissolved in benzene (30 ml) and AlCl₃ (499 mg, 3.75 mmol) was added. The resulting mixture was heated at 80° C. for 3.5 hours. The reaction was quenched with NaHCO₃ and extracted with EtOAc (×2). The organic layer was washed with brine, dried over Na₂SO₄, and concentrated in vacuo. The crude product was purified by flash column chromatography on silica gel (0-30% EtOAc in hexanes) to yield Intermediate 31 (675 mg, 72%).

¹H NMR (300 MHz, acetone) δ 9.05 (d, J=2.34 Hz, 1H), 8.83 (d, J=2.05 Hz, 1H), 7.85-7.99 (m, 2H), 7.66-7.80 (m, 1H), 7.48-7.64 (m, 2H).

EXAMPLE 58

Intermediate 32

(3-amino-5-chloropyridin-2-yl)(phenyl)methanone

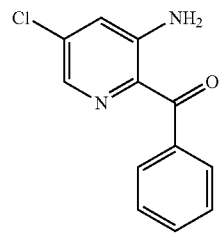 [SMILES: O=C(c1ccccc1)c1ncc(Cl)cc1[N+](=O)[O-]]

To a solution of Intermediate 31 (477 mg, 1.84 mmol) in EtOH (10 ml) was added SnCl₂ (1.95 g, 10.28 mmol). The mixture was stirred at 80° C. for 2 days. The solvent was removed, NaOH (1N) was added to adjusted the pH ~11. The cloud mixture was extracted with EtOAc (×2). The organic layer was washed with brine, dried over Na₂SO₄, and concentrated in vacuo. The crude product was purified by flash column chromatography on silica gel (0-30% EtOAc in hexanes) to yield Intermediate 32 (308 mg, 73%).

¹H NMR (300 MHz, acetone) δ 7.89-7.97 (m, 1H), 7.87 (d, J=2.05 Hz, 1H), 7.38-7.61 (m, 3H), 7.04-7.24 (m, 2H).

EXAMPLE 59

Compound 29

N-[5-chloro-2-(phenylcarbonyl)pyridin-3-yl]-1-benzofuran-2-sulfonamide

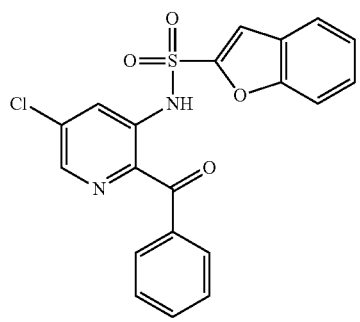 [SMILES: O=C(c1ccccc1)c1ncc(Cl)cc1NS(=O)(=O)c1cc2ccccc2o1]

To Intermediate 32 (300 mg, 1.29 mmol) in pyridine (5 ml) was added benzofuran-2-sulfonyl chloride (288 mg, 1.29 mmol) and DMAP (cat.) and the reaction was stirred at 100° C. for 16 hours. Solvent was removed in vacuo and the crude product was purified by flash column chromatography on silica gel (0-30% EtOAc in hexanes) and further purified by preparative TLC to yield Compound 29 (118 mg, 22%).

$^1$H NMR (300 MHz, acetone) δ 8.46 (d, J=2.05 Hz, 1H), 8.28 (d, J=2.05 Hz, 1H), 7.71-7.83 (m, 4H), 7.54-7.63 (m, 1H), 7.28-7.50 (m, 5H).

EXAMPLE 60

Intermediate 33

5-chloro-3-nitro-2-(phenylthio)pyridine

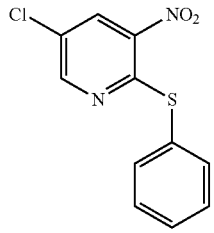 [SMILES: O=[N+]([O-])c1cc(Cl)cnc1Sc1ccccc1]

To a solution of 2,5-dichloro-3-nitropyridine (995 mg, 5.0 mmol) in MeOH (5 ml) was added benzenethiol (0.51 ml, 5.0 mmol) and 4M NaOH (1.25 ml, 5.0 mmol) and the reaction was stirred at room temperature for 4 hours, diluted with 1M NaOH, extracted with EtOAc. The organic layer was washed with brine, dried over Na$_2$SO$_4$, and concentrated in vacuo. The crude was purified by flash column chromatography on silica gel (0-5% EtOAc in hexanes) to yield Intermediate 33 as a yellow solid (1.33 g, 100%).

1H NMR (CHLOROFORM-d) δ 8.49 (d, J=2.1 Hz, 1H), 8.44 (d, J=2.3 Hz, 1H), 7.51-7.56 (m, 2H), 7.43-7.49 (m, 3H).

EXAMPLE 61

Intermediate 34

5-chloro-2-(phenylthio)pyridin-3-amine

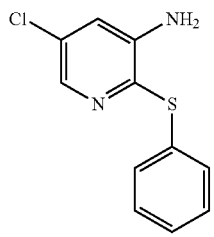 [SMILES: Nc1cc(Cl)cnc1Sc1ccccc1]

To a solution of Intermediate 33 (0.65 g, 2.43 mmol) in HOAc (10 ml) was added iron powder (0.68 g, 12.2 mmol). The suspension was stirred at 70° C. for 1.5 hours and was concentrated, diluted with EtOAc, washed with 1M NaOH, brine, dried over Na$_2$SO$_4$, and concentrated in vacuo. The crude product was purified by flash column chromatography on silica gel (10% EtOAc in hexanes) to yield Intermediate 34 as a light brown solid (567 mg, 98%).

1H NMR (CHLOROFORM-d) δ: 7.96 (d, J=2.3 Hz, 1H), 7.18-7.32 (m, 5H), 7.02 (d, J=2.3 Hz, 1H), 4.27 (br. s., 2H).

EXAMPLE 62

Compound 30

N-[5-chloro-2-(phenylsulfanyl)pyridin-3-yl]-1-benzofuran-2-sulfonamide

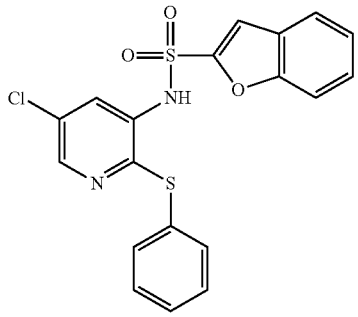 [SMILES: O=S(=O)(Nc1cc(Cl)cnc1Sc1ccccc1)c1cc2ccccc2o1]

To Intermediate 34 (551 mg, 2.32 mmol) in pyridine (10 ml) was added benzofuran-2-sulfonyl chloride (505 mg, 2.32 mmol) and DMAP (28 mg, 0.23 mmol). The reaction was stirred at 100° C. for 12 hours, when additional benzofuran-2-sulfonyl chloride (505 mg, 2.32 mmol) was added. The reaction was continued at 100° C. for 12 hours and was concentrated in vacuo. The residue was purified by flash column chromatography on silica gel (10-30% EtOAc in hexanes) to yield Compound 30 as a light brown solid (271 mg, 28%).

1H NMR (CHLOROFORM-d) δ: 8.23 (d, J=2.1 Hz, 1H), 8.02 (d, J=2.1 Hz, 1H), 7.70 (br. s., 1H), 7.66 (dt, J=7.8, 1.1 Hz, 1H), 7.46-7.50 (m, 2H), 7.40 (s, 1H), 7.31-7.38 (m, 1H), 7.09-7.23 (m, 5H).

EXAMPLE 63

Compound 31

N-[5-chloro-2-(phenylsulfonyl)pyridin-3-yl]-1-benzofuran-2-sulfonamide

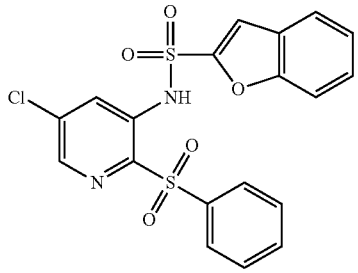 [SMILES: O=S(=O)(Nc1cc(Cl)cnc1S(=O)(=O)c1ccccc1)c1cc2ccccc2o1]

To a solution of Compound 30 (200 mg, 0.48 mmol) in CH$_2$Cl$_2$ (5 ml) was added mCPBA (173 mg, ~0.72 mmol) and the reaction was stirred at room temperature for 2 hours and additional mCPBA (58 mg, ~0.24 mmol) was added. The reaction was continued for 1 hour and was diluted with saturated aqueous NaHCO$_3$ and saturated aqueous Na$_2$CO$_3$ to ~pH8, extracted with EtOAc (×3). The combined organic layer was washed with brine, dried over Na$_2$SO$_4$, and concentrated in vacuo. The residue was purified by flash column chromatography on silica gel (50-100% EtOAc in hexanes followed by 5% MeOH in EtOAc) to yield Compound 31 (119 mg, 55%).

1H NMR (METHANOL-d4) δ: 8.23 (d, J=2.1 Hz, 1H), 8.19 (s, 1H), 7.82 (dd, J=8.4, 1.0 Hz, 2H), 7.70 (d, J=7.6 Hz, 1H), 7.45-7.58 (m, 4H), 7.29-7.40 (m, 3H).

EXAMPLE 64

Compound 32

N-[5-chloro-2-(phenylsulfinyl)pyridin-3-yl]-1-benzofuran-2-sulfonamide

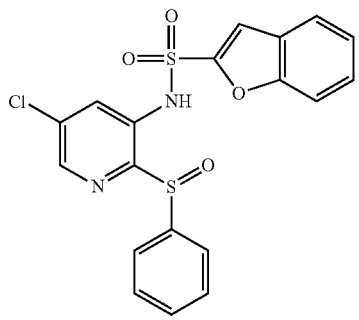 [SMILES: O=S(c1ccccc1)c1ncc(Cl)cc1NS(=O)(=O)c1cc2ccccc2o1]

To a solution of Compound 30 (200 mg, 0.48 mmol) in CH$_2$Cl$_2$ (5 ml) was added mCPBA (173 mg, ~0.72 mmol) and the reaction was stirred at room temperature for 2 hours and additional mCPBA (58 mg, ~0.24 mmol) was added. The reaction was continued for 1 hour and was diluted with saturated aqueous NaHCO$_3$ and saturated aqueous Na$_2$CO$_3$ to ~pH8, extracted with EtOAc (×3). The combined organic layer was washed with brine, dried over Na$_2$SO$_4$, and concentrated in vacuo. The residue was purified by flash column chromatography on silica gel (50-100% EtOAc in hexanes followed by 5% MeOH in EtOAc) to yield Compound 32 (73 mg, 35%).

1H NMR (METHANOL-d4) δ: 8.03 (s, 1H), 7.88 (d, J=1.8 Hz, 1H), 7.70-7.76 (m, 2H), 7.60 (dt, J=7.8, 0.9 Hz, 1H), 7.35-7.39 (m, 2H), 7.21-7.29 (m, 4H), 7.01 (s, 1H).

EXAMPLE 65

Intermediate 35

5-chloro-2-((2-methylpyridin-3-yl)methoxy)-3-nitropyridine

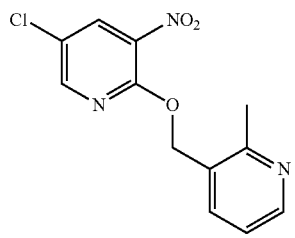 [SMILES: Cc1ncccc1COc1ncc(Cl)cc1[N+](=O)[O-]]

To a solution of 5-chloro-2-fluoro-3-nitropyridine (520 mg, 2.96 mmol) in DMF (10 ml) was added (2-methylpyridin-3-yl)methanol (364 mg, 2.96 mmol) and K$_2$CO$_3$ (2.00 g, 14.82 mmol) and the reaction was stirred at room temperature for 16 hours, diluted with H$_2$O, and the resulting solution was extracted with EtOAc. The organic layer was washed with brine, dried over Na$_2$SO$_4$ and concentrated in vacuo, followed by MPLC purification to yield Intermediate 36 as a yellow solid (500 mg, 61%).

$^1$H NMR (600 MHz, CD$_3$OD) δ 8.32-8.44 (m, 1H), 7.87-7.98 (m, 2H), 7.65 (dd, J=2.64, 9.10 Hz, 1H), 7.46 (d, J=9.10 Hz, 1H), 5.31 (s, 2H), 2.58 (s, 3H).

EXAMPLE 66

Intermediate 36

5-chloro-2-((2-methylpyridin-3-yl)methoxy)pyridine-3-amine

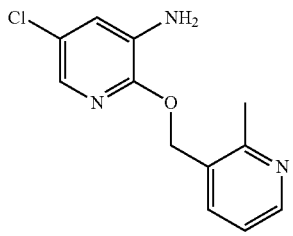 [SMILES: Cc1ncccc1COc1ncc(Cl)cc1N]

To a solution of Intermediate 35 (490 mg, 1.76 mmol) in MeOH (20 ml) was added saturated aqueous NH$_4$Cl (2 ml) and zinc dust (2.9 g, 44 mmol). The suspension was stirred at room temperature for 1 hour and was filtered, and the filtrate was extracted with EtOAc (×2). The organic layer was washed with brine, dried over Na$_2$SO$_4$, and concentrated in vacuo. The Intermediate 36 (439 mg, 100%) was used in the next reaction without further purification.

$^1$H NMR (300 MHz, acetone) δ 8.52 (d, J=3.80, 1H), 7.88 (d, J=7.91 Hz, 1H), 6.94 (d, J=8.50 Hz, 1H), 6.77 (d, J=2.64 Hz, 1H), 6.56 (dd, J=2.64, 8.50 Hz, 1H), 5.16 (s, 2H), 2.62 (s, 3H).

EXAMPLE 67

Compound 33

N-{5-chloro-2-[(2-methylpyridin-3-yl)methoxy]pyridin-3-yl}-1-benzofuran-2-sulfonamide

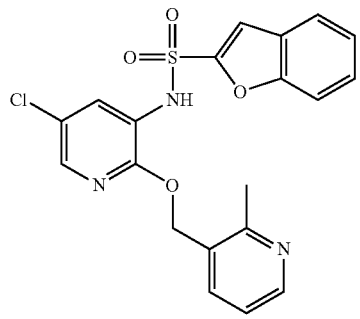 [SMILES: Cc1ncccc1COc1ncc(Cl)cc1NS(=O)(=O)c1cc2ccccc2o1]

To Intermediate 37 (439 mg, 1.77 mmol) in pyridine (5 ml) was added benzofuran-2-sulfonyl chloride (382 mg, 1.77 mmol) and the reaction was stirred at 100° C. for 16 hours.

Solvent was removed in vacuo and the crude product was purified by flash column chromatography on silica gel (0-100% EtOAc in hexanes) to yield Compound 33 (350 mg, 46%) as a yellow solid.

$^1$H NMR (300 MHz, DMSO-d$_6$) δ 8.68 (dd, J=1.32, 5.71 Hz, 1H), 8.45 (d, J=7.62 Hz, 1H), 7.82 (dd, J=5.71, 7.77 Hz, 1H), 7.60 (d, J=7.62 Hz, 1H), 7.33-7.48 (m, 4H), 7.19-7.31 (m, 2H), 4.89 (s, 2H), 2.46 (s, 3H).

EXAMPLE 68

Intermediate 37

2-bromo-5-chloropyridin-3-amine

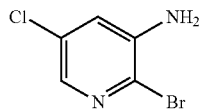

To a suspension of iron powder (1.3 g, 23.16 mmol) in AcOH (8 ml) at 80° C. was added a solution of 2-bromo-5-chloro-3-nitropyridine (1 g, 4.21 mmol) in AcOH (8 ml) via addition funnel and the reaction was stirred at 80° C. for 30 min. The reaction was subsequently cooled to room temperature, diluted with EtOAc, filtered through a pad of Celtite and concentrated in vacuo. The residue was dissolved in EtOAc, and washed with 1N NaOH and brine, dried over Na$_2$SO$_4$ and concentrated in vacuo to afford Intermediate 38 (861 mg, 99%) as a yellow solid which was used directly without further purification.

$^1$H NMR (300 MHz, acetone) δ 7.62 (d, J=2.34 Hz, 1H), 7.22 (d, J=2.34 Hz, 1H), 5.40 (br. s., 2H).

EXAMPLE 69

Intermediate 38

N-(2-bromo-5-chloropyridin-3-yl)benzofuran-2-sulfonamide

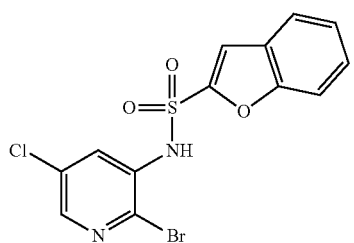 [SMILES: O=S(=O)(Nc1cc(Cl)cnc1Br)c1cc2ccccc2o1]

To Intermediate 37 (861 mg, 4.16 mmol) in pyridine (5 ml) was added benzofuran-2-sulfonyl chloride (900 mg, 4.16 mmol) and the reaction was stirred at 100° C. for 16 hours. Solvent was removed in vacuo and the crude product was purified by flash column chromatography on silica gel (0-100% EtOAc in hexanes) to yield Intermediate 38 (490 mg, 31%).

$^1$H NMR (300 MHz, DMSO-d$_6$) δ 8.32 (d, J=2.34 Hz, 1H), 7.86 (d, J=2.34 Hz, 1H), 7.73-7.78 (m, 1H), 7.69 (dd, J=0.88, 8.20 Hz, 1H), 7.46-7.56 (m, 2H), 7.32-7.41 (m, 1H).

EXAMPLE 70

Intermediate 39

N-(2-bromo-5-chloropyridin-3-yl)-N-(methoxymethyl)benzofuran-2-sulfonamide

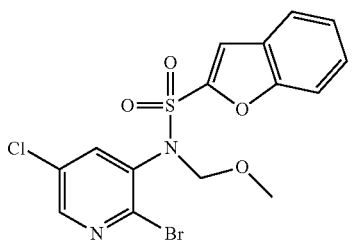 [SMILES: COCN(c1cc(Cl)cnc1Br)S(=O)(=O)c1cc2ccccc2o1]

To a solution of Intermediate 38 (377 mg, 0.974 mmol) in THF (10 ml) at 0° C. was added NaH (37 mg, 95%, 1.46 mmol) and further stirred for 30 min. Then MOMCl (81 ul, 1.07 mmol) was added into the mixture at 0° C. and further stirred for 1 hour more. Water was added to quenched the reaction, extracted with EtOAc (×2), washed with brine and dried over Na$_2$SO$_4$ and concentrated in vacuo. The crude was purified by flash column chromatography on silica gel (0-30% EtOAc in hexanes) to yield Intermediate 39 (350 mg, 83%).

$^1$H NMR (600 MHz, CDCl$_3$) δ 8.37 (d, J=2.35 Hz, 1H), 7.76 (d, J=2.64 Hz, 1H), 7.67 (dt, J=0.99, 7.70 Hz, 1H), 7.59 (dd, J=0.73, 8.36 Hz, 1H), 7.51 (ddd, J=1.32, 7.19, 8.51 Hz, 1H), 7.36 (td, J=1.03, 7.56 Hz, 1H), 7.31 (d, J=0.88 Hz, 1H), 5.35 (br. s., 1H), 5.01 (br. s., 1H), 3.50 (s, 3H).

EXAMPLE 71

Intermediate 40

N-methoxy-N-methyl-2-phenylacetamide

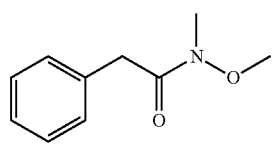

To a mixture of 2-phenylacetyl chloride (1 g, 6.47 mmol) and N,O-dimethylhydroxylamine (757 mg, 7.76 mmol) in CH$_2$Cl$_2$ (30 ml) was added TEA (2.7 ml, 19.41 mmol) at 0° C. After the reaction was stirred for 15 min at 0° C., it was warmed up to room temperature for 1 hour under N$_2$. The mixture was diluted with H$_2$O, and the resulting solution was extracted with EtOAc and washed with brine, dried over Na$_2$SO$_4$ and concentrated in vacuo to yield Intermediate 40 crude (1.03 g, 85%), which was used without further purification.

¹H NMR (600 MHz, acetone) δ 6.71-7.41 (m, 5H), 3.61 (s, 2H), 3.56 (s, 3H), 2.99 (s, 3H).

EXAMPLE 72

Intermediate 41

N-(5-chloro-2-(2-phenylacetyl)pyridin-3-yl)-N-(methoxymethyl)benzofuran-2-sulfonamide

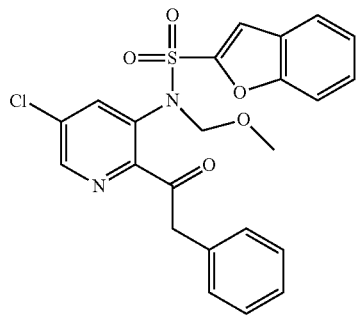 [SMILES: COCN(c1cc(Cl)cnc1C(=O)Cc1ccccc1)S(=O)(=O)c1cc2ccccc2o1]

To a solution of Intermediate 39 (300 mg, 0.69 mmol) in THF (3 ml) under N₂ at −78° C. was added dropwise of i-PrMgCl (1 ml, 2.08 mmol, 2.0 M in THF). The reaction was stirred at −78° C. for 10 min, followed by warming to room temperature for 30 min. The mixture was cooled down to 0° C. and a solution of Intermediate 40 (248 mg, 1.39 mmol) in THF (1 ml) was added and stirred for 3 hour at room temperature. The mixture was diluted with H₂O, and the resulting solution was extracted with EtOAc and washed with brine, dried over Na₂SO₄ and concentrated in vacuo. The crude Intermediate 41 was purified by flash column chromatography on silica gel (0-30% EtOAc in hexanes) to yield (69 mg, 21%).

¹H NMR (600 MHz, acetone) δ 8.80 (t, J=2.05 Hz, 1H), 7.94-7.98 (m, 1H), 7.81 (d, J=7.92 Hz, 1H), 7.65 (d, J=8.51 Hz, 1H), 7.52-7.62 (m, 1H), 7.37-7.50 (m, 2H), 7.12-7.27 (m, 3H), 7.02 (d, J=7.63 Hz, 2H), 5.15 (br. s., 2H), 4.29 (br. s., 2H), 3.41 (s, 3H).

EXAMPLE 73

Compound 34

N-[5-chloro-2-(phenylacetyl)pyridin-3-yl]-1-benzofuran-2-sulfonamide

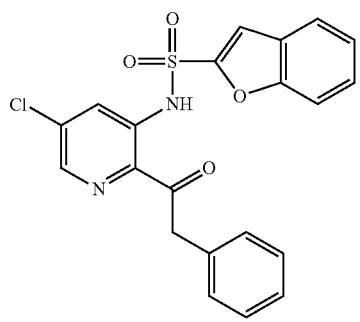 [SMILES: O=C(Cc1ccccc1)c1ncc(Cl)cc1NS(=O)(=O)c1cc2ccccc2o1]

The mixture of Intermediate 42 (58 mg, 0.123 mmol) and 4M HCl in dioxane (5 ml) in H₂O (1 ml) was heated at 100° C. for 3 hours. The mixture was cooled down to room temperature, and adjusted the pH to ~9 by NaHCO₃ (sat.), extracted with EtOAc (×2), The organic layer was washed with brine, dried over Na₂SO₄ and concentrated in vacuo. The crude was purified by flash column chromatography on silica gel (0-30% EtOAc in hexanes) to yield Compound 34 (28 mg, 53%).

¹H NMR (600 MHz, acetone) δ 11.58 (br. s., 1H), 8.32 (d, J=2.05 Hz, 1H), 8.09 (d, J=2.05 Hz, 1H), 7.72 (d, J=0.88 Hz, 1H), 7.63-7.68 (m, 1H), 7.38-7.46 (m, 2H), 7.25 (ddd, J=1.17, 6.75, 7.92 Hz, 1H), 7.10-7.15 (m, 4H), 7.05-7.10 (m, 1H), 4.39 (s, 2H).

EXAMPLE 74

Intermediate 43 methyl 2-(((5-chloro-3-nitropyridin-2-yl)thio)methyl)benzoate

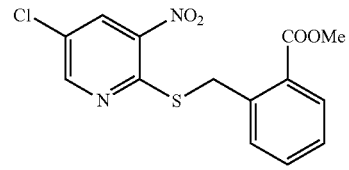 [SMILES: COC(=O)c1ccccc1CSc1ncc(Cl)cc1[N+](=O)[O-]]

To the crude Intermediate 42 in DMF (10 ml) was added methyl 2-(bromomethyl)benzoate (1.47 g, 6.44 mmol) and K₂CO₃ (2.7 g, 19.32 mmol) and the reaction was stirred at room temperature for 16 hours. The reaction mixture was poured into water (50 ml) and extracted with ethyl acetate (2×50 ml). The organic layer was washed with brine and then dried over Na₂SO₄ anhydride, concentrated in vacuo and purified by flash column chromatography on silica gel (0~30% ethyl acetate in hexane) to give Intermediate 43 (573 mg, 26%).

¹H NMR (300 MHz, CD₃OD) δ 8.77 (d, J=2.34 Hz, 1H), 8.60 (d, J=2.34 Hz, 1H), 7.90 (d, J=7.91 Hz, 1H), 7.64 (d, J=6.74 Hz, 1H), 7.42-7.54 (m, 1H), 7.27-7.39 (m, 1H), 4.88 (s, 2H), 3.91 (s, 3H).

EXAMPLE 75

Intermediate 44 methyl 2-(((3-amino-5-chloropyridin-2-yl)thio)methyl)benzoate

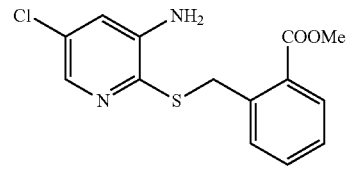

To a solution of Intermediate 43 (575 mg, 1.70 mmol) in MeOH (20 ml) was added saturated aqueous NH₄Cl (2 ml) and zinc dust (2.8 g, 42.40 mmol). The suspension was stirred at room temperature for 1 hour and was filtered, the filtrate was extracted with EtOAc (×2). The organic layer was washed with brine, dried over Na$_2$SO$_4$, and concentrated in vacuo. The crude Intermediate 44 (430 mg, 82%) was used in the next reaction without further purification.

$^1$H NMR (600 MHz, CD$_3$OD) δ 7.87 (d, J=7.92 Hz, 1H), 7.71-7.79 (m, 1H), 7.35-7.43 (m, 2H), 7.30 (t, J=7.34 Hz, 1H), 6.92-7.00 (m, 1H), 4.71 (s, 2H), 3.89 (d, J=0.88 Hz, 3H).

EXAMPLE 76

Compound 35 methyl 2-[({3-[(1-benzofuran-2-ylsulfonyl)amino]-5-chloropyridin-2-yl}sulfanyl)methyl]benzoate

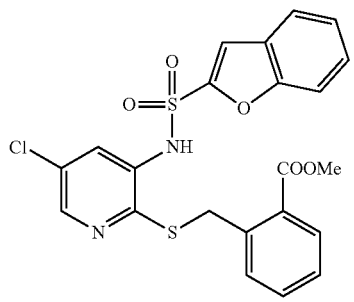 [SMILES: COC(=O)c1ccccc1CSc1ncc(Cl)cc1NS(=O)(=O)c1cc2ccccc2o1]

To Intermediate 44 (430 mg, 1.40 mmol) in pyridine (5 ml) was added benzofuran-2-sulfonyl chloride (300 mg, 1.40 mmol) was added and the reaction was stirred at 100° C. for 16 hours, then additional benzofuran-2-sulfonyl chloride (300 mg, 1.40 mmol) and the reaction was heated for another 24 hours and was concentrated in vacuo. The crude product was purified by flash column chromatography on silica gel (0-30% EtOAc in hexanes) to yield Compound 35 (341 mg, 50%).

$^1$H NMR (300 MHz, CD$_3$OD) δ 8.32 (d, J=2.34 Hz, 1H), 7.70-7.81 (m, 1H), 7.59-7.67 (m, 2H), 7.40-7.49 (m, 2H), 7.12-7.38 (m, 5H), 4.54 (s, 2H), 3.81 (s, 3H).

EXAMPLE 77

Compound 36

2-[({3-[(1-benzofuran-2-ylsulfonyl)amino]-5-chloropyridin-2-yl}sulfanyl)methyl]benzoic acid

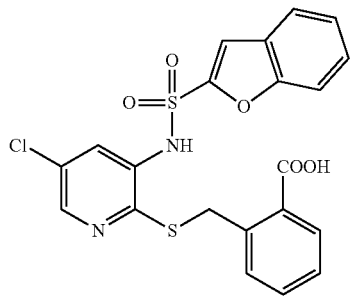 [SMILES: O=C(O)c1ccccc1CSc1ncc(Cl)cc1NS(=O)(=O)c1cc2ccccc2o1]

To Compound 35 (60 mg, 0.12 mmol) in MeOH (5 ml) was added 5N NaOH (1 ml) and the reaction was stirred at room temperature for 3 hours. The mixture was acidified with 10% HCl, extracted with EtOAc (×2). The combined organic layer was washed with brine, dried over Na$_2$SO$_4$, and concentrated in vacuo. The crude product was recrystallized from minimal MeOH and CH$_2$Cl$_2$ to yield Compound 36 (47 mg, 80%).

$^1$H NMR (300 MHz, CD$_3$OD) δ 8.33 (d, J=2.34 Hz, 1H), 7.74-7.85 (m, 1H), 7.56-7.69 (m, 2H), 7.46 (d, J=3.52 Hz, 2H), 7.07-7.38 (m, 5H), 4.58 (s, 3H).

EXAMPLE 79

Compound 37 methyl 2-[({3-[(1-benzofuran-2-ylsulfonyl)amino]-5-chloropyridin-2-yl}sulfinyl)methyl]benzoate

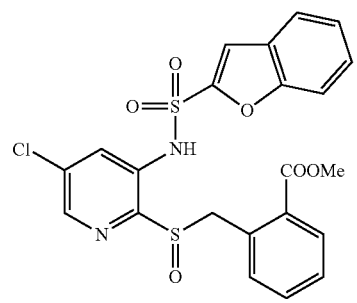

To a solution of Compound 35 (106 mg, 0.22 mmol) in CH$_2$Cl$_2$ (5 ml) was added mCPBA (44 mg, 0.22 mmol) and the reaction was stirred at 0° C. for 30 mins and was concentrated. The residue was purified by flash column chromatography on silica gel (100% EtOAc) to yield Compound 37 (82 mg, 75%).

$^1$H NMR (300 MHz, CD$_3$OD) δ 7.86 (d, J=2.05 Hz, 1H), 7.81 (d, J=1.47 Hz, 1H), 7.78 (d, J=1.17 Hz, 1H), 7.62-7.72 (m, 1H), 7.41-7.48 (m, 1H), 7.21-7.39 (m, 4H), 7.16 (td, J=1.47, 7.47 Hz, 1H), 6.83 (d, J=7.62 Hz, 1H), 5.17 (d, J=12.60 Hz, 1H), 4.79 (d, J=12.60 Hz, 1H), 3.84 (s, 3H).

EXAMPLE 80

Compound 38 methyl 2-[({3-[(1-benzofuran-2-ylsulfonyl)amino]-5-chloropyridin-2-yl}sulfonyl)methyl]benzoate

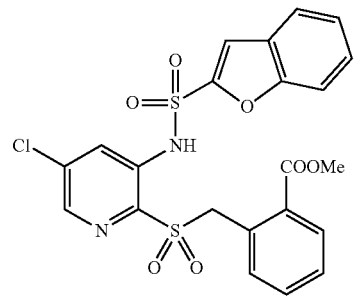 [SMILES: COC(=O)c1ccccc1CS(=O)(=O)c1ncc(Cl)cc1NS(=O)(=O)c1cc2ccccc2o1]

To a solution of Compound 35 (88 mg, 0.18 mmol) in CH$_2$Cl$_2$ (5 ml) was added mCPBA (90 mg, 0.45 mmol) and the reaction was stirred at room temperature for 3 hours and was concentrated. The residue was purified by flash column chromatography on silica gel (100% EtOAc) to yield Compound 38 (55 mg, 59%).

$^1$H NMR (300 MHz, CD$_3$OD) δ 8.18 (d, J=2.05 Hz, 1H), 7.83 (d, J=8.20 Hz, 1H), 7.62-7.73 (m, 2H), 7.20-7.49 (m, 5H), 6.93-7.09 (m, 2H), 5.67 (s, 2H), 3.88 (s, 3H).

EXAMPLE 81

Compound 39

2-[({3-[(1-benzofuran-2-ylsulfonyl)amino]-5-chloropyridin-2-yl}sulfonyl)methyl]benzoic acid

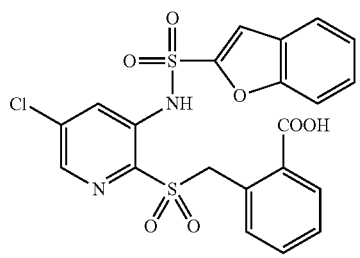 [SMILES: O=C(O)c1ccccc1CS(=O)(=O)c1ncc(Cl)cc1NS(=O)(=O)c1cc2ccccc2o1]

To Compound 38 (55 mg, 0.11 mmol) in MeOH (5 ml) was added 5N NaOH (1 ml) and the reaction was stirred at room temperature for 3 hours. The mixture was acidified with 10% HCl, extracted with EtOAc (×2). The combined organic layer was washed with brine, dried over Na$_2$SO$_4$, and concentrated in vacuo. The crude product was recrystallized from minimal MeOH and CH$_2$Cl$_2$ to yield Compound 39 (36 mg, 43%).

$^1$H NMR (300 MHz, CD$_3$OD) δ 8.35 (s, 1H), 8.21 (d, J=1.76 Hz, 1H), 7.82 (d, J=7.33 Hz, 1H), 7.78-7.78 (m, 1H), 7.75 (s, 1H), 7.62 (s, 1H), 7.48-7.59 (m, 2H), 7.28-7.42 (m, 2H), 7.13-7.27 (m, 2H), 5.40 (s, 2H).

EXAMPLE 82

Intermediate 45

5-fluoro-3-nitro-2-(phenylthio)pyridine

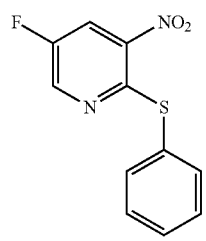 [SMILES: O=[N+]([O-])c1cc(F)cnc1Sc1ccccc1]

To a solution of 2-bromo-5-fluoro-3-nitropyridine (1.17 g, 5.29 mmol) in DMF (10 ml) was added benzenethiol (0.54 ML, 5.29 mmol) and K$_2$CO$_3$ (2.19 g, 15.88 mmol), and the reaction was stirred at room temperature for 16 hours, diluted with H$_2$O, and the resulting solution was extracted with EtOAc. The organic layer was washed with brine, dried over Na$_2$SO$_4$ and concentrated in vacuo, followed by MPLC purification to yield Intermediate 45 as yellow solid.

$^1$H NMR (300 MHz, CD$_3$OD) δ 8.42-8.54 (m, 2H), 7.36-7.49 (m, 5H).

EXAMPLE 83

Intermediate 46

5-fluoro-2-(phenylthio)pyridin-3-amine

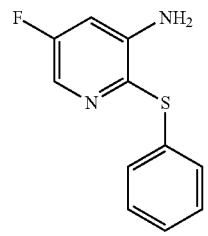 [SMILES: Nc1cc(F)cnc1Sc1ccccc1]

To a solution of Intermediate 45 (1.3 g, 5.29 mmol) in MeOH (20 ml) was added saturated aqueous NH$_4$Cl (2 ml) and zinc dust (8.6 g, 132 mmol). The suspension was stirred at room temperature for 1 hour and was filtered, the filtrate was extracted with EtOAc (×2). The organic layer was washed with brine, dried over Na$_2$SO$_4$, and concentrated in vacuo. The crude Intermediate 46 (735 mg, 55%, 2-step yield) was used in the next reaction without further purification.

$^1$H NMR (300 MHz, CD$_3$OD) δ 7.72 (d, J=2.64 Hz, 1H), 7.06-7.29 (m, 5H), 6.95 (dd, J=2.64, 10.55 Hz, 1H).

EXAMPLE 84

Compound 40

N-[5-fluoro-2-(phenylsulfanyl)pyridin-3-yl]-1-benzofuran-2-sulfonamide

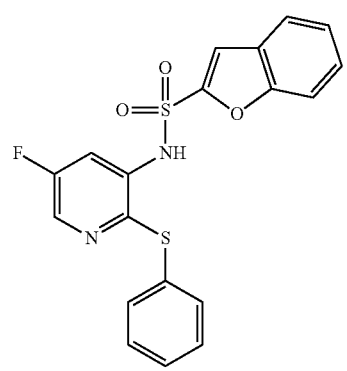 [SMILES: O=S(=O)(Nc1cc(F)cnc1Sc1ccccc1)c1cc2ccccc2o1]

To Intermediate 46 (735 mg, 3.34 mmol) in pyridine (5 ml) was added benzofuran-2-sulfonyl chloride (735 mg, 3.34 mmol) and the reaction was stirred at 100° C. for 16 hours. Solvent was removed in vacuo and the crude product was purified by flash column chromatography on silica gel (0-100% EtOAc in hexanes) to yield Compound 40 (150 mg, 11%).

¹H NMR (300 MHz, CD₃OD) δ 8.12 (d, J=2.64 Hz, 1H), 7.62-7.77 (m, 2H), 7.42-7.58 (m, 2H), 7.28-7.41 (m, 2H), 7.06-7.23 (m, 3H), 6.90-7.00 (m, 2H).

EXAMPLE 85

Compound 41

N-[5-fluoro-2-(phenylsulfinyl)pyridin-3-yl]-1-benzofuran-2-sulfonamide

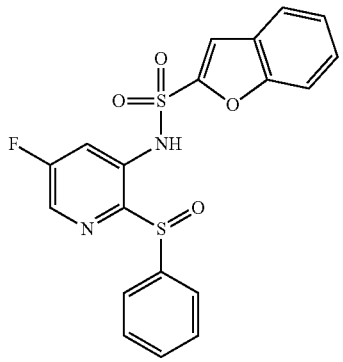 [SMILES: O=S(c1ccccc1)c1ncc(F)cc1NS(=O)(=O)c1cc2ccccc2o1]

To a solution of Compound 40 (60 mg, 0.15 mmol) in CH₂Cl₂ (3 ml) was added mCPBA (30 mg, 0.15 mmol) and the reaction was stirred at 0° C. for 20 min and was concentrated. The residue was purified by flash column chromatography on silica gel (100% EtOAc) to yield Compound 41 (44 mg, 73%).

¹H NMR (300 MHz, CD₃OD) δ 8.25 (br. s., 1H), 7.89 (dd, J=1.90, 10.11 Hz, 1H), 7.68-7.77 (m, 1H), 7.55-7.64 (m, 3H), 7.41-7.54 (m, 3H), 7.32-7.40 (m, 1H), 7.21-7.30 (m, 3H).

EXAMPLE 86

Compound 42

N-[5-fluoro-2-(phenylsulfonyl)pyridin-3-yl]-1-benzofuran-2-sulfonamide

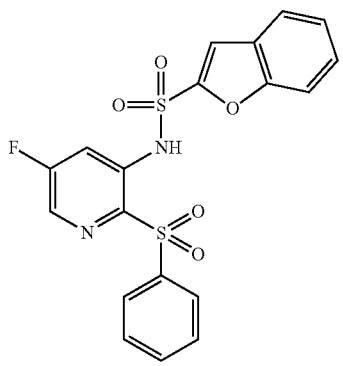 [SMILES: O=S(=O)(Nc1cc(F)cnc1S(=O)(=O)c1ccccc1)c1cc2ccccc2o1]

To a solution of Compound 40 (57 mg, 0.13 mmol) in CH₂Cl₂ (3 ml) was added mCPBA (65 mg, 0.32 mmol) and the reaction was stirred at room temperature for hours and was concentrated. The residue was purified by flash column chromatography on silica gel (100% EtOAc) to yield Compound 42 (38 mg, 62%).

¹H NMR (300 MHz, CD₃OD) δ 8.24 (d, J=2.34 Hz, 1H), 8.07 (dd, J=2.34, 10.26 Hz, 1H), 7.73-7.86 (m, 3H), 7.68 (s, 1H), 7.48-7.61 (m, 3H), 7.29-7.45 (m, 3H).

EXAMPLE 87

Compound 43

2-[({3-[(1-benzofuran-2-ylsulfonyl)amino]-5-chloropyridin-2-yl}sulfinyl)methyl]benzoic acid

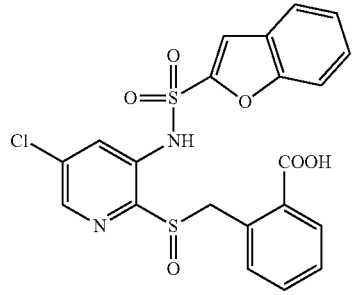 [SMILES: O=C(O)c1ccccc1CS(=O)c1ncc(Cl)cc1NS(=O)(=O)c1cc2ccccc2o1]

To Compound 37 (76 mg, 0.15 mmol) in MeOH (5 ml) was added 5N NaOH (1 ml) and the reaction was stirred at room temperature for 3 hours. The mixture was acidified with 10% HCl, extracted with EtOAc (×2). The combined organic layer was washed with brine, dried over Na₂SO₄, and concentrated in vacuo. The crude product was recrystallized from minimal MeOH and CH₂Cl₂ to yield Compound 43 (67 mg, 90%).

¹H NMR (300 MHz, CD₃OD) δ 8.29 (d, J=2.05 Hz, 1H), 8.00 (d, J=2.05 Hz, 1H), 7.91 (dd, J=1.76, 7.62 Hz, 1H), 7.75 (dd, J=1.03, 7.77 Hz, 1H), 7.61 (s, 1H), 7.44-7.58 (m, 2H), 7.23-7.41 (m, 3H), 6.94 (dd, J=1.32, 7.47 Hz, 2H), 4.94 (d, J=12.60 Hz, 1H), 4.81 (d, J=12.60 Hz, 1H).

EXAMPLE 88

Intermediate 47

5-methyl-3-nitro-2-(phenylthio)pyridine

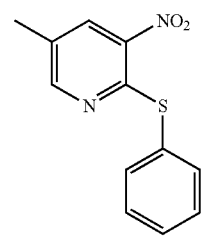 [SMILES: Cc1cnc(Sc2ccccc2)c([N+](=O)[O-])c1]

To a solution of 2-chloro-5-methyl-3-nitropyridine (1.05 g, 5.44 mmol) in MeOH (10 ml) was added benzenethiol (0.56 ML, 5.44 mmol) and NaOH (1.5 ml, 5N) and the reaction was stirred at room temperature for 1.5 hours, diluted with H₂O, and the resulting solution was extracted with EtOAc. The organic layer washed with brine, dried over Na₂SO₄ and concentrated in vacuo, followed by MPLC purification to yield Intermediate 47 (1.26 g, 88%) as a yellow solid.

¹H NMR (300 MHz, CDCl₃) δ 8.29-8.36 (m, 2H), 7.50-7.59 (m, 2H), 7.37-7.49 (m, 3H), 2.36 (t, J=0.73 Hz, 3H).

EXAMPLE 89

Intermediate 48

5-methyl-2-(phenylthio)pyridin-3-amine

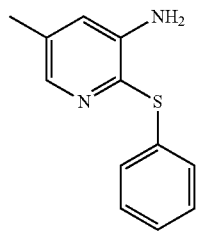

To a solution of Intermediate 47 (1.26 g, 4.76 mmol) in MeOH (50 ml) was added saturated aqueous NH₄Cl (2 ml) and zinc dust (7.8 g, 119 mmol). The suspension was stirred at room temperature for 1 hour and was filtered, the filtrate was extracted with EtOAc (×2). The organic layer was washed with brine, dried over Na₂SO₄, and concentrated in vacuo. The crude Intermediate 49 (1.0 g, 91%) was used in the next reaction without further purification.

¹H NMR (300 MHz, CDCl₃) δ 7.90 (d, J=1.47 Hz, 1H), 7.08-7.28 (m, 5H), 6.86 (d, J=1.17 Hz, 1H), 4.18 (br. s., 2H), 2.27 (s, 3H).

EXAMPLE 90

Compound 44

N-[5-methyl-2-(phenylsulfanyl)pyridin-3-yl]-1-benzofuran-2-sulfonamide

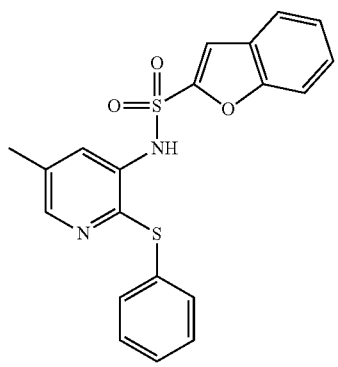 [SMILES: Cc1cnc(Sc2ccccc2)c(NS(=O)(=O)c2cc3ccccc3o2)c1]

To Intermediate 49 (548 mg, 2.54 mmol) in pyridine (5 ml) was added benzofuran-2-sulfonyl chloride (548 mg, 2.54 mmol) and the reaction was stirred at 100° C. for 16 hours. Solvent was removed in vacuo and the crude product was purified by flash column chromatography on silica gel (0-100% EtOAc in hexanes) to yield Compound 44 (691 mg, 69%).

¹H NMR (300 MHz, CD₃OD) δ 8.02 (dd, J=0.73, 2.20 Hz, 1H), 7.62-7.70 (m, 2H), 7.38-7.56 (m, 2H), 7.25-7.36 (m, 2H), 7.02-7.20 (m, 3H), 6.86-6.98 (m, 2H), 4.85 (br. s., 1H), 2.25 (s, 3H).

EXAMPLE 91

Compound 45

N-[5-methyl-2-(phenylsulfinyl)pyridin-3-yl]-1-benzofuran-2-sulfonamide

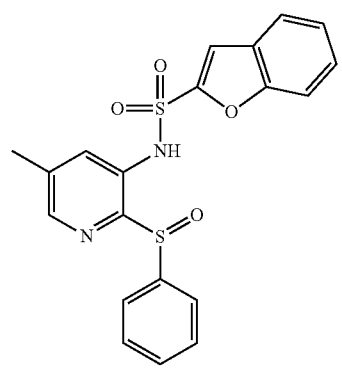 [SMILES: Cc1cnc(S(=O)c2ccccc2)c(NS(=O)(=O)c2cc3ccccc3o2)c1]

To a solution of Compound 44 (106 mg, 0.27 mmol) in CH₂Cl₂ (3 ml) was added mCPBA (54 mg, 0.27 mmol) and the reaction was stirred at 0° C. for 30 min and was concentrated. The residue was purified by flash column chromatography on silica gel (100% EtOAc) to yield Compound 45 (59 mg, 81%).

¹H NMR (300 MHz, CD₃OD) δ 8.19 (s, 1H), 7.82 (s, 1H), 7.70 (d, J=7.62 Hz, 1H), 7.55-7.63 (m, 2H), 7.53 (s, 1H), 7.42-7.50 (m, 2H), 7.21-7.39 (m, 4H), 2.30 (s, 3H).

EXAMPLE 92

Compound 46

N-[5-methyl-2-(phenylsulfonyl)pyridin-3-yl]-1-benzofuran-2-sulfonamide

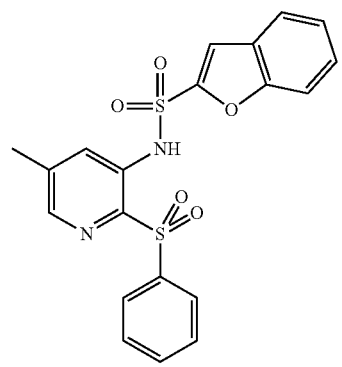 [SMILES: Cc1cnc(S(=O)(=O)c2ccccc2)c(NS(=O)(=O)c2cc3ccccc3o2)c1]

To a solution of Compound 44 (204 mg, 0.52 mmol) in CH₂Cl₂ (5 ml) was added mCPBA (222 mg, 1.29 mmol) and the reaction was stirred at room temperature for 2 hours and was concentrated. The residue was purified by flash column chromatography on silica gel (100% EtOAc) to yield Compound 46 (141 mg, 64%).

$^1$H NMR (300 MHz, CD$_3$OD) δ 8.00 (d, J=9.67 Hz, 2H), 7.84 (d, J=7.62 Hz, 2H), 7.64 (d, J=7.91 Hz, 1H), 7.21-7.55 (m, 7H), 2.28 (s, 3H).

EXAMPLE 93

Intermediate 49 methyl 2-((5-chloro-3-nitropyridin-2-yl)thio)benzoate

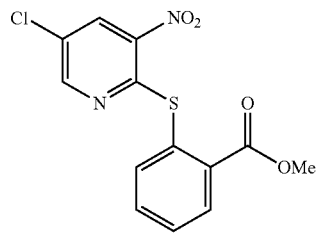 [SMILES: COC(=O)c1ccccc1Sc1ncc(Cl)cc1[N+](=O)[O-]]

To a solution of 2,5-dichloro-3-nitropyridine (1.0 g, 5.2 mmol) in MeOH (5 ml) was added methyl 2-mercaptobenzoate (0.71 ml, 5.2 mmol) and 4M NaOH (1.3 ml, 5.2 mmol) and the reaction was stirred at room temperature for 3 hours. The resulting suspension was diluted with H$_2$O and was filtered to give Intermediate 49 as yellow solid (1.74 g). The crude product was used in the next reaction without further purification.

EXAMPLE 94

Intermediate 50 methyl 2-((3-amino-5-chloropyridin-2-yl)thio)benzoate

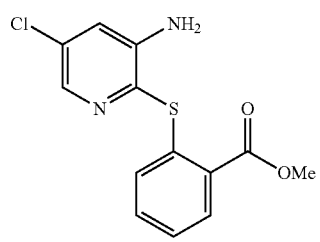 [SMILES: COC(=O)c1ccccc1Sc1ncc(Cl)cc1N]

To a solution of Intermediate 49 (1.7 g, 5.2 mmol) in HOAc (10 ml) was added iron powder (1.5 g, 26 mmol). The suspension was stirred at 70° C. for 1 hour and was diluted with MeOH, treated with Celite and was filtered. The filtrate was concentrated, then taken up in EtOAc, washed with 4M NaOH, brine, dried over Na$_2$SO$_4$, and concentrated in vacuo. The crude product was purified by flash column chromatography on silica gel (10-40% EtOAc in hexanes) to yield Intermediate 50 as light yellow solid (1.4 g, 91%).

1H NMR (METHANOL-d4) δ: 7.98 (dd, J=7.8, 1.6 Hz, 1H), 7.82-7.85 (m, 1H), 7.30-7.37 (m, 1H), 7.19-7.27 (m, 2H), 6.74-6.79 (m, 1H), 3.92 (s, 3H).

EXAMPLE 95

Intermediate 51 methyl 2-((3-(benzofuran-2-sulfonamido)-5-chloropyridin-2-yl)thio)benzoate

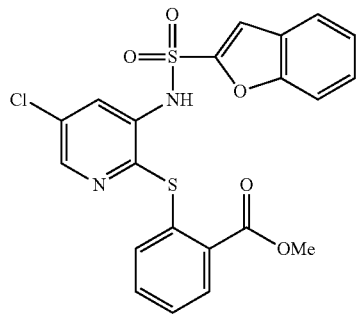 [SMILES: COC(=O)c1ccccc1Sc1ncc(Cl)cc1NS(=O)(=O)c1cc2ccccc2o1]

To Intermediate 50 (300 mg, 1.02 mmol) in pyridine (5 ml) was added benzofuran-2-sulfonyl chloride (221 mg, 1.02 mmol) and a catalytic amount of DMAP. The reaction was stirred at 100° C. for a total of 42 hours, during which additional benzofuran-2-sulfonyl chloride (553 mg, 2.55 mmol) was added in three batches to drive the reaction toward completion. At the end the reaction was concentrated, acidified with 6M HCl, diluted with brine and extracted with EtOAc (×2). The combined organic layer was dried over Na$_2$SO$_4$ and concentrated in vacuo. The residue was purified by flash column chromatography on silica gel (15-20% EtOAc in hexanes) to yield Intermediate 51 (182 mg, 38%).

1H NMR (CHLOROFORM-d) δ: 8.36 (s, 1H), 8.22 (d, J=2.1 Hz, 1H), 8.06 (d, J=2.1 Hz, 1H), 7.79 (dd, J=7.9, 1.5 Hz, 1H), 7.49-7.53 (m, 1H), 7.29-7.36 (m, 2H), 7.17-7.25 (m, 2H), 6.99 (td, J=7.6, 1.2 Hz, 1H), 6.81-6.86 (m, 1H), 6.50 (dd, J=7.9, 0.9 Hz, 1H), 3.83 (s, 3H).

EXAMPLE 96

Compound 47

2-({3-[(1-benzofuran-2-ylsulfonyl)amino]-5-chloropyridin-2-yl}sulfanyl)benzoic acid

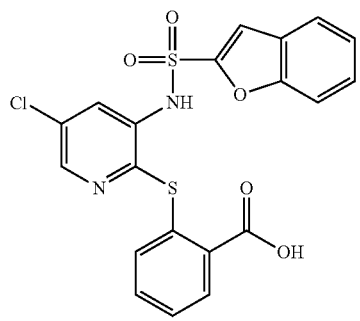 [SMILES: O=C(O)c1ccccc1Sc1ncc(Cl)cc1NS(=O)(=O)c1cc2ccccc2o1]

To a solution of Intermediate 51 (60 mg, 0.13 mmol) in MeOH (5 ml) was added 4M NaOH (0.16 ml, 0.64 mmol) and the reaction was stirred at room temperature for 6 hours, when additional 4M NaOH (0.64 ml, 2.6 mmol) was added and the reaction was continued for 64 hours. The reaction was then acidified with HCl, and concentrated. The crude product was triturated with MeOH to yield Compound 47 as an off-white solid (24 mg, 41%).

1H NMR (METHANOL-d4) δ: 8.28 (d, J=2.1 Hz, 1H), 8.00 (d, J=2.3 Hz, 1H), 7.81 (dd, J=7.8, 1.3 Hz, 1H), 7.64 (d, J=7.9 Hz, 1H), 7.43 (d, J=3.5 Hz, 2H), 7.37 (s, 1H), 7.27-7.34 (m, 1H), 7.12 (t, J=7.6 Hz, 1H), 6.99 (td, J=7.6, 1.5 Hz, 1H), 6.50 (d, J=8.2 Hz, 1H).

EXAMPLE 97

Intermediate 52 methyl 3-((5-chloro 3-nitropyridin-2-yl)thio)benzoate

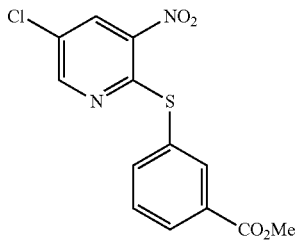 [SMILES: COC(=O)c1cccc(Sc2ncc(Cl)cc2[N+](=O)[O-])c1]

To a solution of 2,5-dichloro-3-nitropyridine (1.15 g, 5.96 mmol) in MeOH (10 ml) was added methyl 3-mercaptobenzoate (1.0 g, 5.96 mmol) and 4M NaOH (1.5 ml, 6.0 mmol) and the reaction was stirred at room temperature for 2 hours. The resulting suspension was diluted with H₂O, and it was filtered to give Intermediate 52 as yellow solid (1.94 g). The crude product was used in the next reaction without further purification.

EXAMPLE 98

Intermediate 53 methyl 3-((3-amino-5-chloropyridin-2-yl)thio)benzoate

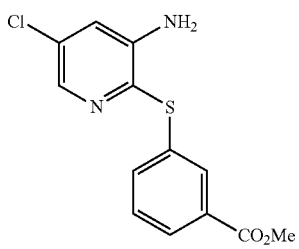 [SMILES: COC(=O)c1cccc(Sc2ncc(Cl)cc2N)c1]

To a solution of Intermediate 53 (324 mg, 1.0 mmol) in MeOH (15 ml) and THF (15 ml) was added saturated aqueous NH₄Cl (20 ml) and zinc dust (1.63 g, 25 mmol). The suspension was stirred at room temperature for 1 hour and was filtered, the filtrate was extracted with EtOAc. The organic layer was washed with brine, dried over Na₂SO₄, and concentrated in vacuo. The crude product was purified by flash column chromatography on silica gel (20-30% EtOAc in hexanes) to yield Intermediate 53 (250 mg, 85%).

¹H NMR (METHANOL-d4) δ: 7.82-7.86 (m, 1H), 7.79 (dt, J=7.6, 1.5 Hz, 1H), 7.73 (d, J=2.1 Hz, 1H), 7.41 (dt, J=8.0, 1.4 Hz, 1H), 7.33 (t, J=7.6 Hz, 1H), 7.16 (d, J=2.3 Hz, 1H), 3.83 (s, 3H).

EXAMPLE 99

Intermediate 54 methyl 3-((3-(benzofuran-2-sulfonamido)-5-chloropyridin-2-yl)thio)benzoate

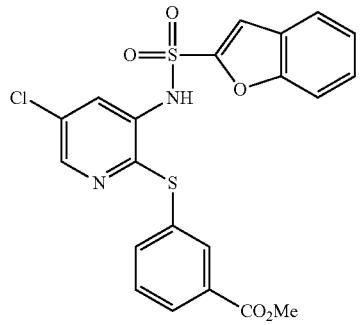 [SMILES: COC(=O)c1cccc(Sc2ncc(Cl)cc2NS(=O)(=O)c2cc3ccccc3o2)c1]

To Intermediate 53 (222 mg, 0.76 mmol) in pyridine (4 ml) was added benzofuran-2-sulfonyl chloride (164 mg, 0.76 mmol) and a catalytic amount of DMAP. The reaction was stirred at 100° C. for a total of 42 hours, during which additional benzofuran-2-sulfonyl chloride (410 mg, 1.9 mmol) was added in three batches to drive the reaction toward completion. At the end the reaction was concentrated, acidified with 6M HCl, diluted with brine and extracted with EtOAc (×2). The combined organic layer was dried over Na₂SO₄ and concentrated in vacuo. The residue was purified by flash column chromatography on silica gel (20% EtOAc in hexanes) to yield Intermediate 54 (275 mg, 77%).

¹H NMR (CHLOROFORM-d) δ: 8.23 (d, J=2.3 Hz, 1H), 8.01 (d, J=2.3 Hz, 1H), 7.84-7.90 (m, 2H), 7.68 (s, 1H), 7.65 (dt, J=7.8, 1.1 Hz, 1H), 7.44-7.48 (m, 2H), 7.41 (d, J=0.6 Hz, 1H), 7.30-7.37 (m, 1H), 7.21-7.25 (m, 2H), 3.87 (s, 3H).

EXAMPLE 100

Compound 48

3-({3-[(1-benzofuran-2-ylsulfonyl)amino]-5-chloropyridin-2-yl}sulfanyl)benzoic acid

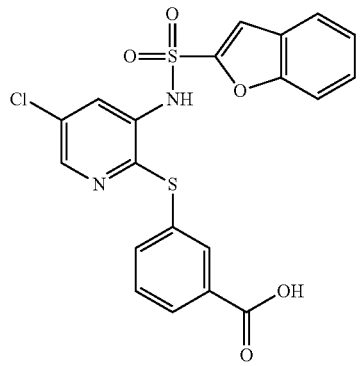 [SMILES: O=C(O)c1cccc(Sc2ncc(Cl)cc2NS(=O)(=O)c2cc3ccccc3o2)c1]

To a solution of Intermediate 54 (96 mg, 0.20 mmol) in MeOH (8 ml) was added 4M NaOH (0.25 ml, 1.0 mmol) and the reaction was stirred at room temperature for 6 hours, when an additional 4M NaOH (1.0 ml, 4.0 mmol) was added and the reaction was continued for 64 hours. The reaction was then acidified with HCl, concentrated. The crude product was triturated with H₂O to yield Compound 48 as an off-white solid (93 mg, 100%).

¹H NMR (METHANOL-d4) δ: 8.18 (d, J=2.1 Hz, 1H), 7.89 (d, J=7.6 Hz, 1H), 7.80 (d, J=2.3 Hz, 1H), 7.67-7.75 (m, 2H), 7.52-7.59 (m, 1H), 7.47 (t, J=7.8 Hz, 1H), 7.24-7.41 (m, 3H), 7.14 (d, J=7.9 Hz, 1H).

EXAMPLE 101

Compound 49 methyl 2-((3-(benzofuran-2-sulfonamido)-5-chloro-pyridin-2-yl)sulfinyl)benzoate

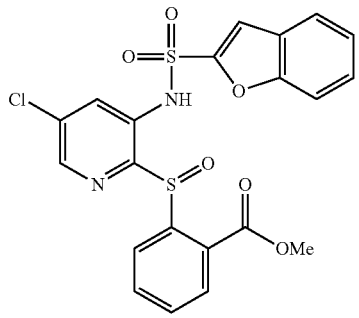 [SMILES: COC(=O)c1ccccc1S(=O)c1ncc(Cl)cc1NS(=O)(=O)c1cc2ccccc2o1]

To a solution of Intermediate 51 (58 mg, 0.12 mmol) in CH₂Cl₂ (2 ml) was added mCPBA (29 mg, ~0.12 mmol) and the reaction was stirred at room temperature for 2 hours and was concentrated. The residue was purified by flash column chromatography on silica gel (100% EtOAc) to yield Compound 49 (56 mg, 93%).

¹H NMR (acetone) δ: 8.10-8.23 (m, 2H), 8.06 (d, J=6.2 Hz, 1H), 7.54-7.71 (m, 4H), 7.46-7.54 (m, 1H), 7.32-7.44 (m, 2H), 7.23-7.32 (m, 1H), 3.61 (s, 3H).

EXAMPLE 102

Compound 50

2-({3-[(1-benzofuran-2-ylsulfonyl)amino]-5-chloro-pyridin-2-yl}sulfinyl)benzoic acid

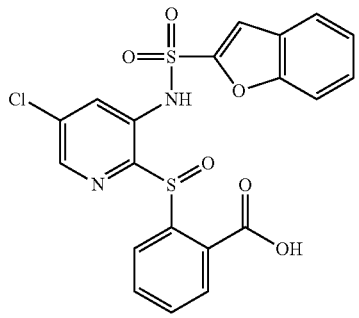 [SMILES: O=C(O)c1ccccc1S(=O)c1ncc(Cl)cc1NS(=O)(=O)c1cc2ccccc2o1]

To a solution of Compound 49 (55 mg, 0.11 mmol) in MeOH (5 ml) was added 4M NaOH (0.7 ml, 2.8 mmol) and the reaction was stirred at room temperature for 16 hours. The reaction was then acidified with HCl and was concentrated. The crude product was triturated with H₂O to yield Compound 50 as yellow solid (46 mg, 87%).

¹H NMR (CHLOROFORM-d) δ: 9.54 (br. s., 1H), 8.37 (d, J=8.2 Hz, 1H), 8.19 (d, J=2.1 Hz, 1H), 8.09 (d, J=2.1 Hz, 1H), 8.04 (dd, J=7.5, 1.0 Hz, 1H), 7.77-7.85 (m, 1H), 7.65 (d, J=7.9 Hz, 1H), 7.52-7.61 (m, 2H), 7.49 (s, 1H), 7.44 (td, J=7.8, 1.3 Hz, 1H), 7.30 (d, J=7.9 Hz, 1H).

EXAMPLE 103

Compound 51 methyl 2-((3-(benzofuran-2-sulfonamido)-5-chloro-pyridin-2-yl)sulfonyl)benzoate

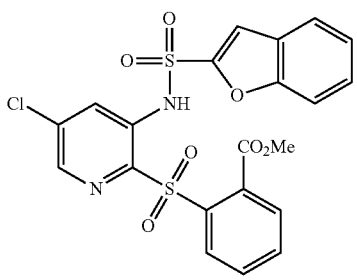 [SMILES: COC(=O)c1ccccc1S(=O)(=O)c1ncc(Cl)cc1NS(=O)(=O)c1cc2ccccc2o1]

To a solution of Intermediate 51 (58 mg, 0.12 mmol) in CH₂Cl₂ (2 ml) was added mCPBA (59 mg, ~0.25 mmol) and the reaction was stirred at room temperature for 2 hours and additional mCPBA (30 mg, ~0.12 mmol) was added. The reaction was continued for 4 hours and was diluted with saturated aqueous NaHCO₃, extracted with EtOAc. The organic layer was washed with brine, dried over Na₂SO₄, and concentrated in vacuo. The residue was purified by flash column chromatography on silica gel (50% EtOAc in hexanes) to yield Compound 51 (45 mg, 73%).

¹H NMR (acetone) δ: 8.13-8.21 (m, 1H), 8.08 (br. s., 1H), 7.51-7.74 (m, 5H), 7.11-7.47 (m, 5H), 3.50 (br. s., 3H).

EXAMPLE 104

Compound 52

2-({3-[(1-benzofuran-2-ylsulfonyl)amino]-5-chloro-pyridin-2-yl}sulfonyl)benzoic acid

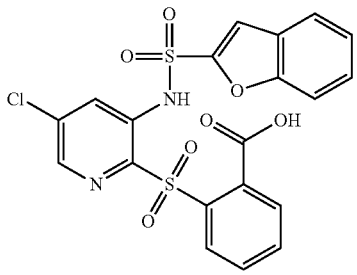 [SMILES: O=C(O)c1ccccc1S(=O)(=O)c1ncc(Cl)cc1NS(=O)(=O)c1cc2ccccc2o1]

To a solution of Compound 51 (45 mg, 0.089 mmol) in MeOH (5 ml) was added 4M NaOH (0.56 ml, 2.2 mmol) and the reaction was stirred at room temperature for 2 days. The reaction was then acidified with HCl and was concentrated. The crude product was triturated with $H_2O$ and was further purified by PTLC (developed with EtOAc) to yield Compound 52 as white solid (20 mg, 45%).

$^1$H NMR (CHLOROFORM-d) δ: 9.77 (s, 1H), 8.42-8.45 (m, 1H), 8.30 (d, J=2.1 Hz, 1H), 8.11 (d, J=2.1 Hz, 1H), 8.04-8.06 (m, 1H), 7.76-7.79 (m, 2H), 7.68-7.70 (m, 1H), 7.58-7.60 (m, 1H), 7.55 (d, J=0.9 Hz, 1H), 7.49 (ddd, J=8.5, 7.2, 1.3 Hz, 1H), 7.35 (ddd, J=7.9, 7.0, 0.9 Hz, 1H).

EXAMPLE 106

Intermediate 55 methyl 2-(((5-methyl-3-nitropyridin-2-yl)thio)methyl)benzoate

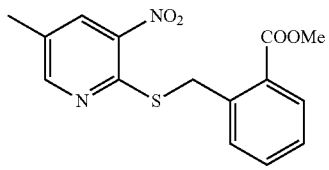 [SMILES: COC(=O)c1ccccc1CSc1ncc(C)cc1[N+](=O)[O-]]

To the crude Intermediate 54 in DMF (10 ml) was added methyl 2-(bromomethyl)benzoate (1.4 g, 6.20 mmol) and $K_2CO_3$ (2.5 g, 18.11 mmol) and the reaction was stirred at room temperature for 16 hours. The reaction mixture was poured into water (50 ml) and extracted with ethyl acetate (2×50 ml). The organic layer was washed with brine and then dried over $Na_2SO_4$ anhydride, concentrated in vacuo and purified by flash column chromatography on silica gel (0~30% ethyl acetate in hexane) to give Intermediate 55 (555 mg, 31%).

$^1$H NMR (300 MHz, CDCl$_3$) δ 8.53 (d, J=1.47 Hz, 1H), 8.28 (d, J=1.47 Hz, 1H), 7.92 (dd, J=1.17, 7.91 Hz, 1H), 7.59 (d, J=7.62 Hz, 1H), 7.42 (td, J=1.32, 7.55 Hz, 1H), 7.21-7.35 (m, 1H), 4.88 (s, 2H), 3.93 (s, 3H), 2.39 (s, 3H).

EXAMPLE 107

Intermediate 56 methyl 2-(((3-amino-5-methylpyridin-2-yl)thio)methyl)benzoate

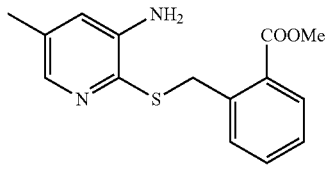

To a solution Intermediate 55 (555 mg, 1.94 mmol) in MeOH (20 ml) was added saturated aqueous $NH_4Cl$ (2 ml) and zinc dust (3.2 g, 63.71 mmol). The suspension was stirred at room temperature for 1 hour and was filtered, and the filtrate was extracted with EtOAc (×2). The organic layer was washed with brine, dried over $Na_2SO_4$, and concentrated in vacuo. The crude Intermediate 56 (406 mg, 81%) was used in the next reaction without further purification.

$^1$H NMR (300 MHz, CD$_3$OD) δ 7.83 (dd, J=1.47, 7.62 Hz, 1H), 7.65 (d, J=1.17 Hz, 1H), 7.13-7.38 (m, 3H), 6.83 (d, J=1.17 Hz, 1H), 4.58 (s, 2H), 3.86 (s, 3H), 2.18 (s, 3H).

EXAMPLE 108

Intermediate 57 methyl 2-(((3-(benzofuran-2-sulfonamido)-5-methylpyridin-2-yl)thio)methyl)benzoate

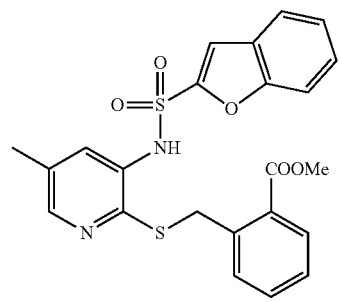 [SMILES: COC(=O)c1ccccc1CSc1ncc(C)cc1NS(=O)(=O)c1cc2ccccc2o1]

To Intermediate 56 (406 mg, 1.41 mmol) in pyridine (5 ml) was added benzofuran-2-sulfonyl chloride (305 mg, 1.41 mmol), and the reaction was stirred at 100° C. for 16 hours and concentrated in vacuo. The crude product was purified by flash column chromatography on silica gel (0-30% EtOAc in hexanes) to yield Intermediate 57 (270 mg, 41%).

$^1$H NMR (600 MHz, CDCl$_3$) δ 8.15 (dd, J=0.59, 2.05 Hz, 0H), 7.88 (dd, J=1.61, 7.48 Hz, 0H), 7.65-7.70 (m, 1H), 7.63-7.65 (m, 0H), 7.59 (ddd, J=0.88, 1.03, 8.07 Hz, 0H), 7.43 (dd, J=1.17, 6.75 Hz, 0H), 7.21-7.31 (m, 4H), 7.17 (dd, J=1.61, 7.48 Hz, 1H), 4.63 (s, 2H), 3.91 (s, 3H), 2.30 (s, 3H).

EXAMPLE 109

Compound 53

2-[({3-[(1-benzofuran-2-ylsulfonyl)amino]-5-methylpyridin-2-yl}sulfanyl)methyl]benzoic acid

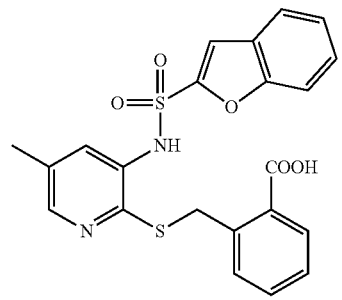 [SMILES: Cc1cnc(SCc2ccccc2C(=O)O)c(NS(=O)(=O)c2cc3ccccc3o2)c1]

To Intermediate 57 (136 mg, 0.29 mmol) in MeOH (30 ml) was added 5N NaOH (2 ml) and the reaction was stirred at room temperature for 3 hours. The mixture was acidified with 10% HCl, extracted with EtOAc (×2). The combined organic layer was washed with brine, dried over $Na_2SO_4$, and concentrated in vacuo. The crude product was recrystallized from minimal MeOH and CH$_2$Cl$_2$ to yield Compound 53 (108 mg, 82%).

$^1$H NMR (600 MHz, CDCl$_3$) δ 8.05 (s, 1H), 7.80 (dd, J=1.47, 7.63 Hz, 1H), 7.69 (s, 1H), 7.62 (d, J=7.92 Hz, 1H), 7.52-7.56 (m, 1H), 7.49 (td, J=1.32, 7.85 Hz, 1H), 7.33-7.37 (m, J=7.48, 7.48 Hz, 1H), 7.28 (d, J=0.88 Hz, 1H), 7.23 (td, J=1.17, 7.48 Hz, 1H), 7.18 (td, J=1.47, 7.48 Hz, 1H), 7.10 (d, J=7.63 Hz, 1H), 7.03 (br. s., 1H), 4.47 (s, 2H), 2.29 (s, 3H).

EXAMPLE 110

Compound 54 methyl 2-(((3-(benzofuran-2-sulfonamido)-5-methylpyridin-2-yl)sulfinyl)methyl)benzoate

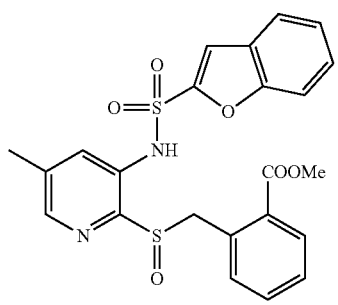 [SMILES: COC(=O)c1ccccc1CS(=O)c1ncc(C)cc1NS(=O)(=O)c1cc2ccccc2o1]

To a solution of Intermediate 57 (134 mg, 0.29 mmol) in CH$_2$Cl$_2$ (5 ml) was added mCPBA (57 mg, 0.29 mmol) and the reaction was stirred at 0° C. for 30 mins and was concentrated. The residue was purified by flash column chromatography on silica gel (100% EtOAc) to yield Compound 54 (82 mg, 59%).

$^1$H NMR (600 MHz, CDCl$_3$) δ 10.84 (br. s., 1H), 8.07 (d, J=1.17 Hz, 1H), 7.98 (dd, J=1.32, 7.78 Hz, 1H), 7.87 (s, 1H), 7.65 (d, J=7.92 Hz, 1H), 7.44-7.48 (m, 2H), 7.38-7.43 (m, 2H), 7.34-7.38 (m, 1H), 7.27-7.32 (m, 1H), 7.01-7.09 (m, 1H), 4.98 (d, J=12.32 Hz, 1H), 4.63 (d, J=12.32 Hz, 1H), 3.87 (s, 3H), 2.36 (s, 3H).

EXAMPLE 111

Compound 55

2-[({3-[(1-benzofuran-2-ylsulfonyl)amino]-5-methylpyridin-2-yl}sulfinyl)methyl]benzoic acid

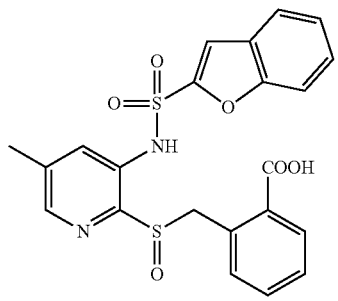

To Compound 54 (505 mg, 1.04 mmol) in MeOH (30 ml) was added 5N NaOH (2 ml) and the reaction was stirred at room temperature for 16 hours. The mixture was acidified with 10% HCl, and extracted with EtOAc (×2). The combined organic layer was washed with brine, dried over Na$_2$SO$_4$, and concentrated in vacuo. The crude product was recrystallized from minimal MeOH and CH$_2$Cl$_2$ to yield Compound 55 (454 mg, 93%).

$^1$H NMR (600 MHz, CDCl$_3$) δ 8.05-8.16 (m, 2H), 7.90 (s, 1H), 7.68 (dd, J=0.73, 7.78 Hz, 1H), 7.37-7.52 (m, 5H), 7.33 (td, J=1.03, 7.56 Hz, 1H), 7.04 (d, J=7.34 Hz, 1H), 4.97 (d, J=11.74 Hz, 1H), 4.63 (d, J=12.03 Hz, 1H), 2.41 (s, 3H).

EXAMPLE 112

Intermediate 58 methyl 2-(((3-nitropyridin-2-yl)thio)methyl)benzoate

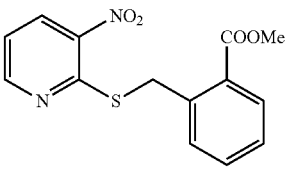 [SMILES: COC(=O)c1ccccc1CSc1ncccc1[N+](=O)[O-]]

To 3-nitropyridine-2-thiol (1 g, 6.40 mmol) in DMF (10 ml) was added methyl 2-(bromomethyl)benzoate (1.5 g, 6.40 mmol) and K$_2$CO$_3$ (2.6 g, 19.21 mmol) and the reaction was stirred at room temperature for 16 hours. The reaction mixture was poured into water (50 ml) and extracted with ethyl acetate (2×50 ml). The organic layer was washed with brine and then dried over Na$_2$SO$_4$, concentrated in vacuo and purified by flash column chromatography on silica gel (0~30% ethyl acetate in hexane) to give Intermediate 58 (1.12 g, 57%).

$^1$H NMR (600 MHz, CDCl$_3$) δ 8.70 (dd, J=1.61, 4.55 Hz, 1H), 8.47 (dd, J=1.47, 8.22 Hz, 1H), 7.95 (dd, J=1.17, 7.63 Hz, 1H), 7.62 (d, J=7.92 Hz, 1H), 7.44 (td, J=1.32, 7.56 Hz, 1H), 7.29-7.36 (m, 1H), 7.19 (dd, J=4.55, 8.36 Hz, 1H), 4.92 (s, 2H), 3.94 (s, 3H).

EXAMPLE 113

Intermediate 59 methyl 2-(((3-aminopyridin-2-yl)thio)methyl)benzoate

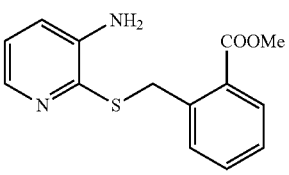

To a solution of Intermediate 58 (555 mg, 3.68 mmol) in MeOH (20 ml) was added saturated aqueous NH$_4$Cl (2 ml) and zinc dust (4.8 g, 73.68 mmol). The suspension was stirred at room temperature for 1 hour and was filtered, the filtrate was extracted with EtOAc (×2). The organic layer was washed with brine, dried over Na$_2$SO$_4$, and concentrated in vacuo. Intermediate 59 (988 mg, 98%) was used in the next reaction without further purification.

¹H NMR (600 MHz, CDCl₃) δ 8.15 (dd, J=0.59, 2.05 Hz, 1H), 7.88 (dd, J=1.61, 7.48 Hz, 1H), 7.65-7.70 (m, 1H), 7.63-7.65 (m, 1H), 7.59 (ddd, J=0.88, 1.03, 8.07 Hz, 1H), 7.43 (dd, J=1.17, 6.75 Hz, 1H), 7.21-7.31 (m, 4H), 7.17 (dd, J=1.61, 7.48 Hz, 1H), 4.63 (s, 2H), 3.91 (s, 3H), 2.30 (s, 3H).

EXAMPLE 114

Compound 56 methyl 2-[({3-[(1-benzofuran-2-ylsulfonyl)amino]pyridin-2-yl}sulfanyl)methyl]benzoate

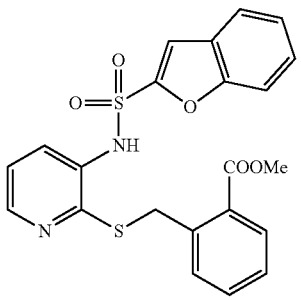 [SMILES: COC(=O)c1ccccc1CSc1ncccc1NS(=O)(=O)c1cc2ccccc2o1]

To Intermediate 59 (968 mg, 3.53 mmol) in pyridine (5 ml) was added benzofuran-2-sulfonyl chloride (763 mg, 1.41 mmol) and the reaction was stirred at 100° C. for 16 hours, then additional of benzofuran-2-sulfonyl chloride (763 mg, 1.41 mmol) and DMAP (cat.) was added and the reaction was further stirred at 100° C. for 16 hours and concentrated in vacuo. The crude product was purified by flash column chromatography on silica gel (0-30% EtOAc in hexanes) to yield Compound 56 (745 mg, 46%).

¹H NMR (600 MHz, CDCl₃) δ 8.55 (br. s., 1H), 8.24 (dd, J=1.47, 4.70 Hz, 1H), 7.81 (d, J=7.92 Hz, 1H), 7.71 (dd, J=1.61, 8.07 Hz, 1H), 7.50-7.53 (m, 1H), 7.31-7.40 (m, 2H), 7.13-7.25 (m, 5H), 6.99 (dd, J=4.70, 8.22 Hz, 1H), 4.62 (s, 2H), 3.83 (s, 3H).

EXAMPLE 115

Compound 57

2-[({3-[(1-benzofuran-2-ylsulfonyl)amino]pyridin-2-yl}sulfanyl)methyl]benzoic acid

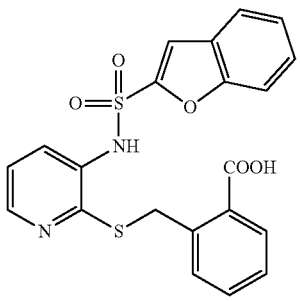 [SMILES: O=C(O)c1ccccc1CSc1ncccc1NS(=O)(=O)c1cc2ccccc2o1]

To Compound 56 (170 mg, 0.37 mmol) in MeOH (30 ml) was added 5N NaOH (2 ml) and stirred at room temperature for 3 hours. The mixture was acidified with 10% HCl, extracted with EtOAc (×2). The combined organic layer was washed with brine, dried over Na₂SO₄, and concentrated in vacuo. The crude product was recrystallized from minimal MeOH and CH₂Cl₂ to yield Compound 57 (165 mg, 100%).

¹H NMR (600 MHz, CDCl₃) δ 8.33 (br. s., 1H), 7.89 (none, 1H), 7.86-7.91 (m, 1H), 7.78 (d, J=7.92 Hz, 1H), 7.60 (d, J=7.92 Hz, 0H), 7.42-7.48 (m, 2H), 7.29-7.35 (m, 2H), 7.22-7.26 (m, 3H), 7.16-7.20 (m, 1H), 7.13 (br. s., 1H), 4.64 (s, 2H).

EXAMPLE 116

Compound 58 methyl 2-[({3-[(1-benzofuran-2-ylsulfonyl)amino]pyridin-2-Yl}sulfinyl)methyl]benzoate

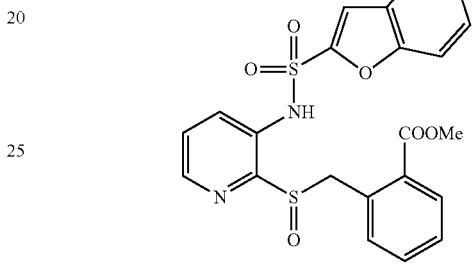

To a solution of Compound 56 (180 mg, 0.40 mmol) in CH₂Cl₂ (5 ml) was added mCPBA (80 mg, 0.40 mmol) and the reaction was stirred at 0° C. for 30 mins and was concentrated. The residue was purified by flash column chromatography on silica gel (100% EtOAc) to yield Compound 58 (180 mg, 96%).

¹H NMR (600 MHz, CDCl₃) δ 8.22 (ddd, J=1.32, 1.47, 4.55 Hz, 1H), 8.03-8.08 (m, 1H), 7.96 (dd, J=1.47, 7.63 Hz, 1H), 7.63 (dd, J=0.59, 7.92 Hz, 1H), 7.22-7.49 (m, 7H), 7.01 (d, J=7.63 Hz, 1H), 5.02 (d, J=12.32 Hz, 1H), 4.66 (d, J=12.32 Hz, 1H), 3.86 (s, 3H).

EXAMPLE 117

Compound 59

2-[({3-[(1-benzofuran-2-ylsulfonyl)amino]pyridin-2-yl}sulfinyl)methyl]benzoic acid

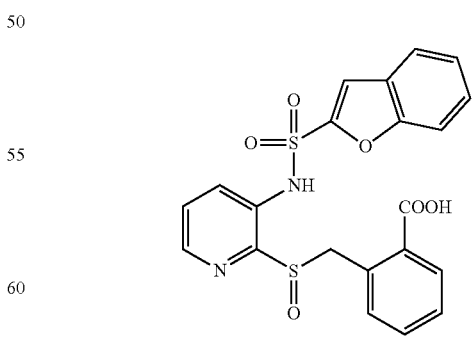

To Compound 58 (189 mg, 0.40 mmol) in MeOH (30 ml) was added 5N NaOH (2 ml) and stirred at room temperature for 3 hours. The mixture was acidified with 10% HCl, extracted with EtOAc (×2). The combined organic layer was washed with brine, dried over Na$_2$SO$_4$, and concentrated in vacuo. The crude product was recrystallized from minimal MeOH and CH$_2$Cl$_2$ to yield Compound 59 (140 mg, 76%).

$^1$H NMR (600 MHz, CD$_3$OD) δ 8.30 (d, J=3.52 Hz, 1H), 7.95-8.02 (m, 1H), 7.84 (s, 1H), 7.72 (d, J=7.92 Hz, 1H), 7.51-7.57 (m, 2H), 7.41-7.49 (m, 2H), 7.29-7.37 (m, 3H), 6.83-6.92 (m, 1H), 4.96 (d, J=12.32 Hz, 1H), 4.80 (d, J=12.32 Hz, 1H).

EXAMPLE 118

Compound 60 methyl 2-[({3-[(1-benzofuran-2-ylsulfonyl)amino]pyridin-2-yl}sulfonyl)methyl]benzoate

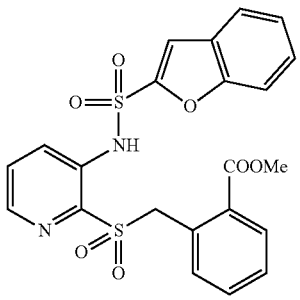 [SMILES: COC(=O)c1ccccc1CS(=O)(=O)c1ncccc1NS(=O)(=O)c1cc2ccccc2o1]

To a solution of Compound 56 (180 mg, 0.40 mmol) in CH$_2$Cl$_2$ (5 ml) was added mCPBA (200 mg, 0.99 mmol) and the reaction was stirred at room temperature for 2 hours and was concentrated. The residue was purified by flash column chromatography on silica gel (100% EtOAc) to yield Compound 60 (186 mg, 97%).

$^1$H NMR (600 MHz, CDCl$_3$) δ 9.62 (br. s., 1H), 8.39 (d, J=4.40 Hz, 1H), 8.19 (d, J=8.80 Hz, 1H), 7.89 (d, J=7.92 Hz, 1H), 7.63 (d, J=7.92 Hz, 1H), 7.41-7.51 (m, 4H), 7.33-7.38 (m, 1H), 7.27-7.32 (m, 2H), 7.18 (d, J=7.34 Hz, 1H), 5.31 (s, 2H), 3.86 (s, 3H).

EXAMPLE 119

Compound 61

2-[({3-[(1-benzofuran-2-ylsulfonyl)amino]pyridin-2-yl}sulfonyl)methyl]benzoic acid

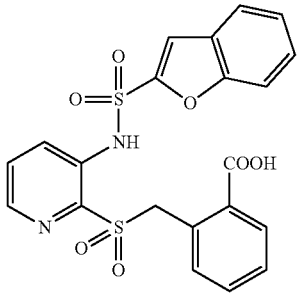 [SMILES: O=C(O)c1ccccc1CS(=O)(=O)c1ncccc1NS(=O)(=O)c1cc2ccccc2o1]

To Compound 60 (119 mg, 0.24 mmol) in MeOH (30 ml) was added 5N NaOH (2 ml) and the reaction was stirred at room temperature for 3 hours. The mixture was acidified with 10% HCl, extracted with EtOAc (×2). The combined organic layer was washed with brine, dried over Na$_2$SO$_4$, and concentrated in vacuo. The crude product was recrystallized from minimal MeOH and CH$_2$Cl$_2$ to yield Compound 61 (98 mg, 85%).

$^1$H NMR (600 MHz, CD$_3$OD) δ 8.41 (dd, J=1.17, 4.40 Hz, 1H), 8.20 (dd, J=1.32, 8.66 Hz, 1H), 7.86 (dd, J=1.32, 7.78 Hz, 1H), 7.73 (d, J=7.92 Hz, 1H), 7.63 (dd, J=4.40, 8.51 Hz, 1H), 7.58 (d, J=0.88 Hz, 1H), 7.53-7.56 (m, 1H), 7.48-7.53 (m, 1H), 7.36 (td, J=1.03, 7.56 Hz, 1H), 7.29-7.33 (m, 1H), 7.23 (td, J=1.47, 7.63 Hz, 1H), 7.13 (dd, J=0.88, 7.63 Hz, 1H), 5.39 (s, 2H).

BIOLOGICAL DATA

HEK-Gqi5 cells stably expressing CCR2 were cultured in (DMEM high glucose, 10% FBS, 1% PSA, 400 μg/ml geneticin and 50 μg/ml hygromycin. Appropriate positive control chemokines (MCP-1, MIP1A or RANTES) was used as the positive control agonist for screening compound-induced calcium activity assayed on the FLIPR$^{Tetra}$. The drug plates were prepared in 384-well microplates using the EP3 and the MultiPROBE robotic liquid handling systems. Compounds were synthesized and tested for CCR2 activity.

Table 1 shows activity: CCR2 receptor (IC$_{50}$) nM

TABLE 1

| IUPAC Name | IC50 (nM) | % ANTAGONISM |
|---|---|---|
| N-[2-(benzylsulfanyl)-5-chloropyridin-3-yl]-1-benzofuran-2-sulfonamide | 252 | 83 |
| N-[2-(benzylsulfinyl)-5-chloropyridin-3-yl]-1-benzofuran-2-sulfonamide | 31 | 94 |
| N-[2-(benzylsulfonyl)-5-chloropyridin-3-yl]-1-benzofuran-2-sulfonamide | 19 | 90 |
| N-{5-chloro-2-[(pyridin-3-ylmethyl)sulfanyl]pyridin-3-yl}-1-benzofuran-2-sulfonamide | 32 | 95 |
| N-{5-chloro-2-[(pyridin-3-ylmethyl)sulfinyl]pyridin-3-yl}-1-benzofuran-2-sulfonamide | 201 | 99 |
| N-{5-chloro-2-[(pyridin-3-ylmethyl)sulfonyl]pyridin-3-yl}-1-benzofuran-2-sulfonamide | 2142 | 84 |
| N-(5-chloro-2-{[(1-oxidopyridin-3-yl)methyl]sulfonyl}pyridin-3-yl)-1-benzofuran-2-sulfonamide | 130 | 100 |
| N-[2-(benzylsulfanyl)pyridin-3-yl]-1-benzofuran-2-sulfonamide | 3012 | 80 |
| N-[2-(benzylsulfinyl)pyridin-3-yl]-1-benzofuran-2-sulfonamide | 27 | 100 |
| N-[2-(benzylsulfonyl)pyridin-3-yl]-1-benzofuran-2-sulfonamide | 16 | 95 |
| N-{2-[(3-aminobenzyl)sulfanyl]pyridin-3-yl}-1-benzofuran-2-sulfonamide | 102 | 99 |
| N-{2-[(3-aminobenzyl)sulfinyl]pyridin-3-yl}-1-benzofuran-2-sulfonamide | 255 | 100 |
| tert-butyl {3-[({3-[(1-benzofuran-2-ylsulfonyl)amino]pyridin-2-yl}sulfonyl)methyl]phenyl}carbamate | 497 | 102 |
| N-{2-[(3-aminobenzyl)sulfonyl]pyridin-3-yl}-1-benzofuran-2-sulfonamide | 71 | 102 |
| N-[2-(benzylsulfanyl)-5-fluoropyridin-3-yl]-1-benzofuran-2-sulfonamide | 125 | 94 |
| N-[2-(benzylsulfinyl)-5-fluoropyridin-3-yl]-1-benzofuran-2-sulfonamide | 18 | 95 |
| N-[2-(benzylsulfonyl)-5-fluoropyridin-3-yl]-1-benzofuran-2-sulfonamide | 43 | 101 |
| N-{2-[(3-aminobenzyl)sulfanyl]-5-chloropyridin-3-yl}-1-benzofuran-2-sulfonamide | 95 | 98 |
| N-{2-[(3-aminobenzyl)sulfinyl]-5-chloropyridin-3-yl}-1-benzofuran-2-sulfonamide | 101 | 97 |

TABLE 1-continued

| IUPAC Name | IC50 (nM) | % ANTAGONISM |
|---|---|---|
| N-{2-[(3-aminobenzyl)sulfonyl]-5-chloropyridin-3-yl}-1-benzofuran-2-sulfonamide | 142 | 100 |
| N-[2-(benzylsulfanyl)-5-methylpyridin-3-yl]-1-benzofuran-2-sulfonamide | 194 | 80 |
| N-[2-(benzylsulfinyl)-5-methylpyridin-3-yl]-1-benzofuran-2-sulfonamide | 25 | 103 |
| N-[2-(benzylsulfonyl)-5-methylpyridin-3-yl]-1-benzofuran-2-sulfonamide | 12 | 96 |
| N-{5-chloro-2-[(2-methylpyridin-3-yl)oxy]pyridin-3-yl}-1-benzofuran-2-sulfonamide | 34 | 90 |
| 2-({3-[(1-benzofuran-2-ylsulfonyl)amino]-5-chloropyridin-2-yl}oxy)benzoic acid | 157 | 97 |
| methyl 2-({3-[(1-benzofuran-2-ylsulfonyl)amino]-5-chloropyridin-2-yl}oxy)benzoate | 215 | 93 |
| N-{5-chloro-2-[(4-oxopiperidin-1-yl)carbonyl]pyridin-3-yl}-1-benzofuran-2-sulfonamide | 24 | 105 |
| N-[5-chloro-2-(phenylcarbonyl)pyridin-3-yl]-1-benzofuran-2-sulfonamide | 36 | 100 |
| N-[5-chloro-2-(phenylsulfonyl)pyridin-3-yl]-1-benzofuran-2-sulfonamide | 17 | 105 |
| N-[5-chloro-2-(phenylsulfinyl)pyridin-3-yl]-1-benzofuran-2-sulfonamide | 7 | 99 |
| N-{5-chloro-2-[(2-methylpyridin-3-yl)methoxy]pyridin-3-yl}-1-benzofuran-2-sulfonamide | 251 | 102 |
| methyl 2-[({3-[(1-benzofuran-2-ylsulfonyl)amino]-5-chloropyridin-2-yl}sulfanyl)methyl]benzoate | 4252 | 91 |
| 2-[({3-[(1-benzofuran-2-ylsulfonyl)amino]-5-chloropyridin-2-yl}sulfanyl)methyl]benzoic acid | 340 | 97 |
| methyl 2-[({3-[(1-benzofuran-2-ylsulfonyl)amino]-5-chloropyridin-2-yl}sulfinyl)methyl]benzoate | 191 | 95 |
| methyl 2-[({3-[(1-benzofuran-2-ylsulfonyl)amino]-5-chloropyridin-2-yl}sulfonyl)methyl]benzoate | 180 | 97 |
| 2-[({3-[(1-benzofuran-2-ylsulfonyl)amino]-5-chloropyridin-2-yl}sulfonyl)methyl]benzoic acid | 2691 | 32 |
| N-[5-fluoro-2-(phenylsulfanyl)pyridin-3-yl]-1-benzofuran-2-sulfonamide | 469 | 65 |
| N-[5-fluoro-2-(phenylsulfinyl)pyridin-3-yl]-1-benzofuran-2-sulfonamide | 68 | 97 |
| 2-[({3-[(1-benzofuran-2-ylsulfonyl)amino]-5-chloropyridin-2-yl}sulfinyl)methyl]benzoic acid | nd | 90 |
| N-[5-methyl-2-(phenylsulfinyl)pyridin-3-yl]-1-benzofuran-2-sulfonamide | 455 | 105 |
| N-[5-methyl-2-(phenylsulfonyl)pyridin-3-yl]-1-benzofuran-2-sulfonamide | 1436 | 57 |
| 2-({3-[(1-benzofuran-2-ylsulfonyl)amino]-5-chloropyridin-2-yl}sulfanyl)benzoic acid | 1230 | 102 |
| 3-({3-[(1-benzofuran-2-ylsulfonyl)amino]-5-chloropyridin-2-yl}sulfanyl)benzoic acid | 786 | 96 |
| 2-({3-[(1-benzofuran-2-ylsulfonyl)amino]-5-chloropyridin-2-yl}sulfinyl)benzoic acid | 1951 | 5 |
| methyl 2-[({3-[(1-benzofuran-2-ylsulfonyl)amino]pyridin-2-yl}sulfanyl)methyl]benzoate | 1754 | 92 |
| 2-[({3-[(1-benzofuran-2-ylsulfonyl)amino]pyridin-2-yl}sulfanyl)methyl]benzoic acid | 493 | 98 |
| methyl 2-[({3-[(1-benzofuran-2-ylsulfonyl)amino]pyridin-2-yl}sulfinyl)methyl]benzoate | 198 | 102 |
| 2-[({3-[(1-benzofuran-2-ylsulfonyl)amino]pyridin-2-yl}sulfinyl)methyl]benzoic acid | nd | 58 |
| methyl 2-[({3-[(1-benzofuran-2-ylsulfonyl)amino]pyridin-2-yl}sulfonyl)methyl]benzoate | 86 | 101 |
| 2-[({3-[(1-benzofuran-2-ylsulfonyl)amino]pyridin-2-yl}sulfonyl)methyl]benzoic acid | nd | 57 |

What is claimed is:

1. A method of treating a disorder associated with chemokine receptor modulation, which comprises administering to a mammal in need thereof, a pharmaceutical composition comprising a therapeutically effective amount of at least one compound of Formula I

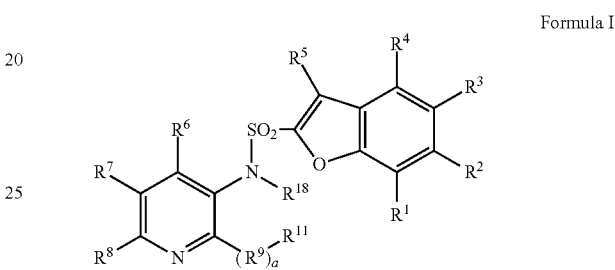

Formula I wherein:
$R^1$ is hydrogen, halogen, CN, substituted or unsubstituted $C_{1-6}$ alkyl, $OR^{12}$, $NR^{13}R^{14}$, or $COR^{15}$;
$R^2$ is hydrogen, halogen, CN, substituted or unsubstituted $C_{1-6}$ alkyl, $OR^{12}$, $NR^{13}R^{14}$, or $COR^{15}$;
$R^3$ is hydrogen, halogen, CN, substituted or unsubstituted $C_{1-6}$ alkyl, $OR^{12}$, $NR^{13}R^{14}$, or $COR^{15}$;
$R^4$ is hydrogen, halogen, CN, substituted or unsubstituted $C_{1-6}$ alkyl, $OR^{12}$, $NR^{13}R^{14}$, or $COR^{15}$;
$R^5$ is hydrogen, halogen, CN, substituted or unsubstituted $C_{1-6}$ alkyl, $OR^{12}$, $NR^{13}R^{14}$, or $COR^{15}$;
$R^6$ is hydrogen, halogen, CN, substituted or unsubstituted $C_{1-6}$ alkyl, $OR^{12}$, $NR^{13}R^{14}$, or $COR^{15}$;
$R^7$ is hydrogen, halogen, CN, substituted or unsubstituted $C_{1-6}$ alkyl, $OR^{12}$, $NR^{13}R^{14}$, or $COR^{15}$;
$R^8$ is hydrogen, halogen, CN, substituted or unsubstituted $C_{1-6}$ alkyl, $OR^{12}$, $NR^{13}R^{14}$, or $COR^{15}$;
$R^9$ is O, C(O), S, S(O), S(O)$_2$, —C(=NR$^{16}$)—;
a is 0 or 1;
$R^{11}$ is hydrogen, CN, substituted or unsubstituted $C_{1-6}$ alkyl, $CF_3$, $OR^{12}$, $NR^{13}R^{14}$, substituted or unsubstituted $C_{6-10}$ aryl, substituted or unsubstituted heterocycle, substituted or unsubstituted $C_{3-8}$ cycloalkyl, substituted or unsubstituted $C_{2-6}$ alkyne, substituted or unsubstituted $C_{2-6}$ alkene or $COR^{15}$;
$R^{12}$ is hydrogen or substituted or unsubstituted $C_{1-6}$ alkyl;
$R^{13}$ is hydrogen or substituted or unsubstituted $C_{1-6}$ alkyl or can from an optionally substituted heterocycle with $R^{14}$;
$R^{14}$ is hydrogen, substituted or unsubstituted $C_{1-6}$ alkyl, substituted or unsubstituted heterocycle or substituted or unsubstituted $C_{6-10}$ aryl or can from an optionally substituted heterocycle with $R^{13}$;
$R^{15}$ is hydrogen, hydroxyl, substituted or unsubstituted heterocycle, substituted or unsubstituted $C_{6-10}$ aryl or substituted or unsubstituted $C_{1-6}$ alkyl;
$R^{16}$ is hydrogen or substituted or unsubstituted $C_{1-6}$ alkyl; and $R^{18}$ is hydrogen or substituted or unsubstituted $C_{1-6}$ alkyl;
wherein the disorder associated with chemokine receptor modulation is:
- an ocular inflammatory disease selected from: uveitis, retinal degenerative conditions, angiogenesis, dry eye, Keratitis, allergic eye disease, conditions affecting the posterior part of the eye, retinal degeneration, non-exudative age related macular degeneration, exudative age related macular degeneration, choroidal neovascularization, diabetic retinopathy, acute macular neuroretinopathy, central serous chorioretinopathy, cystoid macular edema, and diabetic macular edema, retinitis, acute multifocal placoid pigment epitheliopathy, Behcet's disease, birdshot retinochoroidopathy, multifocal choroiditis, multiple evanescent white dot syndrome, ocular sarcoidosis, posterior scleritis, serpiginous choroiditis, subretinal fibrosis and Vogt-Koyanagi-and Harada syndrome; or
- a skin inflammatory disease selected from: rosacea, sunburn, chronic sun damage, discreet erythemas, psoriasis, atopic dermatitis, menopause-associated hot flashes, hot flashes resulting from orchiectomvatopic dermatitis, photoaging, seborrheic dermatitis, acne, allergic dermatitis, irritant dermatitis, telangiectasia of the face, rhinophyma, red bulbous nose, acne-like skin eruptions, burning or stinging sensation of the face, cutaneous hyperactivity with dilation of blood vessels of the skin, Lyell's syndrome, Stevens-Johnson syndrome, erythema multiforme minor, erythema multiforme, actinic keratoses, arsenic keratoses, inflammatory acne, non inflammatory acne, eczema and wound healing.

2. The method according to claim 1 wherein:
$R^1$ is hydrogen, halogen or substituted or unsubstituted $C_{1-6}$ alkyl;
$R^2$ is hydrogen, halogen or substituted or unsubstituted $C_{1-6}$ alkyl;
$R^3$ is hydrogen, halogen or substituted or unsubstituted $C_{1-6}$ alkyl;
$R^4$ is hydrogen, halogen or substituted or unsubstituted $C_{1-6}$ alkyl;
$R^5$ is hydrogen, halogen or substituted or unsubstituted $C_{1-6}$ alkyl;
$R^6$ is hydrogen, halogen, CN, substituted or unsubstituted $C_{1-6}$ alkyl, $OR^{12}$, $NR^{13}R^{14}$, or $COR^{15}$;
$R^7$ is hydrogen, halogen, CN, substituted or unsubstituted $C_{1-6}$ alkyl, $OR^{12}$, $NR^{13}R^{14}$, or $COR^{15}$;
$R^8$ is hydrogen, halogen, CN, substituted or unsubstituted $C_{1-6}$ alkyl, $OR^{12}$, $NR^{13}R^{14}$, or $COR^{15}$;
$R^9$ is S, S(O), S(O)$_2$;
a is 0 or 1;
$R^{11}$ is hydrogen, CN, substituted or unsubstituted $C_{1-6}$ alkyl, $CF_3$, $OR^{12}$, $NR^{13}R^{14}$, substituted or unsubstituted $C_{6-10}$ aryl, substituted or unsubstituted heterocycle, substituted or unsubstituted $C_{3-8}$ cycloalkyl, substituted or unsubstituted $C_{2-6}$ alkyne, substituted or unsubstituted $C_{2-6}$ alkene or $COR^{15}$;
$R^{12}$ is hydrogen or substituted or unsubstituted $C_{1-6}$ alkyl;
$R^{13}$ is hydrogen or substituted or unsubstituted $C_{1-6}$ alkyl or can from an optionally substituted heterocycle with $R^{14}$;
$R^{14}$ is hydrogen, substituted or unsubstituted $C_{1-6}$ alkyl, substituted or unsubstituted heterocycle or substituted or unsubstituted $C_{6-10}$ aryl or can from an optionally substituted heterocycle with $R^{13}$;
$R^{15}$ is hydrogen, hydroxyl, substituted or unsubstituted heterocycle, substituted or unsubstituted $C_{6-10}$ aryl or substituted or unsubstituted $C_{1-6}$ alkyl; and
$R^{18}$ is hydrogen or substituted or unsubstituted $C_{1-6}$ alkyl.

3. The method according to claim 1 wherein the compound of Formula I is selected from:
- N-[2-(benzylthio)-5-chloropyridin-3-yl]-1-benzofuran-2-sulfonamide;
- N-[2-(benzylsulfinyl)-5-chloropyridin-3-yl]-1-benzofuran-2-sulfonamide;
- N-[2-(benzylsulfonyl)-5-chloropyridin-3-yl]-1-benzofuran-2-sulfonamide;
- N-{5-chloro-2-[(pyridin-3-ylmethyl)thio]pyridin-3-yl}-1-benzofuran-2-sulfonamide;
- N-{5-chloro-2-[(pyridin-3-ylmethyl)sulfinyl]pyridin-3-yl}-1-benzofuran-2-sulfonamide;
- N-{5-chloro-2-[(pyridin-3-ylmethyl)sulfonyl]pyridin-3-yl}-1-benzofuran-2-sulfonamide;
- N-(5-chloro-2-{[(1-oxidopyridin-3-yl)methyl]sulfonyl}pyridin-3-yl)-1-benzofuran-2-sulfonamide;
- N-[2-(benzylthio)pyridin-3-yl]-1-benzofuran-2-sulfonamide;
- N-[2-(benzylsulfinyl)pyridin-3-yl]-1-benzofuran-2-sulfonamide;
- N-[2-(benzylsulfonyl)pyridin-3-yl]-1-benzofuran-2-sulfonamide;
- N-{2-[(3-aminobenzyl)sulfanyl]pyridin-3-yl}-1-benzofuran-2-sulfonamide;
- N-{2-[(3-aminobenzyl)sulfinyl]pyridin-3-yl}-1-benzofuran-2-sulfonamide;
- tert-butyl {3-[({3-[(1-benzofuran-2-ylsulfonyl)amino]pyridin-2-yl}sulfonyl)methyl]phenyl}carbamate;
- N-{2-[(3-aminobenzyl)sulfonyl]pyridin-3-yl}1-benzofuran-2-sulfonamide;
- N-[2-(benzylsulfanyl)-5-fluoropyridin-3-yl]-1-benzofuran-2-sulfonamide;
- N-[2-(benzylsulfinyl)-5-fluoropyridin-3-yl]-1-benzofuran-2-sulfonamide;
- N-[2-(benzylsulfonyl)-5-fluoropyridin-3-yl]-1-benzofuran-2-sulfonamide;
- N-{2-[(3-aminobenzyl)sulfanyl]-5-chloropyridin-3-yl}-1-benzofuran-2-sulfonamide;
- N-{2-[(3-aminobenzyl)sulfinyl]-5-chloropyridin-3-yl}-1-benzofuran-2-sulfonamide;
- N-{2-[(3-aminobenzyl)sulfonyl]-5-chloropyridin-3-yl}1-benzofuran-2-sulfonamide;
- N-[2-(benzylsulfanyl)-5-methylpyridin-3-yl]-1-benzofuran-2-sulfonamide;
- N-[2-(benzylsulfinyl)-5-methylpyridin-3-yl]-1-benzofuran-2-sulfonamide;
- N-[2-(benzylsulfonyl)-5-methylpyridin-3-yl]-1-benzofuran-2-sulfonamide;
- N-[5-chloro-2-(phenylsulfanyl)pyridin-3-yl]-1-benzofuran-2-sulfonamide;
- N-[5-chloro-2-(phenylsulfonyl)pyridin-3-yl]-1-benzofuran-2-sulfonamide;
- N-[5-chloro-2-(phenylsulfinyl)pyridin-3-yl]-1-benzofuran-2-sulfonamide;
- methyl 2-[({3-[(1-benzofuran-2-ylsulfonyl)amino]-5-chloropyridin-2-yl}sulfanyl)methyl]benzoate;
- 2-[({3-[(1-benzofuran-2-ylsulfonyl)amino]-5-chloropyridin-2-yl}sulfanyl)methyl]benzoic acid;
- methyl 2-[({3-[(1-benzofuran-2-ylsulfonyl)amino]-5-chloropyridin-2-yl}sulfinyl)methyl]benzoate;
- methyl 2-[({3-[(1-benzofuran-2-ylsulfonyl)amino]-5-chloropyridin-2-yl}sulfonyl)methyl]benzoate;
- 2-[({3-[(1-benzofuran-2-ylsulfonyl)amino]-5-chloropyridin-2-yl}sulfonyl)methyl]benzoic acid;
- N-[5-fluoro-2-(phenylsulfanyl)pyridin-3-yl]-1-benzofuran-2-sulfonamide;

N-[5-fluoro-2-(phenylsulfinyl)pyridin-3-yl]-1-benzofuran-2-sulfonamide;
N-[5-fluoro-2-(phenylsulfonyl)pyridin-3-yl]-1-benzofuran-2-sulfonamide;
2-[({3-[(1-benzofuran-2-ylsulfonyl)amino]-5-chloropyridin-2-yl}sulfinyl)methyl]benzoic acid;
N-[5-methyl-2-(phenylsulfanyl)pyridin-3-yl]-1-benzofuran-2-sulfonamide;
N-[5-methyl-2-(phenylsulfinyl)pyridin-3-yl]-1-benzofuran-2-sulfonamide;
N-[5-methyl-2-(phenylsulfonyl)pyridin-3-yl]-1-benzofuran-2-sulfonamide;
2-({3-[(1-benzofuran-2-ylsulfonyl)amino]-5-chloropyridin-2-yl}sulfanyl)benzoic acid;
3-({3-[(1-benzofuran-2-ylsulfonyl)amino]-5-chloropyridin-2-yl}sulfanyl)benzoic acid;
2-({3-[(1-benzofuran-2-ylsulfonyl)amino]-5-chloropyridin-2-yl}sulfinyl)benzoic acid;
2-({3-[(1-benzofuran-2-ylsulfonyl)amino]-5-chloropyridin-2-yl}sulfonyl)benzoic acid;
2-[({3-[(1-benzofuran-2-ylsulfonyl)amino]-5-methylpyridin-2-yl}sulfanyl)methyl]benzoic acid;
2-[({3-[(1-benzofuran-2-ylsulfonyl)amino]-5-methylpyridin-2-yl}sulfinyl)methyl]benzoic acid;
methyl 2-[({3-[(1-benzofuran-2-ylsulfonyl)amino]pyridin-2-yl}sulfanyl)methyl]benzoate;
2-[({3-[(1-benzofuran-2-ylsulfonyl)amino]pyridin-2-yl}sulfanyl)methyl]benzoic acid;
methyl 2-[({3-[(1-benzofuran-2-ylsulfonyl)amino]pyridin-2-yl}sulfinyl)methyl]benzoate;
2-[({3-[(1-benzofuran-2-ylsulfonyl)amino]pyridin-2-yl}sulfinyl)methyl]benzoic acid;
methyl 2-[({3-[(1-benzofuran-2-ylsulfonyl)amino]pyridin-2-yl}sulfonyl)methyl]benzoate; and
2-[({3-[(1-benzofuran-2-ylsulfonyl)amino]pyridin-2-yl}sulfonyl)methyl]benzoic acid.

4. The method of claim 1, wherein:
$R^1$ is hydrogen, halogen or substituted or unsubstituted $C_{1-6}$ alkyl;
$R^2$ is hydrogen, halogen or substituted or unsubstituted $C_{1-6}$ alkyl;
$R^3$ is hydrogen, halogen or substituted or unsubstituted $C_{1-6}$ alkyl;
$R^4$ is hydrogen, halogen or substituted or unsubstituted $C_{1-6}$ alkyl;
$R^5$ is hydrogen, halogen or substituted or unsubstituted $C_{1-6}$ alkyl;
$R^6$ is hydrogen, halogen, CN, substituted or unsubstituted $C_{1-6}$ alkyl, $OR^{12}$, $NR^{13}R^{14}$, or $COR^{15}$;
$R^7$ is hydrogen, halogen, CN, substituted or unsubstituted $C_{1-6}$ alkyl, $OR^{12}$, $NR^{13}R^{14}$, or $COR^{15}$;
$R^8$ is hydrogen, halogen, CN, substituted or unsubstituted $C_{1-6}$ alkyl, $OR^{12}$, $NR^{13}R^{14}$, or $COR^{15}$;
$R^9$ is O;
a is 0 or 1;
$R^{11}$ is hydrogen, CN, substituted or unsubstituted $C_{1-6}$ alkyl, $CF_3$, $OR^{12}$, $NR^{13}R^{14}$, substituted or unsubstituted $C_{6-10}$ aryl, substituted or unsubstituted heterocycle, substituted or unsubstituted $C_{3-8}$ cycloalkyl, substituted or unsubstituted $C_{2-6}$ alkyne, substituted or unsubstituted $C_{2-6}$ alkene or $COR^{15}$;
$R^{12}$ is hydrogen or substituted or unsubstituted $C_{1-6}$ alkyl;
$R^{13}$ is hydrogen or substituted or unsubstituted $C_{1-6}$ alkyl or can from an optionally substituted heterocycle with $R^{14}$;
$R^{14}$ is hydrogen, substituted or unsubstituted $C_{1-6}$ alkyl, substituted or unsubstituted heterocycle or substituted or unsubstituted $C_{6-10}$ aryl or can from an optionally substituted heterocycle with $R^{13}$;
$R^{15}$ is hydrogen, hydroxyl, substituted or unsubstituted heterocycle, substituted or unsubstituted $C_{6-10}$ aryl or substituted or unsubstituted $C_{1-6}$ alkyl; and
$R^{18}$ is hydrogen or substituted or unsubstituted $C_{1-6}$ alkyl.

5. The method according to claim 1 wherein:
$R^1$ is hydrogen, halogen or substituted or unsubstituted $C_{1-6}$ alkyl;
$R^2$ is hydrogen, halogen or substituted or unsubstituted $C_{1-6}$ alkyl;
$R^3$ is hydrogen, halogen or substituted or unsubstituted $C_{1-6}$ alkyl;
$R^4$ is hydrogen, halogen or substituted or unsubstituted $C_{1-6}$ alkyl;
$R^5$ is hydrogen, halogen or substituted or unsubstituted $C_{1-6}$ alkyl;
$R^6$ is hydrogen, halogen, CN, substituted or unsubstituted $C_{1-6}$ alkyl, $OR^{12}$, $NR^{13}R^{14}$, or $COR^{15}$;
$R^7$ is hydrogen, halogen, CN, substituted or unsubstituted $C_{1-6}$ alkyl, $OR^{12}$, $NR^{13}R^{14}$, or $COR^{15}$;
$R^8$ is hydrogen, halogen, CN, substituted or unsubstituted $C_{1-6}$ alkyl, $OR^{12}$, $NR^{13}R^{14}$, or $COR^{15}$;
$R^9$ is C(O);
a is 0 or 1;
$R^{11}$ is hydrogen, CN, substituted or unsubstituted $C_{1-6}$ alkyl, $CF_3$, $OR^{12}$, $NR^{13}R^{14}$, substituted or unsubstituted $C_{6-10}$ aryl, substituted or unsubstituted heterocycle, substituted or unsubstituted $C_{3-8}$ cycloalkyl, substituted or unsubstituted $C_{2-6}$ alkyne, substituted or unsubstituted $C_{2-6}$ alkene or $COR^{15}$;
$R^{12}$ is hydrogen or substituted or unsubstituted $C_{1-6}$ alkyl;
$R^{13}$ is hydrogen or substituted or unsubstituted $C_{1-6}$ alkyl or can from an optionally substituted heterocycle with $R^{14}$;
$R^{14}$ is hydrogen, substituted or unsubstituted $C_{1-6}$ alkyl, substituted or unsubstituted heterocycle or substituted or unsubstituted $C_{6-10}$ aryl or can from an optionally substituted heterocycle with $R^{13}$;
$R^{15}$ is hydrogen, hydroxyl, substituted or unsubstituted heterocycle, substituted or unsubstituted $C_{6-10}$ aryl or substituted or unsubstituted $C_{1-6}$ alkyl; and
$R^{18}$ is hydrogen or substituted or unsubstituted $C_{1-6}$ alkyl.

6. The method according to claim 1 wherein:
$R^1$ is hydrogen, halogen or substituted or unsubstituted $C_{1-6}$ alkyl;
$R^2$ is hydrogen, halogen or substituted or unsubstituted $C_{1-6}$ alkyl;
$R^3$ is hydrogen, halogen or substituted or unsubstituted $C_{1-6}$ alkyl;
$R^4$ is hydrogen, halogen or substituted or unsubstituted $C_{1-6}$ alkyl;
$R^5$ is hydrogen, halogen or substituted or unsubstituted $C_{1-6}$ alkyl;
$R^6$ is hydrogen, halogen, CN, substituted or unsubstituted $C_{1-6}$ alkyl, $OR^{12}$, $NR^{13}R^{14}$, or $COR^{15}$;
$R^7$ is hydrogen, halogen, CN, substituted or unsubstituted $C_{1-6}$ alkyl, $OR^{12}$, $NR^{13}R^{14}$, or $COR^{15}$;
$R^8$ is hydrogen, halogen, CN, substituted or unsubstituted $C_{1-6}$ alkyl, $OR^{12}$, $NR^{13}R^{14}$, or $COR^{15}$;
$R^9$ is —C(=NOR$^{16}$)—;
a is 0 or 1;
$R^{11}$ is hydrogen, CN, substituted or unsubstituted $C_{1-6}$ alkyl, $CF_3$, $OR^{12}$, $NR^{13}R^{14}$, substituted or unsubstituted $C_{6-10}$ aryl, substituted or unsubstituted heterocycle, substituted or unsubstituted $C_{3-8}$ cycloalkyl, substituted or unsubstituted $C_{2-6}$ alkyne, substituted or unsubstituted $C_{2-6}$ alkene or $COR^{15}$;

$R^{12}$ is hydrogen or substituted or unsubstituted $C_{1-6}$ alkyl;

$R^{13}$ is hydrogen or substituted or unsubstituted $C_{1-6}$ alkyl or can from an optionally substituted heterocycle with $R^{14}$;

$R^{14}$ is hydrogen, substituted or unsubstituted $C_{1-6}$ alkyl, substituted or unsubstituted heterocycle or substituted or unsubstituted $C_{6-10}$ aryl or can from an optionally substituted heterocycle with $R^{13}$;

$R^{15}$ is hydrogen, hydroxyl, substituted or unsubstituted heterocycle, substituted or unsubstituted $C_{6-10}$ aryl or substituted or unsubstituted $C_{1-6}$ alkyl;

$R^{16}$ is hydrogen or substituted or unsubstituted $C_{1-6}$ alkyl; and $R^{18}$ is hydrogen or substituted or unsubstituted $C_{1-6}$ alkyl.

7. The method according to claim 1 wherein the compound of Formula I is selected from:

N-[2-(benzylsulfanyl)-5-chloropyridin-3-yl]-1-benzofuran-2-sulfonamide;

N-[2-(benzylsulfinyl)-5-chloropyridin-3-yl]-1-benzofuran-2-sulfonamide;

N-[2-(benzylsulfonyl)-5-chloropyridin-3-yl]-1-benzofuran-2-sulfonamide;

N-{5-chloro-2-[(pyridin-3-ylmethyl)sulfanyl]pyridin-3-yl}-1-benzofuran-2-sulfonamide;

N-{5-chloro-2-[(pyridin-3-ylmethyl)sulfinyl]pyridin-3-yl}-1-benzofuran-2-sulfonamide;

N-{5-chloro-2-[(pyridin-3-ylmethyl)sulfonyl]pyridin-3-yl}-1-benzofuran-2-sulfonamide;

N-(5-chloro-2{-[(1-oxidopyridin-3-yl)methyl]sulfonyl}pyridin-3-yl)-1-benzofuran-2-sulfonamide;

N-[2-(benzylsulfanyl)pyridin-3-yl]-1-benzofuran-2-sulfonamide;

N-[2-(benzylsulfinyl)pyridin-3-yl]-1-benzofuran-2-sulfonamide;

N-[2-(benzylsulfonyl)pyridin-3-yl]-1-benzofuran-2-sulfonamide;

N-{2-[(3-aminobenzyl)sulfanyl]pyridin-3-yl}-1-benzofuran-2-sulfonamide;

N-{2-[(3-aminobenzyl)sulfinyl]pyridin-3-yl}-1-benzofuran-2-sulfonamide;

tert-butyl {3-[({3-[(1-benzofuran-2-ylsulfonyl)amino]pyridin-2-yl}sulfonyl)methyl]phenyl}carbamate;

N-{2-[(3-aminobenzyl)sulfonyl]pyridin-3-yl}-1-benzofuran-2-sulfonamide;

N-[2-(benzylsulfanyl)-5-fluoropyridin-3-yl]-1-benzofuran-2-sulfonamide;

N-[2-(benzylsulfinyl)-5-fluoropyridin-3-yl]-1-benzofuran-2-sulfonamide;

N-[2-(benzylsulfonyl)-5-fluoropyridin-3-yl]-1-benzofuran-2-sulfonamide;

N-{2-[(3-aminobenzyl)sulfanyl]-5-chloropyridin-3-yl}-1-benzofuran-2-sulfonamide;

N-{2-[(3-aminobenzyl)sulfinyl]-5-chloropyridin-3-yl}-1-benzofuran-2-sulfonamide;

N-{2-[(3-aminobenzyl)sulfonyl]-5-chloropyridin-3-yl}-1-benzofuran-2-sulfonamide;

N-[2-(benzylsulfanyl)-5-methylpyridin-3-yl]-1-benzofuran-2-sulfonamide;

N-[2-(benzylsulfinyl)-5-methylpyridin-3-yl]-1-benzofuran-2-sulfonamide;

N-[2-(benzylsulfonyl)-5-methylpyridin-3-yl]-1-benzofuran-2-sulfonamide;

N-{5-chloro-2-[(2-methylpyridin-3-yl)oxy]pyridin-3-yl}-1-benzofuran-2-sulfonamide;

2-({3-[(1-benzofuran-2-ylsulfonyl)amino]-5-chloropyridin-2-yl}oxy)benzoic acid;

methyl 2-({3-[(1-benzofuran-2-ylsulfonyl)amino]-5-chloropyridin-2-yl}oxy)benzoate;

N-[5-chloro-2-(morpholin-4-ylcarbonyl)pyridin-3-yl]-1-benzofuran-2-sulfonamide;

N-{5-chloro-2-[(4-oxopiperidin-1-yl)carbonyl]pyridin-3-yl}-1-benzofuran-2-sulfonamide;

N-[5-chloro-2-(phenylcarbonyl)pyridin-3-yl]-1-benzofuran-2-sulfonamide;

N-[5-chloro-2-(phenylsulfanyl)pyridin-3-yl]-1-benzofuran-2-sulfonamide;

N-[5-chloro-2-(phenylsulfonyl)pyridin-3-yl]-1-benzofuran-2-sulfonamide;

N-[5-chloro-2-(phenylsulfinyl)pyridin-3-yl]-1-benzofuran-2-sulfonamide;

N-{5-chloro-2-[(2-methylpyridin-3-yl)methoxy]pyridin-3-yl}-1-benzofuran-2-sulfonamide;

N-[5-chloro-2-(phenylacetyl)pyridin-3-yl]-1-benzofuran-2-sulfonamide;

methyl 2-[({3-[(1-benzofuran-2-ylsulfonyl)amino]-5-chloropyridin-2-yl}sulfanyl)methyl]benzoate;

2-[({3-[(1-benzofuran-2-ylsulfonyl)amino]-5-chloropyridin-2-yl}sulfanyl)methyl]benzoic acid;

methyl 2-[({3-[(1-benzofuran-2-ylsulfonyl)amino]-5-chloropyridin-2-yl}sulfinyl)methyl]benzoate;

methyl 2-[({3-[(1-benzofuran-2-ylsulfonyl)amino]-5-chloropyridin-2-yl}sulfonyl)methyl]benzoate;

2-[({3-[(1-benzofuran-2-ylsulfonyl)amino]-5-chloropyridin-2-yl}sulfonyl)methyl]benzoic acid;

N-[5-fluoro-2-(phenylsulfanyl)pyridin-3-yl]-1-benzofuran-2-sulfonamide;

N-[5-fluoro-2-(phenylsulfinyl)pyridin-3-yl]-1-benzofuran-2-sulfonamide;

N-[5-fluoro-2-(phenylsulfonyl)pyridin-3-yl]-1-benzofuran-2-sulfonamide;

2-[({3-[(1-benzofuran-2-ylsulfonyl)amino]-5-chloropyridin-2-yl}sulfinyl)methyl]benzoic acid;

N-[5-methyl-2-(phenylsulfanyl)pyridin-3-yl]-1-benzofuran-2-sulfonamide;

N-[5-methyl-2-(phenylsulfinyl)pyridin-3-yl]-1-benzofuran-2-sulfonamide;

N-[5-methyl-2-(phenylsulfonyl)pyridin-3-yl]-1-benzofuran-2-sulfonamide;

2-({3-[(1-benzofuran-2-ylsulfonyl)amino]-5-chloropyridin-2-yl}sulfanyl)benzoic acid;

3-({3-[(1-benzofuran-2-ylsulfonyl)amino]-5-chloropyridin-2-yl}sulfanyl)benzoic acid;

2-({3-[(1-benzofuran-2-ylsulfonyl)amino]-5-chloropyridin-2-yl}sulfinyl)benzoic acid;

2-({3-[(1-benzofuran-2-ylsulfonyl)amino]-5-chloropyridin-2-yl}sulfonyl)benzoic acid;

2-[({3-[(1-benzofuran-2-ylsulfonyl)amino]-5-methylpyridin-2-yl}sulfanyl)methyl]benzoic acid;

2-[({3-[(1-benzofuran-2-ylsulfonyl)amino]-5-methylpyridin-2-yl}sulfinyl)methyl]benzoic acid;

methyl 2-[({3-[(1-benzofuran-2-ylsulfonyl)amino]pyridin-2-yl}sulfanyl)methyl]benzoate;

2-[({3-[(1-benzofuran-2-ylsulfonyl)amino]pyridin-2-yl}sulfanyl)methyl]benzoic acid;

methyl 2-[({3-[(1-benzofuran-2-ylsulfonyl)amino]pyridin-2-yl}sulfinyl)methyl]benzoate;

2-[({3-[(1-benzofuran-2-ylsulfonyl)amino]pyridin-2-yl}sulfinyl)methyl]benzoic acid;
methyl 2-[({3-[(1-benzofuran-2-ylsulfonyl)amino]pyridin-2-yl}sulfonyl)methyl]benzoate; and
2-[({3-[(1-benzofuran-2-ylsulfonyl)amino]pyridin-2-yl}sulfonyl)methyl]benzoic acid.

8. The method of claim 1 wherein the mammal is a human.

* * * * *